(12) United States Patent
Katoh et al.

(10) Patent No.: US 8,126,655 B2
(45) Date of Patent: Feb. 28, 2012

(54) INFORMATION PROCESSING SYSTEM USING INFORMATION ON BASE SEQUENCE

(75) Inventors: Takamasa Katoh, Tokorozawa (JP); Takeo Morimoto, Koshigaya (JP)

(73) Assignee: Hitachi, Ltd., Tokyo (JP)

( * ) Notice: Subject to any disclaimer, the term of this patent is extended or adjusted under 35 U.S.C. 154(b) by 350 days.

(21) Appl. No.: 10/496,588

(22) PCT Filed: Nov. 14, 2002

(86) PCT No.: PCT/JP02/11891
§ 371 (c)(1), (2), (4) Date: May 24, 2004

(87) PCT Pub. No.: WO03/048991
PCT Pub. Date: Jun. 12, 2003

(65) Prior Publication Data
US 2004/0259099 A1    Dec. 23, 2004

(30) Foreign Application Priority Data
Nov. 22, 2001  (JP) .................................. 2001-357470

(51) Int. Cl.
G06F 19/00 (2011.01)
G06F 21/00 (2006.01)
G06Q 50/00 (2006.01)
(52) U.S. Cl. ................................ 702/20; 705/3; 705/51
(58) Field of Classification Search .................. None
See application file for complete search history.

(56) References Cited

U.S. PATENT DOCUMENTS

| | | | |
|---|---|---|---|
| 5,479,513 A | 12/1995 | Protopopescu et al. | |
| 5,970,500 A | 10/1999 | Sabatini et al. | |
| 5,985,559 A | 11/1999 | Brown | |
| 6,282,656 B1 * | 8/2001 | Wang ............................... | 726/4 |
| 6,537,747 B1 * | 3/2003 | Mills et al. ......................... | 435/6 |
| 6,874,085 B1 * | 3/2005 | Koo et al. ......................... | 713/165 |
| 2001/0043217 A1 | 11/2001 | Maloney et al. | |
| 2001/0052851 A1 | 12/2001 | Mathias et al. | |
| 2002/0010552 A1 | 1/2002 | Rienhoff et al. | |
| 2002/0197635 A1 | 12/2002 | Kato et al. | |
| 2003/0125883 A1 | 7/2003 | Kato et al. | |
| 2005/0086011 A1 | 4/2005 | Kato et al. | |
| 2005/0114040 A1 | 5/2005 | Kato et al. | |

FOREIGN PATENT DOCUMENTS

| | | |
|---|---|---|
| JP | 2000-67139 A | 3/2000 |
| JP | 2001-195367 A | 7/2001 |
| WO | WO 01/01218 A2 | 1/2001 |
| WO | WO 01/26029 A2 | 4/2001 |
| WO | WO 01/28415 A1 | 4/2001 |
| WO | WO 01/46895 A2 | 6/2001 |
| WO | WO 01/69430 A1 | 9/2001 |
| WO | WO 02/17190 A1 | 2/2002 |
| WO | WO 02/25519 A1 | 3/2002 |
| WO | WO 02/25528 A1 | 3/2002 |

OTHER PUBLICATIONS

Benkendorf et al. Patient's Attitudes About Autonomy and Confidentiality in Genetic Testing for Breast-Ovarian Cancer Susceptibility. Amer. J. Med. Genet. vol. 73, pp. 296-303 (1997).*
Fuller et al. Privacy in Genetic Research Science vol. 285 pp. 1359-1361 (1999).*
Felson et al. Evidence for a Mendelian Gene in a Segregation Analysis of Generalized Radiographic Osteoarthritis Arthritis & Rheumatism vol. 41, pp. 1064-1071 (1998).*
Burke et al. Architectural Support for Fast Symmetric-Key Cryptography ACM Sigarch Computer Architecture News Special Issue: Proceedings of the ninth international conference on Architectural support for programming languages and operating systems (ASPLOS '00) vol. 28, Issue 5, Dec. 2000.*
Wang, Cliff, "Security Issues to Tele-Medicine System Design", IEEE, pp. 106-109, 1999.
Qiagen Product Guide 2000, Qiagen Inc., Valencia, CA, pp. 250-253, 2000.

\* cited by examiner

*Primary Examiner* — John S Brusca
(74) *Attorney, Agent, or Firm* — Dickstein Shapiro LLP

(57) ABSTRACT

The present invention provides a highly-safe information processing system that is capable of effectively using nucleotide sequence information differences between individual organisms to offer semantic information useful for each individual organism while properly preventing leakage and illegal use of nucleotide sequence information.

Further, the present invention includes steps a and b. Step a is performed to acquire either encrypted nucleotide sequence-related information or cryptographic key that corresponds to positional information indicating a position within a nucleotide sequence. Step b is performed to acquire the encrypted nucleotide sequence-related information or cryptographic key, whichever is not acquired in said step a, decrypt, with the cryptographic key, the encrypted nucleotide sequence-related information corresponding to the positional information compliant at least with a request for an object and/or a service, and acquire the nucleotide sequence-related information corresponding to the positional information compliant at least with the request for an object and/or a service.

9 Claims, 34 Drawing Sheets

FIG.3

| POLYMORPHISM ADDRESS | ... | POLYMORPHISM CATEGORY | POLYMORPHISM PATTERN | CATEGORY (DISEASE NAME) | ANNOTATIVE INFORMATION ON POLYMORPHISM PATTERN (MORBIDITY) | ... | DISCLOSURE LEVEL (DISCLOSABILITY) |
|---|---|---|---|---|---|---|---|
| 123456 | ... | SNP | A | HYPERTENSION | a | ... | ○ |
| 123456 | ... | SNP | G | HYPERTENSION | b | ... | ○ |
| 223456 | ... | SNP | G | COLORECTAL CANCER | (I) | ... | ○ |
| 223456 | ... | SNP | A | COLORECTAL CANCER | (II) | ... | ○ |
| 234567 | ... | SNP | G | STOMACH CANCER | c | ... | ○ |
| 234567 | ... | SNP | A | STOMACH CANCER | d | ... | ○ |
| 334567 | ... | SNP | A | ASTHMA | (III) | ... | ○ |
| 334567 | ... | SNP | G | ASTHMA | (IV) | ... | ○ |
| 345678 | ... | SNP | C | DIABETES | e | ... | ○ |
| 345678 | ... | SNP | T | DIABETES | f | ... | ○ |
| 445678 | ... | SNP | T | LUNG CANCER | (i) | ... | ○ |
| 445678 | ... | SNP | C | LUNG CANCER | (ii) | ... | ○ |
| 456789 | ... | SNP | T | POLLINOSIS | g | ... | ○ |
| 456789 | ... | SNP | C | POLLINOSIS | h | ... | ○ |
| ... | ... | MICROSATELLITE | 14 TIMES | INCURABLE DISEASE | — | .. | × |
| ... | ... | MICROSATELLITE | 9 TIMES | INCURABLE DISEASE | — | .. | × |
| ... | ... | DELETION | G | .. | .. | .. | ○ |
| ... | ... | DELETION | DELETION | .. | .. | .. | ○ |

| Gno. | BIRTH DATE |
|---|---|
| 0001 | ..**** |

II

| POLYMOR-PHISM ADDRESS | ENCRYPTED POLYMORPHISM PATTERN | COMMENT |
|---|---|---|
| 000001 | φ | ...... |
| 000002 | φ | ...... |
| : | : | : |
| 123456 | G | ...... |
| : | : | : |
| 223456 | G | ...... |
| : | : | : |
| 234567 | T | ...... |
| : | : | : |
| 334567 | φ | ...... |
| : | : | : |
| 345678 | C | ...... |
| : | : | : |
| 445678 | A | ...... |
| : | : | : |
| 456789 | φ | ...... |
| 456790 | A | ...... |
| 456791 | 17 TIMES | ...... |
| 456792 | G | ...... |
| : | : | : |

III

| ANAMNESIS |
|---|
| INFANTILE ASTHMA |
| GOUT |
| POLLINOSIS |
| GASTRIC ULCER |
| ATOPY |
| HYPERTENSION |
| DIABETES |
| |
| |
| |
| |

IV

| CHARACTER-ISTICS | RECORD |
|---|---|
| BLOOD TYPE | ...... |
| BODY HEIGHT | ...... |
| BODY WEIGHT | ...... |
| EYESIGHT | ...... |
| RUNNING ABILITY | ...... |
| PSYCHOLOGICAL TEST | ...... |
| : | : |
| : | : |
| : | : |

V ......

......
(CLINICAL CHART RECORDINGS, ETC.)
......
......
......
......
......
......
......
......
......
......
......

FIG.6

| ENCRYPTED POLYMORPHISM PATTERN / RANDOM NUMBER | φ | A | G | C | T |
|---|---|---|---|---|---|
| 0 | φ | A | G | C | T |
| 1 | T | φ | A | G | C |
| 2 | C | T | φ | A | G |
| 3 | G | C | T | φ | A |
| 4 | A | G | C | T | φ |
| 5 | φ | A | G | C | T |
| 6 | T | φ | A | G | C |
| 7 | C | T | φ | A | G |
| 8 | G | C | T | φ | A |
| 9 | A | G | C | T | φ |

FIG.8

| POLYMORPHISM ADDRESS | Gno. 0001 | Gno. 0002 | Gno. 0003 | ... |
|---|---|---|---|---|
| 000001 | 3 | 5 | 4 | ... |
| 000002 | 1 | 2 | 6 | ... |
| ⋮ | ⋮ | ⋮ | ⋮ | ⋮ |
| 123456 | 6 | 3 | 8 | ... |
| ⋮ | ⋮ | ⋮ | ⋮ | ⋮ |
| 223456 | 0 | 1 | 0 | ... |
| ⋮ | ⋮ | ⋮ | ⋮ | ⋮ |
| 234567 | 2 | 8 | 5 | ... |
| ⋮ | ⋮ | ⋮ | ⋮ | ⋮ |
| 334567 | 8 | 5 | 9 | ... |
| ⋮ | ⋮ | ⋮ | ⋮ | ⋮ |
| 345678 | 5 | 9 | 4 | ... |
| ⋮ | ⋮ | ⋮ | ⋮ | ⋮ |
| 445678 | 7 | 2 | 3 | ... |
| ⋮ | ⋮ | ⋮ | ⋮ | ⋮ |
| 456789 | 9 | 4 | 0 | ... |
| 456790 | 4 | 0 | 8 | ... |
| 456791 | 3 | 7 | 6 | ... |
| 456792 | 7 | 1 | 2 | ... |
| ⋮ | ⋮ | ⋮ | ⋮ | ⋮ |

| Gno. | BIRTH DATE |
|---|---|
| 0001 | ..**** |

II

| POLYMOR-PHISM ADDRESS | RANDOM NUMBER | COMMENT |
|---|---|---|
| 000001 | 3 | ...... |
| 000002 | 1 | ...... |
| : | : | : |
| 123456 | 6 | ...... |
| : | : | : |
| 223456 | 0 | ...... |
| : | : | : |
| 234567 | 2 | ...... |
| : | : | : |
| 334567 | 8 | ...... |
| : | : | : |
| 345678 | 5 | ...... |
| : | : | : |
| 445678 | 7 | ...... |
| : | : | : |
| 456789 | 9 | ...... |
| 456790 | 4 | ...... |
| 456791 | 3 | ...... |
| 456792 | 7 | ...... |
| : | : | : |

III

| ANAMNESIS |
|---|
| INFANTILE ASTHMA |
| GOUT |
| POLLINOSIS |
| GASTRIC ULCER |
| ATOPY |
| HYPERTENSION |
| DIABETES |
| |
| |
| |

IV

| CHARACTER-ISTICS | RECORD |
|---|---|
| BLOOD TYPE | ...... |
| BODY HEIGHT | ...... |
| BODY WEIGHT | ...... |
| EYESIGHT | ...... |
| RUNNING ABILITY | ...... |
| PSYCHOLOGICAL TEST | ...... |
| : | : |
| : | : |
| : | : |

V ......

| (CLINICAL CHART RECORDINGS, ETC.) |
|---|
| ...... |
| ...... |
| ...... |
| ...... |
| ...... |
| ...... |
| ...... |
| ...... |
| ...... |
| ...... |
| ...... |

FIG.34

| POLYMOR-PHISM ADDRESS | Gno. 0001 | Gno. 0002 | Gno. 0003 | ... |
|---|---|---|---|---|
| 000001 | φ | : | : | ... |
| 000002 | φ | : | : | ... |
| : | : | : | : | : |
| 123456 | G | : | : | ... |
| : | : | : | : | : |
| 223456 | G | : | : | ... |
| : | : | : | : | : |
| 234567 | T | : | : | ... |
| : | : | : | : | : |
| 334567 | φ | : | : | ... |
| : | : | : | : | : |
| 345678 | C | : | : | ... |
| : | : | : | : | : |
| 445678 | A | : | : | ... |
| : | : | : | : | : |
| 456789 | φ | : | : | ... |
| 456790 | A | : | : | ... |
| 456791 | 17 TIMES | : | : | ... |
| 456792 | G | : | : | ... |
| : | : | : | : | : |

INFORMATION PROCESSING SYSTEM USING INFORMATION ON BASE SEQUENCE

TECHNICAL FIELD

The present invention relates to an information processing system that provide information through a communication network.

BACKGROUND ART

Currently, genomic nucleotide sequences of various organisms including humans are being rapidly determined, and the information on genomic nucleotide sequences is being accumulated in various databases. For example, currently in progress is the construction of a system that will enable various research institutes and researchers to utilize the information on genomic nucleotide sequences accumulated in databases through an information network such as the Internet.

At the same time, various activities such as researches for genomic drug discovery and analyses of genetic information have been actively conducted using nucleotide sequences contained in the above-mentioned information on genomic nucleotide sequences, and differences in nucleotide sequence among individual organisms represented by the single nucleotide polymorphism are attracting attention. In general, nucleotide sequence differences among individual organisms refer to a polymorphism, which is defined by existence of a predetermined nucleotide difference at a frequency of 1% or more in an individual species, and a variation, which is defined by a predetermined nucleotide difference of less than 1% in an individual species. In particular, known polymorphisms are an SNP (Single Nucleotide Polymorphism), in which there is one nucleotide difference among individual organisms; an insertion/deletion polymorphism, in which one to several tens of nucleotides (sometimes several thousands of nucleotides) are deleted or inserted; a VNTR (Variable Number of Tandem Repeat), in which the number of repetitions of a sequence comprising two to several tens of nucleotides as one unit varies; and a microsatellite polymorphism (a repetition sequence having about two to four nucleotides).

Such polymorphisms sometimes affect, for example, differences in amino acid sequences of proteins among individual organisms or differences in expression efficiency concerning predetermined genes among individual organisms. It is known that such influences cause, for example, differences in the morbidity rate of a predefined disease among individual organisms or differences in sensitiveness to predetermined medicaments among individual organisms.

In reality, however, the system for providing semantic information useful for each organism by making effective use of differences in nucleotide sequence-related information among a plurality of individual organisms, such as polymorphisms, is not yet constructed.

DISCLOSURE OF INVENTION

The present invention has been made in view of the above circumstances, and provides an information processing system that is capable of providing semantic information useful for each individual organism and/or information related to the semantic information by making effective use of differences in nucleotide sequence information among individual organisms and assuring high security, for instance, by preventing the leakage of the information on a nucleotide sequence.

The present invention, whereby the above objects have been achieved, includes the following features.

An information processing method concerning a nucleotide sequence, according to the present invention, makes it possible to obtain nucleotide sequence-related information, which corresponds to specified positional information, in compliance with an object request and/or service request by using a cryptographic key, which encrypts nucleotide sequence-related information, and encrypted nucleotide sequence-related information, which is encrypted by the cryptographic key. In other words, the nucleotide sequence-related information corresponding to specified positional information is obtained by decrypting encrypted nucleotide sequence-related information, which corresponds to the specified positional information, by using a cryptographic key corresponding to the specified positional information. The information processing method concerning a nucleotide sequence, according to the present invention, involves a group of three sections. A first section requests an object and/or service. A second section acquires semantic information and/or information related to the semantic information. A third section possesses either a cryptographic key or encrypted nucleotide sequence-related information. When the information processing method concerning a nucleotide sequence according to the present invention is used, the decryption can be achieved by at least one of these three sections.

For the section that requests an object and/or service, the information processing method concerning a nucleotide sequence, according to the present invention, includes steps a and b. Step a is performed to acquire either encrypted nucleotide sequence-related information or cryptographic key that corresponds to the positional information indicating a position within a nucleotide sequence. Step b is performed to acquire the encrypted nucleotide sequence-related information or cryptographic key, whichever is not acquired in step a, decrypt, with the cryptographic key, the encrypted nucleotide sequence-related information corresponding to the positional information compliant at least with a request for an object and/or service, and acquire the nucleotide sequence-related information corresponding to the positional information compliant with at least the request for an object and/or service.

The information processing method concerning a nucleotide sequence may be applied to decrypt the encrypted nucleotide sequence-related information corresponding to the whole positional information or decrypt the encrypted nucleotide sequence-related information corresponding to part of the positional information. Further, the information processing method concerning a nucleotide sequence may be applied to decrypt the encrypted nucleotide sequence-related information that corresponds to the positional information compliant with the request for an object and/or service. Furthermore, the information processing method concerning a nucleotide sequence may be applied to transmit the nucleotide sequence-related information derived from step b in addition to the request for an object and/or service or issue the request for an object and/or service in advance.

When the information processing method concerning a nucleotide sequence is used to acquire in advance the positional information indicating a position within a nucleotide sequence compliant with a request for an object and/or service, multiple sets of nucleotide sequence-related information corresponding to the positional information, the semantic information associated with each of the multiple sets of nucleotide sequence-related information and/or the information related to the semantic information, desired semantic information and/or the information related to the semantic information can be extracted in accordance with the nucleotide sequence-related information obtained in step b.

For the section that acquires semantic information and/or information related to the semantic information, the information processing method concerning a nucleotide sequence, according to the present invention, includes steps a, b, and c. Step a is performed to receive the information about a request for an object and/or service. Step b is performed to acquire encrypted nucleotide sequence-related information and cryptographic key that correspond to the positional information indicating a position within a nucleotide sequence, decrypt the encrypted nucleotide sequence-related information with the cryptographic key, and acquire the nucleotide sequence-related information corresponding to the positional information. Step c is performed to acquire semantic information implied by the nucleotide sequence-related information obtained in step b above and/or the information related to the semantic information.

In the information processing method concerning a nucleotide sequence, step b may be performed to acquire both the encrypted nucleotide sequence-related information and cryptographic key corresponding to the whole positional information, acquire both the encrypted nucleotide sequence-related information and cryptographic key corresponding to part of the positional information, or acquire both the encrypted nucleotide sequence-related information and cryptographic key that correspond to the positional information compliant with a request for an object and/or service.

The information processing method concerning a nucleotide sequence may be applied to decrypt the encrypted nucleotide sequence-related information corresponding to the whole positional information or decrypt the encrypted nucleotide sequence-related information corresponding to part of the positional information. Further, the information processing method concerning a nucleotide sequence may be applied to decrypt the encrypted nucleotide sequence-related information that corresponds to the positional information compliant with a request for an object and/or service.

For the section that possesses either a cryptographic key or encrypted nucleotide sequence-related information, the information processing method concerning a nucleotide sequence, according to the present invention, includes steps a, b, and c. Step a is performed to read either encrypted nucleotide sequence-related information or cryptographic key corresponding to specified positional information from a storage device, which stores the association between positional information indicating a position within a nucleotide sequence and either encrypted nucleotide sequence-related information or cryptographic key. Step b is performed to acquire either encrypted nucleotide sequence-related information or cryptographic key corresponding to the specified positional information, whichever is not read in step a, decrypt the encrypted nucleotide sequence-related information with the cryptographic key, and acquire the nucleotide sequence-related information corresponding to the specified positional information. Step c is performed to transmit information about the association between the nucleotide sequence-related information obtained in step b above and the positional information.

In the information processing method concerning a nucleotide sequence, step a may be performed to read the whole positional information and either the encrypted nucleotide sequence-related information or cryptographic key corresponding to the whole positional information, read part of the positional information and either the encrypted nucleotide sequence-related information or cryptographic key corresponding to the read positional information, or read specified positional information and either the encrypted nucleotide sequence-related information or cryptographic key corresponding to the specified positional information.

Prior to step b, the information processing method concerning a nucleotide sequence may be used to request the presentation of the whole or part of either the encrypted nucleotide sequence-related information or cryptographic key, whichever is not read in step a, or request the presentation of either the specified encrypted nucleotide sequence-related information or cryptographic key, whichever is not read in step a.

In the information processing method concerning a nucleotide sequence, step b may be performed to decrypt the whole encrypted nucleotide sequence-related information, decrypt part of the encrypted nucleotide sequence-related information, or decrypt specified encrypted nucleotide sequence-related information. Further, step c of the information processing method concerning a nucleotide sequence may be performed to transmit the whole nucleotide sequence-related information obtained in step b or transmit part of the nucleotide sequence-related information obtained in step b.

After completion of step c of the information processing method concerning a nucleotide sequence, billing information concerning decryption with a cryptographic key and/or nucleotide sequence-related information transmission in step c above may also be transmitted. The billing information and the nucleotide sequence-related information may be transmitted to different respective destinations.

For the section that requests an object and/or service in a situation where decryption is performed by a section other than the section that requests an object and/or service, the information processing method concerning a nucleotide sequence, according to the present invention, includes steps a and b. Step a is performed to acquire either encrypted nucleotide sequence-related information or cryptographic key that corresponds to positional information indicating a position within a nucleotide sequence. Step b is performed to transmit information about the association between positional information compliant at least with a request for an object and/or service and the encrypted nucleotide sequence-related information and/or cryptographic key corresponding to the positional information.

In the information processing method concerning a nucleotide sequence, step a may be performed to acquire the whole encrypted nucleotide sequence-related information or cryptographic key, acquire part of the encrypted nucleotide sequence-related information or cryptographic key, or acquire only a portion of the encrypted nucleotide sequence-related information or cryptographic key that corresponds to the request for an object and/or service.

In the information processing method concerning a nucleotide sequence, step b may be performed to transmit encrypted nucleotide sequence-related information and/or cryptographic key that correspond to the positional information compliant with the request for an object and/or service. Step b may also be performed to transmit encrypted nucleotide sequence-related information and/or cryptographic key that correspond to positional information other than the positional information compliant with the request for an object and/or service. When step b is performed to transmit the association between the encrypted nucleotide sequence-related information and/or cryptographic key and the positional information, it is not necessary to recognize whether the positional information relates to the request for an object and/or service. In other words, the requirements are met as far as the information corresponding to the positional information compliant with the request for an object and/or service is contained in the encrypted nucleotide sequence-related information and/or cryptographic key transmitted in step b.

The above information processing method concerning a nucleotide sequence may further include step c, which acquires the encrypted nucleotide sequence-related information or cryptographic key, whichever is not acquired in step a. In this instance, step b of the information processing method concerning a nucleotide sequence may be performed to transmit the encrypted nucleotide sequence-related information or cryptographic key, whichever is acquired in step c. In other words, step b may be performed to transmit the association between the positional information and the encrypted nucleotide sequence-related information and cryptographic key.

The above information processing method concerning a nucleotide sequence may further include step d, which acquires positional information compliant with the request for an object and/or service. In this instance, either the encrypted nucleotide sequence-related information or cryptographic key that relates to the positional information acquired in step d can be acquired in step a.

For the section that possesses either a cryptographic key or encrypted nucleotide sequence-related information in a situation where decryption is performed by a section other than the section that possesses either a cryptographic key or encrypted nucleotide sequence-related information, the nucleotide information processing method concerning a nucleotide sequence, according to the present invention, includes steps a and b. Step a is performed to read specified positional information and either encrypted nucleotide sequence-related information or cryptographic key corresponding to the specified positional information from a storage device, which stores the association between positional information indicating a position within a nucleotide sequence and either encrypted nucleotide sequence-related information or cryptographic key. Step b is performed to transmit the read positional information and either encrypted nucleotide sequence-related information or cryptographic key corresponding to the read positional information.

The above information processing method concerning a nucleotide sequence may be applied to read and transmit the whole of the positional information and other information stored in the storage device, read and transmit part of the positional information and other information stored in the storage device, or read and transmit specified positional information and other specified information stored in the storage device.

The above information processing method concerning a nucleotide sequence may further include step c, which, subsequently to step a, transmits billing information about the presentation of either encrypted nucleotide sequence-related information or cryptographic key. In this instance, the information processing method concerning a nucleotide sequence may be applied to transmit the billing information and either the positional information, the encrypted nucleotide sequence-related information, or cryptographic key to different respective destinations.

The information processing method concerning a nucleotide sequence according to the present invention may be implemented as a program that causes a computer, which is equipped with a control device, transmitter/receiver device, storage device, and other hardware, to execute the steps. Further, the information processing method concerning a nucleotide sequence, according to the present invention, may also be implemented as a recording medium for storing a program that causes a computer, which is equipped with a control device, transmitter/receiver device, storage device, and other hardware, to execute the steps. Furthermore, the information processing method concerning a nucleotide sequence, according to the present invention, may also be implemented as an information processing device that is equipped with a control device, transmitter/receiver device, storage device, and other hardware to execute the steps.

The present invention is configured as defined by the appended claims.

BRIEF DESCRIPTION OF THE DRAWINGS

FIG. 3 illustrates a typical structure of data recorded in a main database.

FIG. 5 illustrates a typical structure of data recorded on a genome-related information recording medium.

FIG. 6 illustrates a typical structure of data recorded in a decryption table.

FIG. 8 illustrates a typical structure of data recorded in a random number database.

FIG. 33 illustrates a typical structure of data recorded on a genome-related information recording medium according to a third embodiment of the present invention.

FIG. 34 illustrates a typical structure of data recorded in an encrypted polymorphism pattern database according to the third embodiment of the present invention.

1 . . . Communication network, 2 . . . Shared computer, 3 . . . Personal computer, S . . . Decryption computer

BEST MODE FOR CARRYING OUT THE INVENTION

The present invention will now be described in detail with reference to the accompanying drawings.

1. First Embodiment

First of all, an information processing system for providing morbidity rates of predefined diseases to a user in accordance with a first embodiment of the present invention will be described. The following explanation assumes that the user issues a "request for an object and/or service", for instance, to indicate that the user wants to know about the user's morbidity rates of predefined diseases. The present embodiment will be described with particular reference to an information processing system that uses encrypted nucleotide sequence-related information. For convenience of explanation, however, a simplified model of such a system will be described. The term "object and/or service" refers to medical supplies, foods, luxury goods, and other objects suitable for the diathesis of an individual (individual organism), and an information service and other services suitable for the diathesis and disposition of an individual (individual organism).

Figure 1:
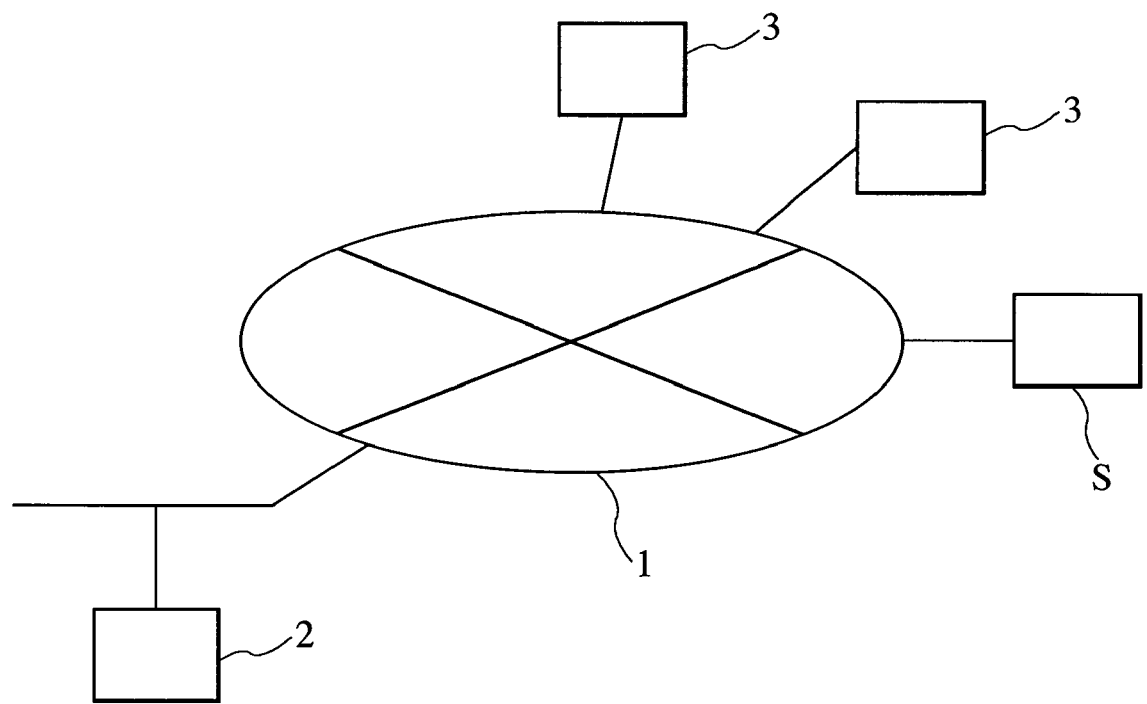
FIG. 1 is a schematic diagram illustrating the configuration of an information processing system according to the present invention.

As shown in FIG. 1, the information processing system comprises a communication network 1 such as the Internet, a shared computer 2, which is connected to the communication network 1, a plurality of personal computers 3, which are connected to the communication network 1, and at least one decryption computer S, which is connected to the communication network 1. Data communication among the shared computer 2, personal computers 3, and decryption computer S is established via the communication network 1.

Figure 2:
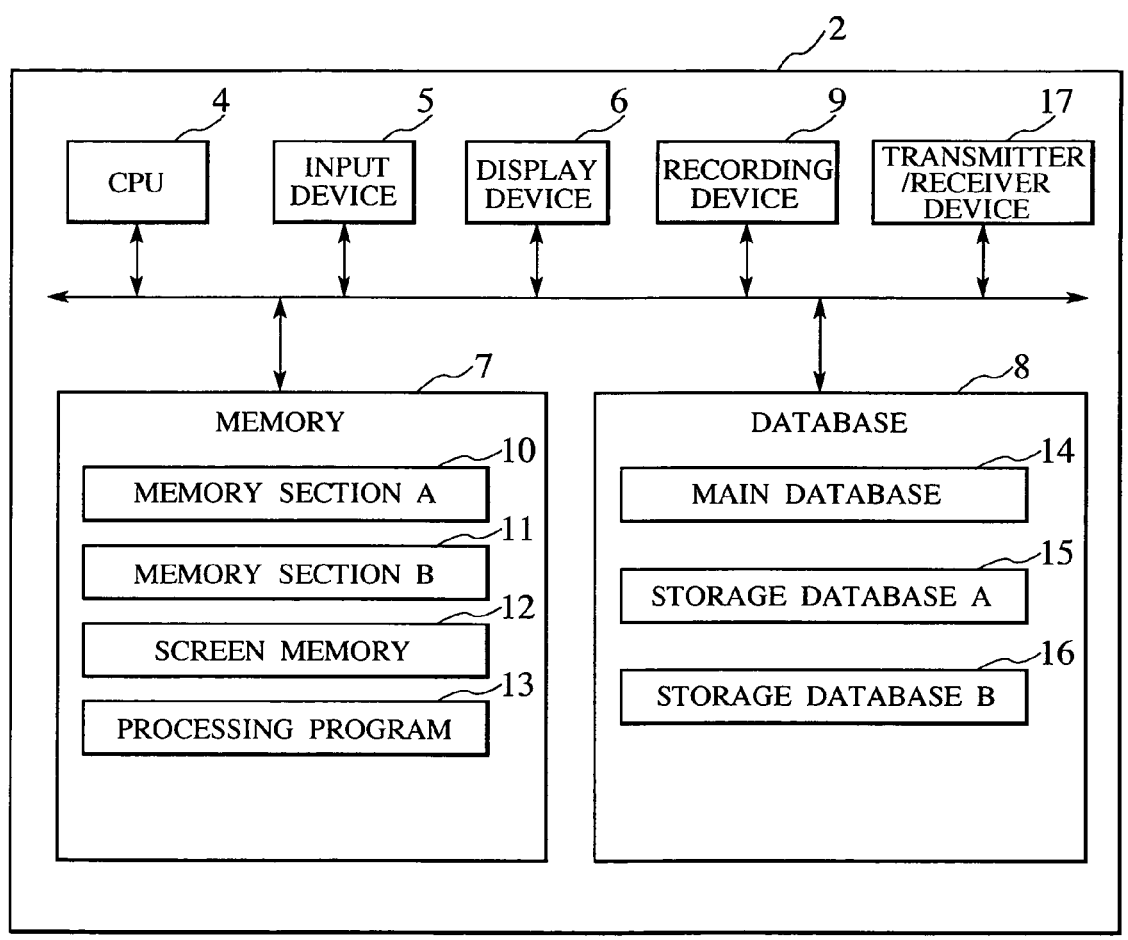
FIG. 2 is a schematic diagram illustrating the configuration of a shared computer.

As shown in FIG. 2, the shared computer 2 comprises a CPU 4 for providing overall control over the shared computer 2, a keyboard, mouse, or other input device 5 for entering information, program execution instructions, and the like, a display unit or other display device 6, a memory 7 for recording information such as temporary information and unrewritable information, a database 8 for storing various data, a recording device 9 for writing specified information into the memory 7 and database 8, and a transmitter/receiver device 17 for exchanging information with the personal computers 3 and decryption computer S via the communication network 1.

The memory 7 in the shared computer 2 comprises memory section A 10 and memory section B 11, which respectively record different types of information; a screen memory 12, which records image data to be displayed on the personal computers 3 and display device 6; and a processing program 13, which operates the information processing system. The memory 7 in the shared computer 2 may not always include the screen memory 12, processing program 13, or the like. Alternatively, the shared computer 2 may use an external storage device (not shown) that includes the screen memory 12, processing program 13, and the like and is connected to the shared computer 2 via the communication network 1.

The database 8 (storage device) in the shared computer 2 comprises a main database 14, which records polymorphism addresses, polymorphism patterns, and semantic information; storage database A 15, which stores the information recorded in memory section A 10; and storage database B 16, which stores the information recorded in memory section B 11. As shown in FIG. 3, the main database 14 records the association among polymorphism addresses, polymorphism patterns applicable to each of the polymorphism addresses, and semantic information implied by each of the polymorphism patterns. Further, the main database 14 may record semantic information that is implied by a combination of polymorphism patterns at a plurality of polymorphism addresses (e.g., haplotype).

The term "polymorphism address (positional information)" indicates, at least, a position in a nucleotide sequence where a polymorphism is present. In general, the term "polymorphism" includes a so-called SNP (single nucleotide polymorphism), RFLP (restriction fragment length of polymorphism), VNTR (variable number of tandem repeat), microsatellite, and others. However, the term "polymorphism" used herein is not limited to the above and also includes a variation in nucleotides and nucleotide sequences existing only at a frequency of less than 1% in an individual species. Therefore, the "polymorphism address" also includes a position in a nucleotide sequence, which indicates a variation of a nucleotide and nucleotide sequences existing only at a frequency of less than 1% in an individual species. More specifically, the "polymorphism address" indicates a position representing a polymorphism or the like by a combination of numerical values, letters, symbols, and the like. The polymorphism address is not particularly limited but may be represented, for instance, by a combination of a chromosome number, a symbol indicating a gene having a polymorphism therein, and a numerical value indicating the position of a polymorphism in the gene. Alternatively, it may be a combination of a symbol indicating a gene having a polymorphism therein and a numerical value indicating the position of a polymorphism in the gene.

Further, the "polymorphism address" may be a notation peculiar to a polymorphism that is imparted to each polymorphism. When the notation peculiar to a polymorphism is used as a polymorphism address, the polymorphism address does not directly indicate a position in a nucleotide sequence; however, the position can be indirectly found by the notation peculiar to the polymorphism. Therefore, the "polymorphism address" includes the notation peculiar to the polymorphism.

The term "polymorphism pattern (nucleotide sequence-related information) refers to the information on nucleotide sequences that differ among individual organisms, and contains, at least, a pattern of nucleotides or nucleotide sequences in a polymorphism. In addition, the "polymorphism pattern" is not limited to a polymorphism and includes a pattern of nucleotides and nucleotide sequences existing only at a frequency of less than 1% in an individual species. For example, in a polymorphism address that is known to take A or G, the "polymorphism pattern" is represented either by "A" or "G".

The "polymorphism pattern" may also represent a heterozygote or homozygote in a homologous chromosome. In this instance, the "polymorphism pattern" can be represented by "AA", "GG", or "AG" in the polymorphism address that is known to take A or G.

Further, the "polymorphism pattern" may indirectly represent a possible pattern at a predetermined polymorphism address instead of direct representation of patterns. For example, in the polymorphism address that is known to take A or G, the "polymorphism pattern" may be represented by "allele 1" when the polymorphism address takes "A" or "allele 2" when the polymorphism address takes "G". If the "polymorphism pattern" can be expressed as "AA", "GG", or "AG" as described above, the polymorphism pattern" may be represented by "α" when it can be expressed as "AA", may be represented by "β" when it can be expressed as "GG", or may be represented by "γ" when it can be expressed as "AG".

If the polymorphism is a microsatellite, the "polymorphism pattern" may be represented by a numerical value indicating "the number of repetitions". If the polymorphism is of the insertion/deletion type, the "polymorphism pattern" may be represented by a symbol indicating "presence/absence". Further, the "polymorphism patterns" at various polymorphism addresses may be represented, for instance, by "polymorphism 1", "polymorphism 2", and "polymorphism 3" in accordance with a specified regulation or agreement. For example, the polymorphism patterns at various polymorphism addresses may be represented by "polymorphism 1", "polymorphism 2", and "polymorphism 3" in order from the highest frequency of polymorphism pattern existence to the lowest. In this instance, the contents of "polymorphism 1" at various polymorphism addresses are not always the same. In other words, "polymorphism 1" at one polymorphism address represents, for instance, "AA", which denotes the highest possible frequency, whereas "polymorphism 1" at another polymorphism address represents "GG", which denotes the highest possible frequency.

The term "semantic information" used herein refers to information associated with a "polymorphism pattern". For example, it refers to various information arising out of "polymorphism pattern" differences, including the responsiveness to medicaments, side effects caused by medicaments, a risk of diseases and disorders, diatheses and dispositions, lifestyle advices based on diatheses and dispositions, and interaction among proteins. As the "semantic information", various information arising out of "polymorphism pattern" differences may be directly indicated or symbols and the like may be used to indirectly indicate such information. The "semantic information" is a type of information that is corrected and increases in the number of types due to a progress in the researches on genomes and genes. It is therefore preferred that the semantic information be constantly updated. In other words, the semantic information increases or decreases in the cumulative amount and becomes more accurate when its database is updated using the results of researches on genomes and genes.

Information that is further induced from the "semantic information" is "information associated with the semantic information" although it is not directly associated with a "polymorphism pattern". If the "semantic information" is a risk of diseases, specific "medical examination items" are derived when the risk exceeds a given level. The specific "medical examination items" are the "information associated with the semantic information".

In the present embodiment, the semantic information is recorded in the main database 14 as "annotative information on polymorphism pattern" that is associated with at least a predetermined "polymorphism address" and "polymorphism pattern" as shown in FIG. 3. Also, the semantic information is associated, for instance, with a "polymorphism category" and "category (disease name)", which corresponds to a predetermined "polymorphism address". Consequently, when a predetermined "polymorphism address" is a predetermined "polymorphism pattern", a disease name type and the annotative information (semantic information) on the morbidity rate of a disease can be obtained. Therefore, the semantic information can also be associated with a combination of respective polymorphism patterns corresponding to a plurality of polymorphism addresses (e.g., haplotype). In other words, each combination of polymorphism patterns at a plurality of polymorphism addresses can be respectively associated with annotative information (semantic information) representing different morbidity rates for predefined diseases. In this case, when a plurality of polymorphism addresses are a combination of predetermined polymorphism patterns, the annotative information (semantic information) indicating the morbidity rate of a predefined disease can be obtained.

Further, the semantic information can also be associated with a "disclosure level", which is determined in accordance with a predefined standard. For example, the standard for "disclosure level" determination can be determined by taking into consideration unpredictable disbenefits and the like for individuals that would be caused by disclosure of semantic information, i.e., the morbidity rate of "category (disease name)". In particular, the shared computer 2 can set a "disclosure level" so as not to disclose the semantic information, the disclosure of which is inappropriate from the viewpoint of, for example, laws, regulations, behavioral norms, or a contract with the user. In this instance, the information processing system assures that annotative information indicating a morbidity rate associated with a "disclosure level" at which disclosure is not possible will not be disclosed to users. This can prevent the provision of semantic information which could result in unpredictable disbenefits for users or the disclosure of semantic information to parties other than the contract party.

The system may disclose semantic information having a predetermined "disclosure level" associated therewith to users when users approve of the disclosure of semantic information associated with a predetermined "disclosure level" by means of informed consent or the like.

The "disclosure level" can be set as one of three or more different levels, for example, "1, 2, 3 . . . " or "a, b, c . . . ". In this instance, the shared computer 2 can set a disclosure level in accordance with the type of user, such as the user's age, the user's qualification, and whether or not a contract is concluded with the user. The user can select a disclosure level such that only annotative information indicating morbidity rates associated with the selected disclosure level or higher disclosure level (or associated with the disclosure levels lower than selected) is provided to the user in accordance with informed consent or the like.

Storage database B 16 in the database 8 can record, for example, data such as nucleotide sequence-related information that is the genetic information about an individual requester utilizing the system. Storage database A 15 can record, for example, data such as information identifying a requester utilizing the system. When storage database A 15 and storage database B 16 are used in this manner to respectively record the genetic information about a requester and the data identifying the requester, it is difficult to associate the genetic information about a requester with the data identifying the requester.

The shared computer 2 is not limited to one having the database 8 therein, and it may have an external database (not shown) that is connected to the shared computer 2 via the communication network 1. The shared computer 2 may have a plurality of databases 8 therein or may have an internal database 8 and an external database connected to the shared computer 2 via the communication network 1.

Figure 4:
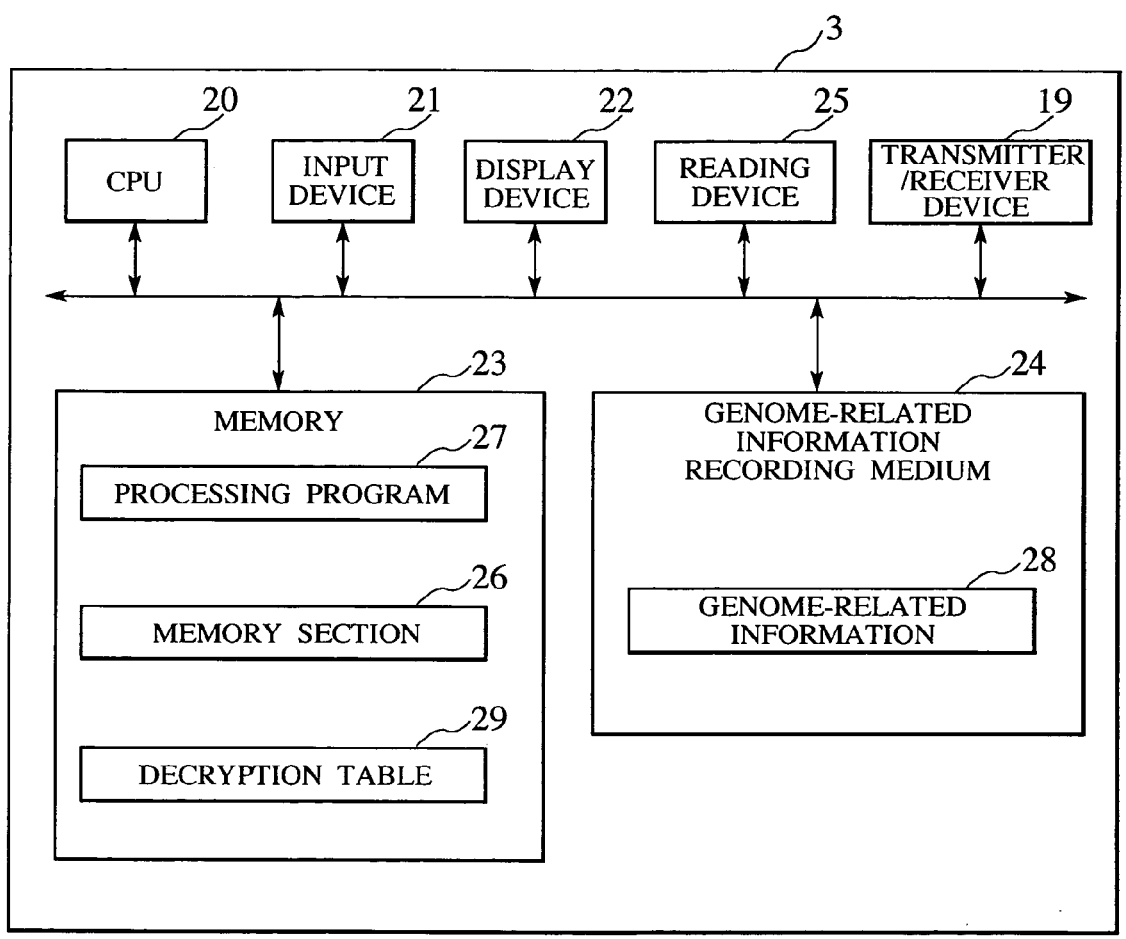
FIG. 4 is a schematic diagram illustrating the configuration of a personal computer.

As shown in FIG. 4, each personal computer 3 comprises a CPU 20 that provides overall control over the operation of the personal computer 3, a keyboard, mouse, or other input device 21 that is capable of entering information and program execution instructions, a display device 22 such as a display unit; a memory 23 for recording temporary information and rewritable information, and other information, a reading device 25 for reading data from a genome-related information recording medium 24, and a transmitter/receiver device 19 for exchanging information with the shared computer 2 and decryption computer S via the communication network 1. The personal computer 3 is not limited to a common computer. It may take any form such as a cellular phone, personal digital assistance, or other mobile communication tool.

The memory 23 in the personal computer 3 includes a memory section 26 for recording, for instance, the information derived from a genome-related information recording medium 24, and a decryption table 29, which will be described later in detail. A processing program 27 for operating the information processing system is recorded in the memory 23.

The genome-related information recording medium 24 records genome-related information 28 about an individual. For example, the genome-related information recording medium 24 may be a magnetic recording medium such as a magnetic disk or a magnetic card, an optical recording medium employing a magneto-optic recording technology or phase-change recording technology, or a semiconductor memory. This genome-related information recording medium 24 may be in any form such as a card, disk, stick, tape, or drum. Further, this genome-related information recording medium 24 may be used to record the genome-related information 28 about a single individual (an individual organism) or record a plurality of sets of genome-related information 28 about a plurality of individuals (individual organisms).

The genome-related information 28 stored on the genome-related information recording medium 24 is a "polymorphism address" and an "encrypted polymorphism pattern (encrypted nucleotide sequence-related information)", which is obtained by encrypting a "polymorphism pattern" at a predetermined polymorphism address that is acquired as a result of analysis of an individual's (individual organism's) nucleotide sequence. The genome-related information 28 contains an "encrypted polymorphism pattern". Therefore, the information derived from an individual's genomic DNA is not directly recorded. Further, the genome-related information 28 may contain various information, including an anamnesis, personal characteristics, clinical chart recordings, and medical examination results.

Various items of genome-related information 28 are recorded on the genome-related information recording medium 24. As shown in FIG. 5, the genome-related information recording medium 24 records the individual's number "Gno." (G number) peculiar to the genome-related information 28 as well as the individual's personal information, such as a birth date, as data I; polymorphism addresses and encrypted polymorphism patterns as data II; an anamnesis as data III; personal characteristics as data IV; and the individual's clinical chart recordings and other relevant information as data V. In other words, the genome-related information 28 comprises data I, data II, data III, data IV, and data V. Data I and data II contain essential information, whereas data III, data IV, and data V comprise supplementary information.

In the present embodiment, the memory 23 stores a "decryption table" 29, which uses random numbers to decrypt "encrypted polymorphism patterns". As shown in FIG. 6, the decryption table 29 is used to define the association between "random numbers" for polymorphism pattern encryption and "encrypted polymorphism patterns" encrypted by the random numbers. The "random numbers" are arranged in row direction, whereas the "encrypted polymorphism patterns" are arranged in column direction. Therefore, the "decryption table" 29 makes it possible to obtain an original polymorphism pattern by decrypting a specified "encrypted polymorphism pattern" with a "random number" used for encryption.

If the "polymorphism pattern" is a microsatellite or the like, for example, the "encrypted polymorphism pattern" can be represented by a numerical value that is obtained by adding a "random number" to a numerical value representing the "polymorphism pattern". When the "encrypted polymorphism pattern" is to be decrypted in this instance, a selected "random number", for example, is subtracted from the numerical value representing the "encrypted polymorphism pattern". In this manner, the microsatellite or other similar "encrypted polymorphism pattern" can be decrypted to obtain the original polymorphism pattern.

The "decryption table" 29 is not limited to the one that is recorded in the memory 23. It may be recorded on a genome-related information recording medium 24 or recorded in an external storage device that is accessible via the communication network 1.

When a "polymorphism pattern", which is obtained as a result of genomic DNA analysis, is to be encrypted, a commonly known encryption method may be applied as needed instead of using the above method, which is based on "random number" use. No matter what encryption method is used, the original polymorphism pattern can be obtained by decrypting an encrypted polymorphism pattern with a cryptographic key that has been used for polymorphism pattern encryption. The term "cryptographic key" generically refers to a key that includes at least a random number and is used for encryption and decryption.

The genome-related information 28 is recorded in such a manner that the "polymorphism address" corresponding to a position within a nucleotide sequence is linked with an "encrypted polymorphism pattern" at the polymorphism address. For data II, supplementary information about a specified polymorphism address may be recorded as a "comment" and linked with a "polymorphism address". All the nucleotide sequences of a specified individual organism may be recorded as data II. Even when all the nucleotide sequences are recorded as data II, data II contains "polymorphism addresses" and "encrypted polymorphism patterns".

According to the present invention, the personal computers 3 and genome-related information recording medium 24 are not limited to the configuration shown in FIGS. 4 and 5 respectively. In an alternative configuration, the genome-related information recording medium may include a memory section containing a processing program, and the personal computers may run the processing program with the genome-related information recording medium set in position. In this instance, the personal computers can operate in accordance with the processing program that is recorded in the memory section of the genome-related information recording medium.

Figure 7:
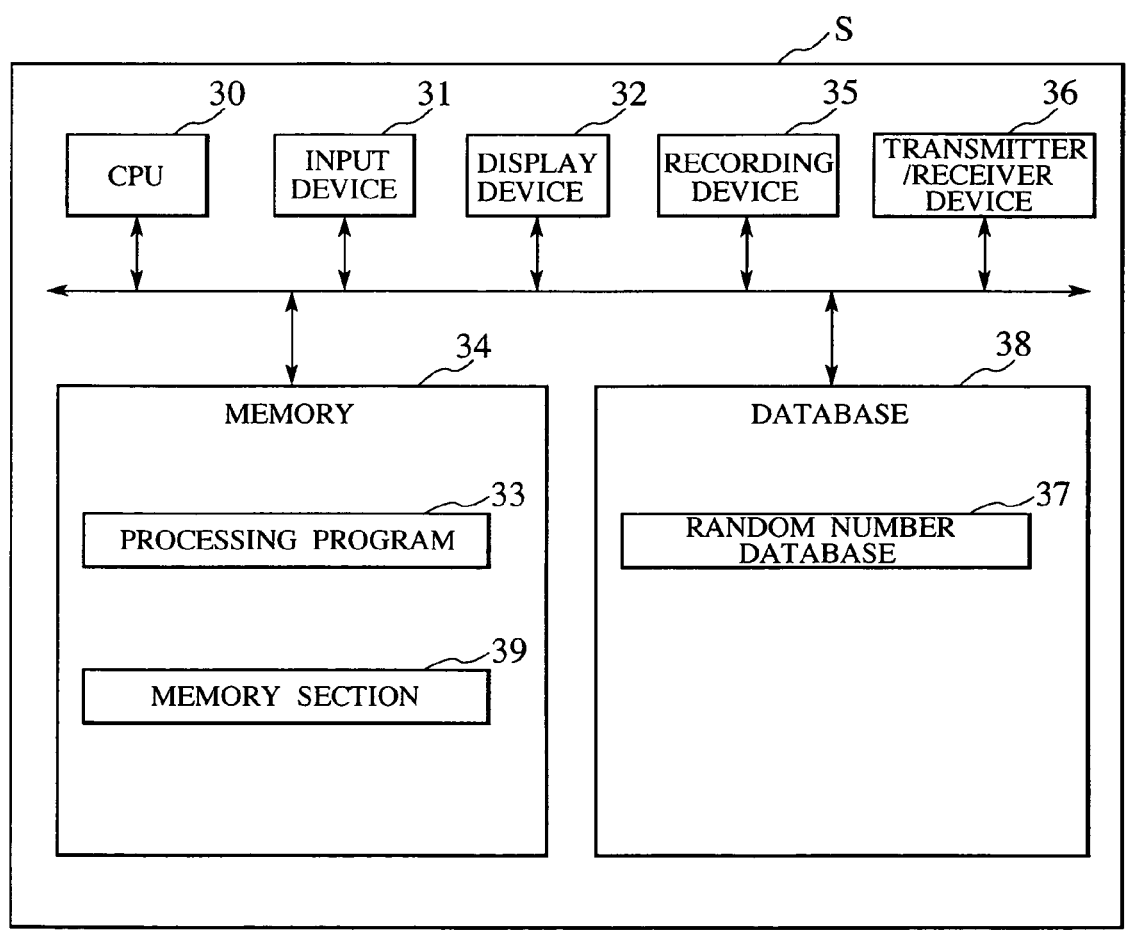
FIG. 7 is a schematic diagram illustrating the configuration of a decryption computer.

As shown in FIG. 7, the decryption computer S comprises a CPU 30 for providing overall control over the decryption computer S, a keyboard, mouse, or other input device 31 for entering information, program execution instructions, and the like, a display unit or other display device 32, a processing program 33, a memory 34 for recording information such as temporary information and rewritable information, a recording device 35, a transmitter/receiver device 36 for exchanging information with the shared computer 2 and personal computers 3 via the communication network 1, and a database 38 containing at least a random number database 37 (storage device for storing the association between positional information and cryptographic keys). The memory 34 for the decryption computer S includes a memory section 39 in which temporary information, rewritable information, and other information can be written for temporary storage. The decryption computer S is not limited to one having an internal database 38, and may be provided with an external database (not shown) that is connected to the decryption computer S via the communication network 1.

As shown in FIG. 8, the random number database 37 recorded in the database 38 is used, for instance, to record the "Gno."-specific association between polymorphism addresses and random numbers used for encrypting polymorphism patterns at the polymorphism addresses. In other words, the random number database 37 records a G number (Gno.) peculiar to the genome-related information recording medium 24 and the random numbers corresponding to a plurality of polymorphism addresses for the G number (Gno.)

The random numbers are randomly selected for specified polymorphism addresses, and used to encrypt polymorphism patterns at specified polymorphism addresses. For example, the random number selected for a specified polymorphism address can encrypt a polymorphism pattern at the polymorphism address in accordance with an encryption table 40 shown in FIG. 9. The encryption table 40 is used to encrypt a specified polymorphism pattern to obtain an encrypted polymorphism pattern. Encrypted polymorphism patterns can be derived from polymorphism patterns and random numbers. If, for instance, a microsatellite or other similar polymorphism pattern is employed, it is represented by a numerical value that indicates the number of repetitions. When the polymorphism pattern is to be encrypted in such an instance, the selected random number, for example, is added to the above numerical value. In this manner, it is possible to encrypt the polymorphism pattern, which comprises a numerical value indicating the number of repetitions.

Figure 10:
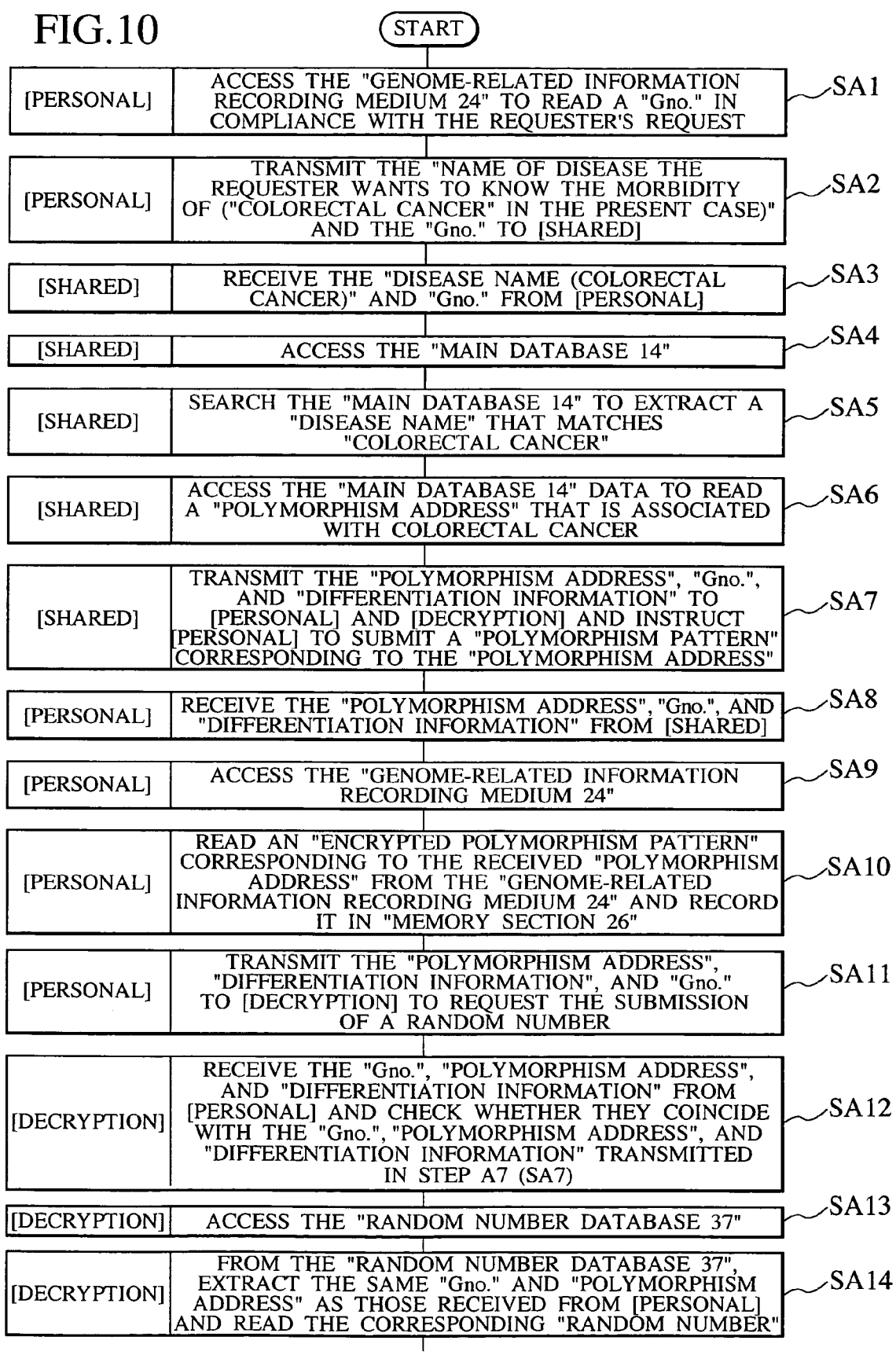
FIG. 10 is a flowchart illustrating processing steps that are performed by a shared computer, personal computer, and decryption computer in a system providing morbidity rates of predefined diseases.
Figure 11:
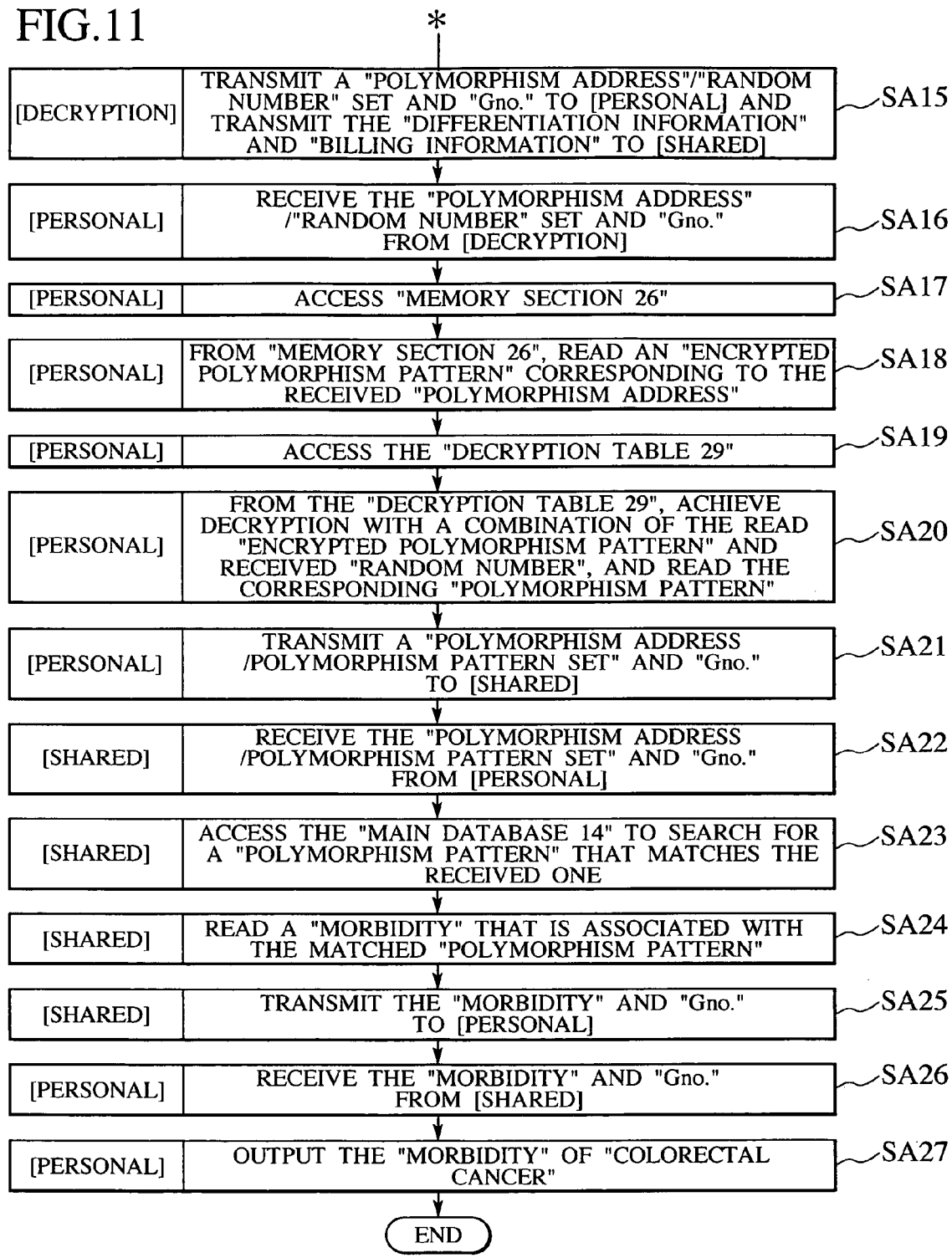
FIG. 11 is a flowchart that is a continuation of FIG. 10, which illustrates processing steps that are performed by a shared computer, personal computer, and decryption computer in a system providing morbidity rates of predefined diseases.
Figure 12:
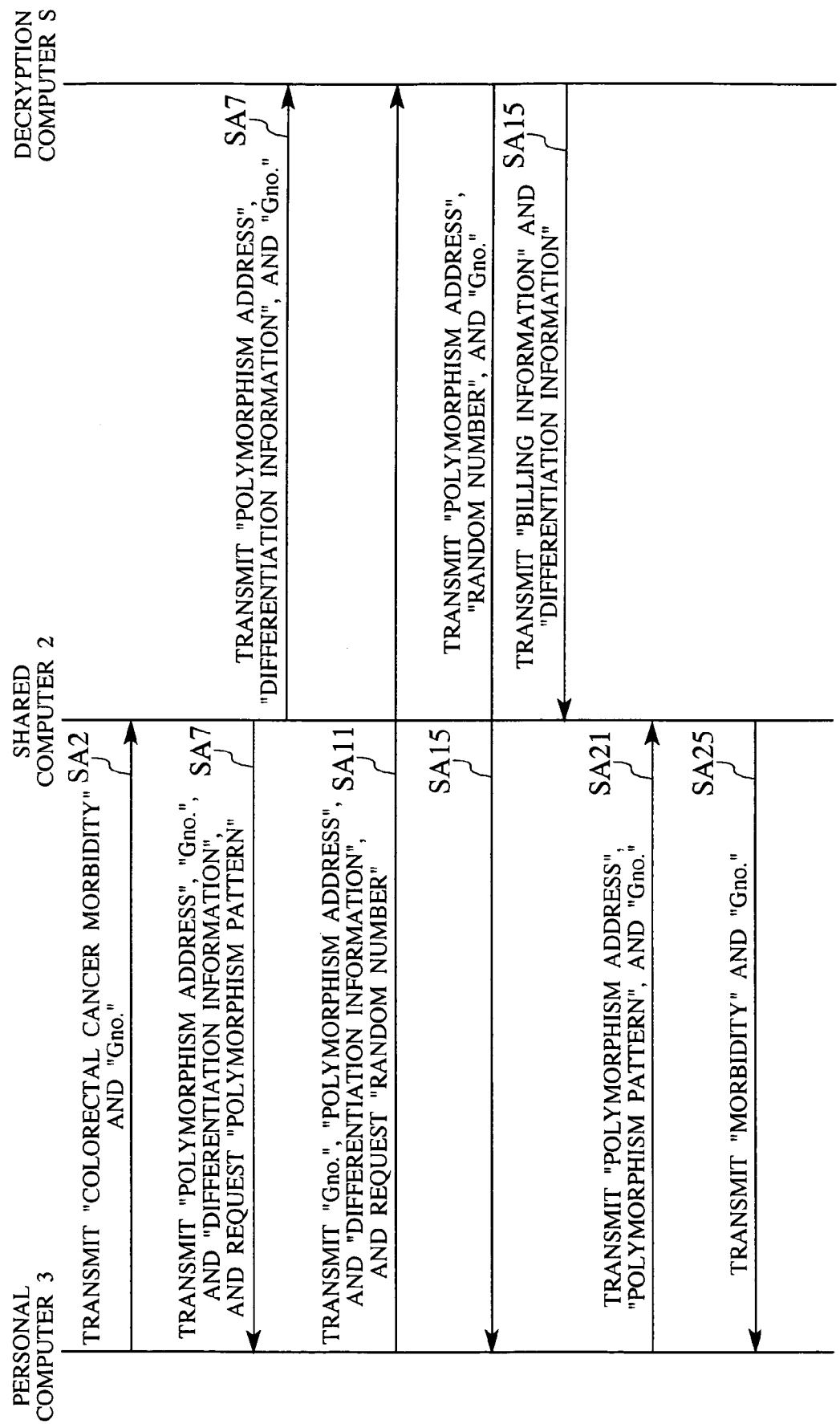
FIG. 12 is a sequence diagram illustrating processing steps (shown in FIGS. 10 and 11) that are performed by a shared computer, personal computer, and decryption computer in a system providing morbidity rates of predefined diseases.

In the information processing system configured as described above, the processing program 13 recorded in the memory 7 of the shared computer 2, the processing program 27 recorded in the memory 23 of the personal computer 3, and the processing program 33 recorded in the memory 34 of the decryption computer S perform information processing operations in accordance, for instance, with the flowchart in FIGS. 10 and 11. In the flowchart shown in FIGS. 10 and 11, the processing steps marked "[Shared]" are performed by the shared computer 2; the processing steps marked "[Personal]" are performed by the personal computer 3; and the processing steps marked "[Decryption]" are performed by the decryption computer S. The sequence diagram shown in FIG. 12 illustrates an information process that is performed in accordance with the flowchart in FIGS. 10 and 11.

The information processing system is a system in which an individual who possesses a genome-related information recording medium 24 accesses the shared computer 2 via the communication network 1 by using a personal computer 3 and utilizes semantic information recorded in the main database 14 in the shared computer 2. The information processing system may be a system in which individuals access a genome-related information recording medium 24 by using a genome-related information recording medium 24 that contains the genome-related information 28 concerning a plurality of individuals.

When the genome-related information recording medium 24 is to be produced, a clinical examination company or other genome analysis organization is first used to analyze an individual's genomic DNA. A polymorphism pattern, which is obtained as a result of analysis, is then encrypted by the analysis organization or an organization other than decryption computer S. In encryption, it is possible to select a random number for a specified polymorphism address and use an encryption table 40, which looks like FIG. 9, to encrypt a polymorphism pattern at the polymorphism address. More specifically, a plurality of combinations of polymorphism addresses and polymorphism patterns derived from the genomic DNA analysis of an individual are first used to select a random number for each polymorphism address. The random numbers may be randomly selected for a plurality of polymorphism addresses or selected in accordance with a predetermined rule.

Next, the selected random numbers and encryption table 40 are used to encrypt the polymorphism patterns derived from the analysis at the polymorphism addresses. The combinations of the polymorphism addresses and polymorphism patterns derived from the genomic DNA analysis of an individual can then be turned into the combinations of the polymorphism addresses and encrypted polymorphism patterns. If encryption is performed by the analysis organization, the database or other similar collection containing the combinations of the polymorphism addresses and polymorphism patterns derived from the analysis is accessed via the organization's intranet or the like to encrypt the polymorphism patterns contained in the database or other similar collection. Further, if encryption is performed by the analysis organization, the polymorphism patterns may be encrypted with a machine used for the analysis after the polymorphism addresses and polymorphism patterns are derived from the analysis.

Next, the genome-related information recording medium 24 can be produced by recording the association between polymorphism addresses and encrypted polymorphism patterns and setting a G number ("Gno.") unique to an individual. In this instance, the random numbers selected for all the polymorphism addresses are associated with the G number ("Gno.") and recorded in the random number database 37 in the decryption computer S.

When the genome-related information recording medium 24 is to be produced, the genomic DNA of an individual may be analyzed by the above analysis organization to encrypt the resulting polymorphism pattern with an organization or the like having the decryption computer S. In this instance, the organization or the like having the decryption computer S has an encryption table 40 shown in FIG. 9.

The encryption table 40 may be changed for each change in the G number ("Gno."). In such an instance, the decryption table 29 varies with the G number ("Gno.") to correspond to the encryption table 40.

When a polymorphism pattern derived from the genomic DNA analysis of an individual is to be encrypted by an organization having the decryption computer S, for example, the encryption table 40, which is possessed by the decryption computer S, is used. In this instance, the organization may acquire the analysis result from a terminal of the above analysis organization via the communication network 1 and use the acquired analysis result.

The individual who uses the information processing system is a person who possesses the genome-related information recording medium 24 that contains an encrypted polymorphism pattern made in the way described above. The individual who uses the information processing system (hereinafter referred to as the requester) first performs step A1 (SA1). In step A1 (SA1), the requester starts processing program 27, which is recorded in the memory 23, to drive the reading device 25 for a personal computer 3, access the genome-related information recording medium 24, and read a G number ("Gno.") that is recorded on the genome-related information recording medium 24 as data I. The read G number ("Gno.") is then stored in a memory section 26.

It is preferred that a password or biological information such as a fingerprint, for example, be used prior to step A1 for authentication in order to check whether or not the genome-related information recording medium 24 belongs to the requester.

In step A2 (SA2), the information that the requester wishes to receive, for example, the "colorectal cancer morbidity" (request information), is entered into the personal computer 3 in accordance with an on-screen image that is displayed on the display device 22 by processing program 27, and the personal computer 3 transmits the "colorectal cancer morbidity" and "Gno." to the shared computer 2 via the communication network 1. Alternatively, the personal computer 3 writes the "colorectal cancer morbidity" and "Gno." into the shared computer 2 via the communication network 1.

In step A3 (SA3), the shared computer 2 receives the "colorectal cancer morbidity" and "Gno." (G number). The received "colorectal cancer morbidity" and "Gno." are then stored in memory section A 10 as request information.

Step A4 (SA4) is then performed upon receipt of the request information. In this step, processing program 13, which is stored in memory 7, is started to access the main database 14. Processing program 13 is used for processing in the shared computer 2.

In step A5 (SA5), the category (disease name) recordings in the main database 14 are searched to extract a category (disease name) that matches the requested "colorectal cancer morbidity" (colorectal cancer).

In step A6 (SA6), the data stored in the main database 14 is searched to read a "polymorphism address" that is associated with the "category (disease name)", which matches the "colorectal cancer morbidity". Memory section A 10 then stores the read "polymorphism address" as the positional information associated with the request information. As a result, memory section A 10 records the "colorectal cancer morbidity" (colorectal cancer) and "polymorphism address" for a specific "Gno.".

In step A7 (SA7), the "Gno." and "polymorphism address", which are recorded in memory section A 10, and "differentiation information", are transmitted to the personal computer 3 and decryption computer S, and command information instructing to present the "polymorphism pattern" corresponding to the "polymorphism address" is transmitted to the personal computer 3. The "differentiation information" (information about a direct billing destination or an indirect billing destination) is specific to the shared computer 2 and can be used to identify the shared computer 2. The "differentiation information" is used for shared computer billing, which will be described later. It is therefore preferred that transaction-specific information, which provides transaction identification, be added as part of the "differentiation information".

Step A7 may also be performed to transmit the information about the address of the decryption computer S to the personal computer 3. In such an instance, the personal computer 3 may be instructed, depending on the type of request information, to submit supplementary information such as an anamnesis and personal characteristics.

In step A8 (SA8), the personal computer 3 receives the "Gno.", "polymorphism address", "differentiation information", and command information, which are transmitted from the shared computer 2. The received "Gno.", "polymorphism address", and "differentiation information" are then recorded in memory section 26. Further, if the information about the address of the decryption computer S is received, it is also recorded in memory section 26.

In step A9 (SA9), the data II recording on the genome-related information recording medium 24 is accessed in compliance with the received command information. In step A10

(SA10), the data II recording on the genome-related information recording medium 24 is searched in compliance with processing program 27 to read an "encrypted polymorphism pattern" that corresponds to the command-designated (received) polymorphism address, and then the association between the polymorphism address and encrypted polymorphism pattern is recorded in memory section 26. In this instance, it is preferred that data I be accessed to check whether or not the "Gno." received in step A8 is correct. In step A10, the supplementary information recorded as data III, data IV, and data V may also be read in addition to the encrypted polymorphism pattern, and if necessary, recorded in memory section 26.

In step A11 (SA11), the "polymorphism address", "differentiation information", and "Gno.", which were received in step A8, are transmitted to the decryption computer S via the communication network 1. In other words, step A11 is performed so that the personal computer 3 requests the decryption computer S to present a random number corresponding to the "polymorphism address" received in step A8. The personal computer 3 may access the decryption computer S in accordance with the information about the address of the decryption computer S, which was received in step A8.

In step A12 (SA12), the decryption computer S receives the "Gno.", "polymorphism address", and "differentiation information" from the personal computer 3. Step A12 is performed so that the decryption computer S checks whether or not the received "Gno.", "polymorphism address", and "differentiation information" coincide with the "Gno.", "polymorphism address", and "differentiation information" that are transmitted in step A7 from the shared computer 2 to the decryption computer S.

In step A13 (SA13), the processing program 33 for the decryption computer S operates to access the random number database 37 if it is judged that the "Gno.", "polymorphism address", and "differentiation information" received in step A12 coincide with the "Gno.", "polymorphism address", and "differentiation information" transmitted in step A7 from the shared computer 2. If it is judged that the "Gno.", "polymorphism address", and "differentiation information" received in step A12 do not coincide with the "Gno.", "polymorphism address", and "differentiation information" transmitted in step A7 from the shared computer 2, processing step A13 is aborted.

In step A14 (SA14), the random numbers bound by the "Gno." received in step A12 are checked to locate a random number that corresponds to the "polymorphism address" received in step A12, and then the located random number is read from the random number database 37. The read random number is then associated with the "Gno.", "polymorphism address", and "differentiation information" received in step A12 and recorded in memory section 39.

In step A15 (SA15), the "Gno.", "polymorphism address", and "random number" recorded in memory section 39 are associated with each other and transmitted from the decryption computer S to the personal computer 3 via the communication network 1. In this step, the decryption computer S also transmits the "differentiation information" and "billing information" to the shared computer 2 via the communication network 1. The "billing information" is the information about the amount of money that is calculated from the random numbers supplied from the decryption computer S to the personal computer 3. The "billing information" may be information that corresponds to the number of random numbers supplied from the decryption computer S to the personal computer 3, may be weighted information that is obtained in accordance with the category (degree of importance of semantic information at the polymorphism address) of the polymorphism address associated with the random numbers supplied, may be information that corresponds to the number of random numbers and the category of the polymorphism address (degree of importance of semantic information at the polymorphism address), or may be information that corresponds to the number of transactions (supply of random numbers). When the "differentiation information" and "billing information" are transmitted to the shared computer 2, the shared computer 2 grasps the information about billing for a specific transaction. In other words, step A15 is performed to bill the shared computer 2, instead of the personal computer 3, for the random numbers that are supplied from the decryption computer S to the personal computer 3. The "differentiation information" and "billing information" may be transmitted to, for instance, a credit company instead of being directly transmitted to the shared computer 2 for the purpose of indirectly billing the shared computer 2 for random number supply. When the "differentiation information" and "billing information" are directly transmitted to the shared computer 2, the differentiation information is the "information about a direct billing destination". When, for instance, the differentiation information is transmitted to a credit company, it is the "information about an indirect billing destination".

In step A16 (SA16), the "Gno.", "polymorphism address", and "random number" transmitted from the decryption computer S are received by the personal computer 3. The received "Gno.", "polymorphism address", and "random number" are stored in memory section 26.

In step A17 (SA17), the processing program 27 for the personal computer 3 operates to access memory section 26. In step A18 (SA18), the "encrypted polymorphism pattern" corresponding to the "polymorphism address" received in step A16 is read from memory section 26.

In step A19 (SA19), the processing program 27 for the personal computer 3 operates to access the decryption table 29. In step A20 (SA20), the "random number" received in step A16 is used in conjunction with the "encrypted polymorphism pattern" read in step A18 to decrypt the "encrypted polymorphism pattern" in accordance with the decryption table 29 and obtain the original "polymorphism pattern". In other words, step A20 is performed to obtain the "polymorphism pattern" that corresponds to the "polymorphism address" contained in the command information. The obtained polymorphism pattern is associated with the corresponding "polymorphism address" and recorded in memory section 26.

In step A21 (SA21), the polymorphism pattern associated with the polymorphism address that is temporarily recorded in memory section 26 as well as the supplementary information that is recorded as needed are transmitted together with the "Gno." to the shared computer 2 via the communication network 1. In step A22 (SA22), the shared computer 2 receives the "Gno.", the polymorphism pattern associated with the polymorphism address, and the supplementary information that is recorded as needed, and the received polymorphism pattern is associated with the polymorphism address and recorded in memory section A 10.

In the present embodiment, step A7 is performed so that the shared computer 2 transmits command information to issue instructions for "polymorphism pattern" submission, and step A20 is performed so that the personal computer 3 acquires the polymorphism pattern the submission of which is dictated by the command information. However, the information processing system may alternatively be a system in which the command information is not transmitted in step A7. In such an alternative system, the personal computer 3 complies with processing program 27 in step A10 to search data II in accordance with the polymorphism address received in step A8 and read the encrypted polymorphism pattern corresponding to the polymorphism address received in step A8. Then, the personal computer 3 decrypts the encrypted polymorphism pattern in step A20, and outputs, in step A21, the polymorphism pattern corresponding to the polymorphism address received in step A8 to the shared computer 2. In this instance, too, the shared computer 2 can acquire, in step A22, the polymorphism pattern for the "polymorphism address" associated with the "category (disease name)" that matches the "colorectal cancer morbidity".

In step A23 (SA23), the main database 14 is accessed to search for an item that matches the received polymorphism address and polymorphism pattern. More specifically, the main database 14, which stores a plurality of polymorphism patterns for each polymorphism address, is searched to determine what polymorphism pattern matches the received polymorphism address and polymorphism pattern.

In step A24 (SA24), the colorectal cancer morbidity associated with a polymorphism pattern that matches the received polymorphism pattern is read in compliance with processing program 13. In other words, step A24 is performed to read the requester's colorectal cancer morbidity in accordance with the polymorphism address and the polymorphism pattern submitted by the requester. The read morbidity is associated with the "Gno." of the requester and stored in memory section A 10. In this instance, the colorectal cancer morbidity may be stored after being corrected by supplementary information or may be stored after the other information derived from supplementary information is associated with the "Gno." of the requester.

In step A25 (SA25), the requester's "Gno." and morbidity, which are stored in memory section A10, is transmitted as semantic information to the personal computer 3 via the communication network 1. In step A26 (SA26), the personal computer 3 receives the requester's "Gno." and morbidity (semantic information). The received semantic information is recorded in memory section 26.

Step A27 (SA27) is then performed in compliance with processing program 27 so that the display device 22 displays the colorectal cancer morbidity, which is derived from the semantic information recorded in memory section 26. Instead of steps A25 through A27, the shared computer 2 may read (produce) a semantic information display screen in compliance with processing program 13 and display the read information on the display device 22 for the personal computer 3 via the communication network 1. In this instance, too, it is assumed that the shared computer 2 transmits semantic information to the personal computer 3. The requester is then enabled to obtain the colorectal cancer morbidity by using the genome-related information 28 that is recorded on the genome-related information recording medium 24.

As described above, the information processing system allows an individual to use the semantic information recorded in the main database 14 via a polymorphism address by using the genome-related information recording medium 24 on which the association between an encrypted polymorphism pattern and polymorphism address is recorded. The individuals who use the information processing system do not have to record semantic information on the genome-related information recording medium 24, and can obtain various semantic information simply by possessing the genome-related information 28 that contains the association between a polymorphism address and encrypted polymorphism pattern.

In the information processing system, the polymorphism pattern recorded on the genome-related information recording medium 24 is encrypted particularly. Therefore, even when the genome-related information recording medium 24 is stolen or otherwise lost, the polymorphism pattern cannot be deciphered. The polymorphism pattern is fundamentally specific to an individual and highly confidential. It is therefore pointed out that the polymorphism pattern must be handled with great care. The information processing system can properly protect the information about highly confidential polymorphism patterns and properly prevent an illegal use by a third party. Particularly, if authentication is performed prior to step A1, illegal uses can be prevented with increased certainty because spoofing and other illegal activities can be avoided.

Further, the information processing system decrypts only the "encrypted polymorphism pattern" corresponding to the "polymorphism address" that is contained in the command information fed from the shared computer 2. In other words, the information processing system does not decrypt all the "encrypted polymorphism patterns" recorded on the genome-related information recording medium 24. Therefore, even if the personal computer 3 is illegally accessed or otherwise jeopardized after step A16, the possibility of polymorphism pattern leakage can be minimized.

Meanwhile, the information processing system requests, in step A11, the decryption computer S to present a "random number" that is associated with a polymorphism address contained in the command information for the purpose of decrypting an "encrypted polymorphism pattern" corresponding to the polymorphism address contained in the command information. However, the present invention is not limited to such a system and may alternatively be a system in which the requester makes a request to the decryption computer S for all the "random numbers" associated with polymorphism addresses without regard to the polymorphism address contained in the command information.

In the above alternative system, the requester does not need to transmit the "polymorphism address" contained in the command information to the decryption computer S. If the "polymorphism address" contained in the command information is transmitted to the decryption computer S via the communication network 1, the type of information requested by the requester might be identified in the event of illegal access or other similar contingency. In this instance, however, all the "random numbers" associated with polymorphism addresses are requested. Therefore, when the decryption computer S and personal computer 3 exchange information, the type of information requested by the requester cannot possibly be identified even in the event of illegal access or other similar contingency.

In the above instance, it is preferred that the personal computer 3 achieve decryption by using only the "random number" related to the "polymorphism address" contained in the command information although there are various other "random numbers" associated with the polymorphism addresses that are obtained from the decryption computer S. In other words, it is preferred that only the "polymorphism pattern" transmitted from the personal computer 3 to the shared computer S be decrypted.

In the information processing system, the decryption computer S causes the shared computer 2 to pay the information supply fee for random number supply concerning a predetermined polymorphism address. In other words, when the decryption computer S supplies a random number to the personal computer 3, the information processing system assumes that a contract can be concluded between the decryption computer S and shared computer 2. When the contract is concluded, the shared computer 2 is obliged to pay for random number supply. In the information processing system, therefore, the decryption computer S does not collect the information supply fee for an individual transaction (random number supply) from an unspecified number of personal computers 3 (information supply destinations). Instead, the decryption computer S collects the entire fee from the shared computer 2, which is a provider. This results in an increase in clerical work efficiency. Further, the shared computer 2, which is a provider, can add the information supply fee for an individual transaction (random number supply) to the price of the "Supplying the information about the morbidity of a specified disease" service. Therefore, the users of the personal computers 3 do not feel that they are paying the information supply fee for random number supply. The information processing system may allow the decryption computer S to directly bill the personal computers 3 for information supply by permitting the decryption computer S to transmit "billing information" to the personal computers 3 in step A15.

In step A15 of the flowchart used in the above description, the decryption computer S transmits the "billing information" to the shared computer 2. Alternatively, however, the decryption computer S may transmit the "billing information" to the shared computer 2 at any time after the random numbers are supplied from the decryption computer S to the personal computers 3. Further, the "billing information" may be transmitted upon each transaction (random number supply). Another alternative is to record in a memory or the like the "billing information" about a plurality of transactions for a predetermined period of time, conduct a batch scan, statistically process the resulting information, and periodically transmit the processed information. The billed amount may also be varied in accordance with predefined rules (e.g., by reducing the amount by a predetermined percentage if a predetermined random number supply count is exceeded) and the statistically processed information (e.g., the cumulative number of random number supplies during a predetermined period of time). Further, the billed amount may be varied (e.g., by reducing the amount billed for random number supply for polymorphism addresses for which a predetermined count is exceeded) for each polymorphism address in accordance with predefined rules and the statistically processed information (e.g., the cumulative number of random number supplies for each polymorphism address during a predetermined period of time).

When the billed amount is varied for each polymorphism address in accordance with predefined rules, the "billing information" to be transmitted in step A15 may be the sum of billed amounts for each polymorphism address or may be not the sum but a list of billed amounts for each polymorphism address.

In the information processing system, the decryption computer S can properly bill the shared computer 2 because it verifies the reception of the "billing information" in step A12 and transmits a random number in step A15.

In step A7, the information processing system may set in accordance with predefined rules an "anonymous polymorphism address" corresponding to a "polymorphism address" that is contained in the command information, and transmit to a personal computer 3 the command information containing the "anonymous polymorphism address" that is associated with the "polymorphism address. The "anonymous polymorphism address" differs from a polymorphism address that directly shows a polymorphism position within a genomic DNA. It is linked to the "polymorphism address" read in step A6, and does not directly represent a polymorphism pattern position within a genomic DNA.

In the above instance, the requester transmits a "Gno." as well as the association between the "anonymous polymorphism address" and "polymorphism pattern" to the shared computer 2 via the communication network 1 in step A21. In this case, the personal computer 3 does not transmit a polymorphism address, which directly represents a polymorphism pattern position within a genomic DNA, or a polymorphism pattern at that polymorphism address. Since the anonymous polymorphism address does not directly represent a polymorphism pattern position within a genomic DNA, the polymorphism pattern position within the genomic DNA cannot be determined even if the information transmitted in step A21 leaks to the outside due to a contingency. In other words, if an anonymous polymorphism address is used in the information processing system, personal information leakage can be prevented without using an advanced encryption technology. In the information processing system, therefore, the information transmitted in step A21 cannot possibly be used by anyone else. Thus, increased secrecy of personal information results.

In step A11, the requester may also set an "anonymous polymorphism address" corresponding to a "polymorphism address" that is contained in the command information, and transmit to the decryption computer S the command information containing the "anonymous polymorphism address" that is associated with the "polymorphism address". In this instance, the decryption computer S transmits the "Gno.", "anonymous polymorphism address", and "random number" to the personal computer 3 in step A15. Therefore, even if the information leaks to the outside due to a contingency in step A15, the random number at a certain "polymorphism address" cannot be identified. It means that the use of an anonymous polymorphism address in the information processing system makes it possible to prevent cryptographic key leakage without using an advanced encryption technology. Consequently, the information transmitted by the information processing system in step A15 cannot be used by anyone else. Thus, increased secrecy of a cryptographic key results.

The information processing system is not limited to an information process in which the shared computer 2 supplies semantic information and/or the information related to the semantic information to the personal computer 3 in accordance with the flowchart shown in FIGS. 10 and 11 and the sequence diagram shown in FIG. 12. Alternatively, the information processing system may perform an information process in accordance with a sequence diagram shown in FIG. 13, 14, or 15.

Figure 13:
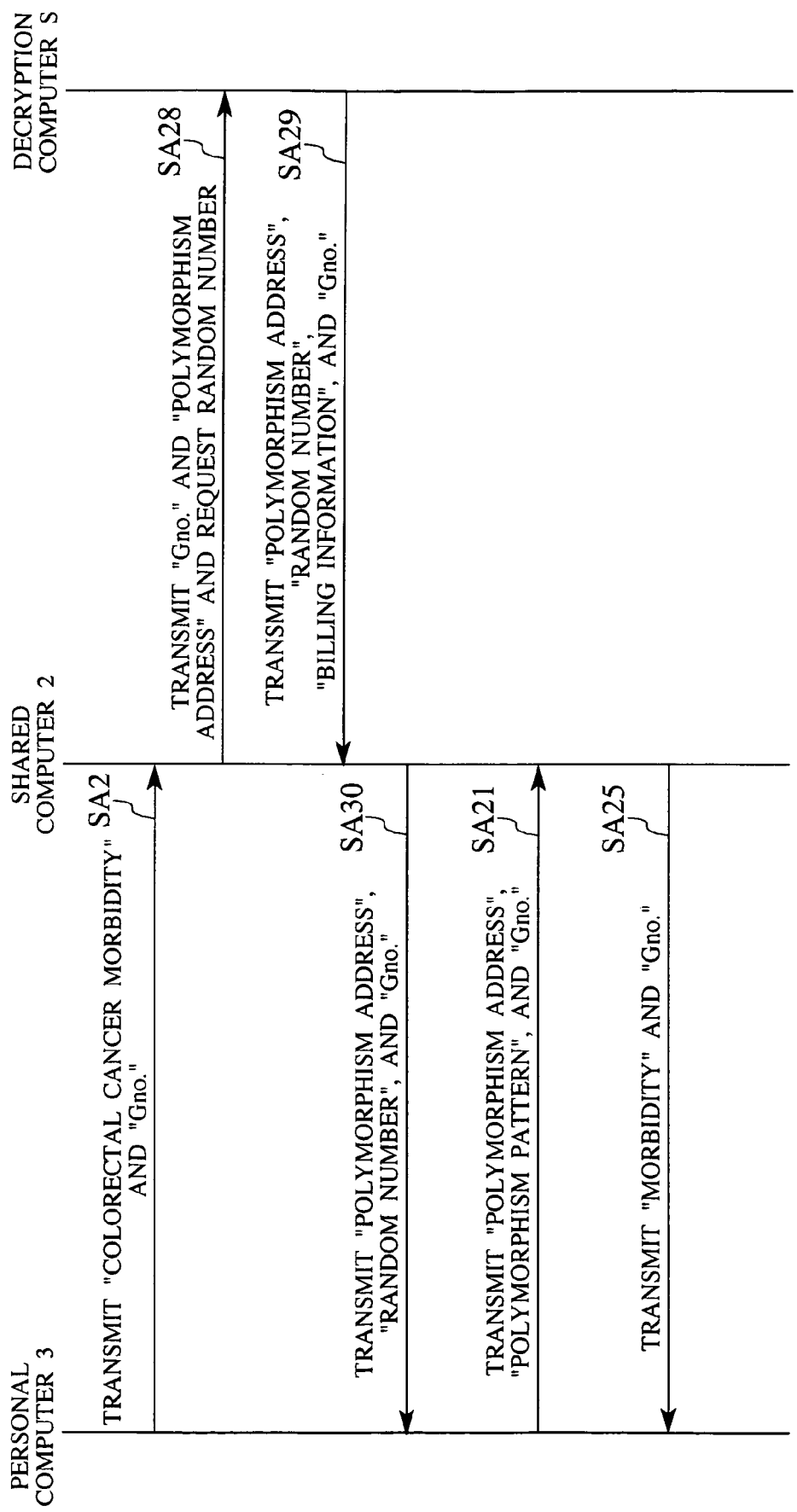
FIG. 13 is a sequence diagram illustrating other processing steps that are performed by a shared computer, personal computer, and decryption computer in a system providing morbidity rates of predefined diseases.

When a method conforming to the sequence diagram shown in FIG. 13 is used, steps A1 through A6 are performed in the same manner as indicated in the flowchart shown in FIG. 10, the "polymorphism address" associated with a "category (disease name)" (colorectal cancer) that matches the "colorectal cancer morbidity" is then read from the data that was recorded in the main database 14 in step A6, and, in step A28, the shared computer 2 transmits the requester's "Gno." and the read "polymorphism address" to the decryption computer S. More specifically, the shared computer 2 transmits the requester's "Gno." and the read "polymorphism address" to the decryption computer S in step A28 for the purpose of requesting the presentation of random numbers corresponding to the transmitted "polymorphism address".

In step A29, the decryption computer S checks the random numbers bound by the "Gno." received in step A28, reads only the random number corresponding to the "polymorphism address" received in step A28 from the random number database 37, and transmits the "Gno.", "polymorphism address", "random number", and "billing information" to the shared computer 2 via the communication network 1.

In step A30, the shared computer 2 transmits the received "Gno.", "polymorphism address", and "random number" to a personal computer 3 via the communication network 1. More specifically, in step A30, the shared computer 2 transmits command information to the personal computer 3 in order to dictate the submission of a "polymorphism pattern" corresponding to the transmitted "polymorphism address".

Upon receipt of the "Gno.", "polymorphism address", and "random number", which were transmitted from the shared computer 2 in step A30, the personal computer 3 accesses the genome-related information recording medium 24 and reads an "encrypted polymorphism pattern" corresponding to the received "polymorphism address". Subsequently, the information processing system performs steps A19 through A27 in the same manner as indicated in the flowchart in FIGS. 10 and 11 for the purpose of letting the shared computer 2 supply semantic information and/or the information related to the semantic information to the personal computer 3.

Figure 14:
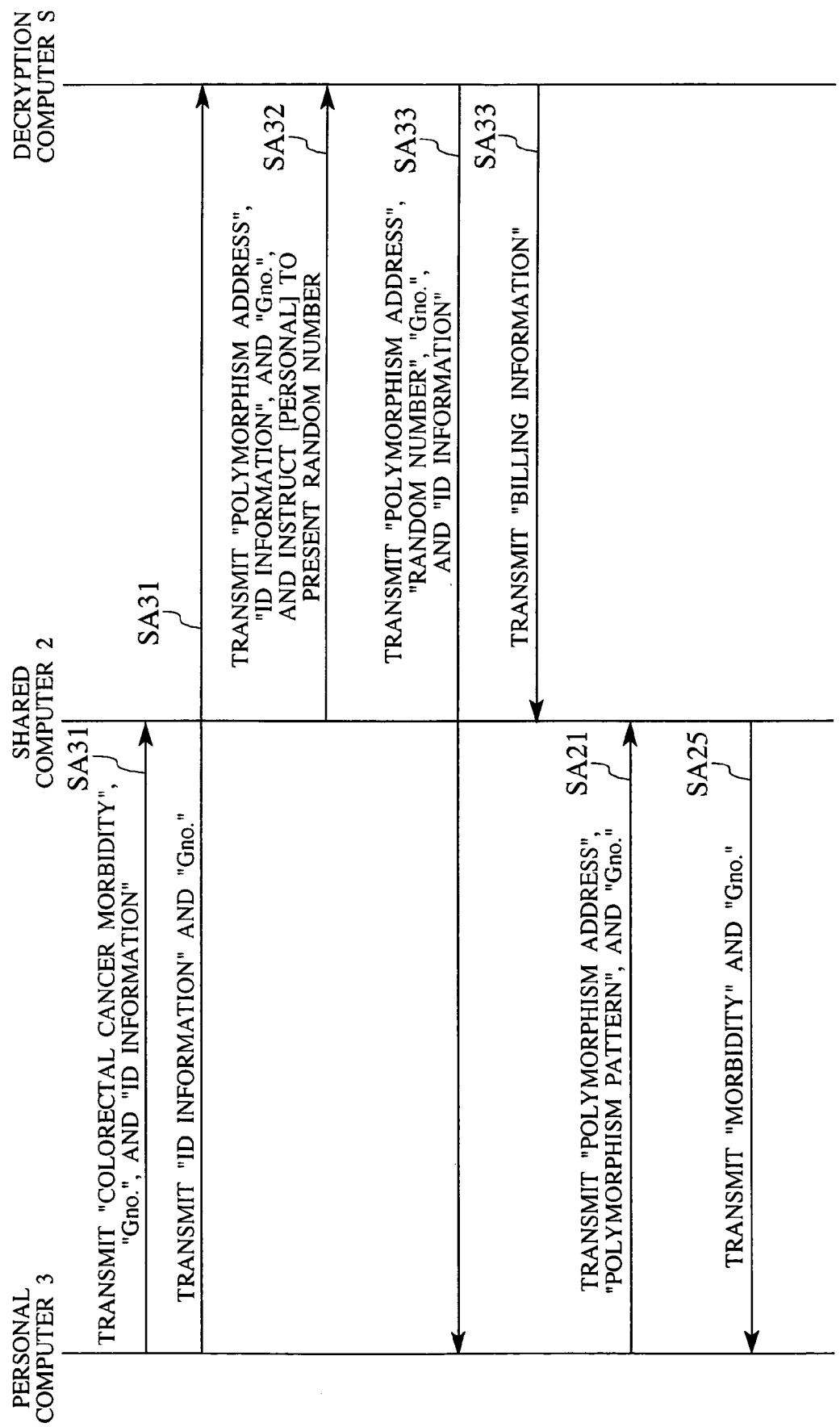
FIG. 14 is a sequence diagram illustrating other processing steps that are performed by a shared computer, personal computer, and decryption computer in a system providing morbidity rates of predefined diseases.

When a method conforming to the sequence diagram shown in FIG. 14 is used, first step A1 is performed, and then step A31 is performed so that the personal computer 3 transmits the "colorectal cancer morbidity" (request information), "Gno.", and "ID information" to the shared computer via the communication network 1. In step A31, the personal computer 3 also transmits the "ID information" and "Gno." to the decryption computer S via the communication network 1. The "ID information" is the information that the shared computer 2 and decryption computer S use to identify the personal computer 3. Therefore, if, for instance, the requester possessing the genome-related information recording medium 24 differs from the owner of the personal computer 3, the shared computer 2 and decryption computer S can use the "ID information" to determine the person to whom the personal computer 3 belongs.

Next, the shared computer 2 performs steps A3 through A6 in the same manner as indicated in the flowchart shown in FIGS. 10 and 11, reads the "polymorphism address" associated with a "category (disease name)" (colorectal cancer) that matches the "colorectal cancer morbidity" from the data that was recorded in the main database 14 in step A6, and transmits, in step A32, the "polymorphism address", "ID information", and "Gno." to the decryption computer S via the communication network 1. More specifically, the shared computer 2 transmits the "polymorphism address", "ID information", and "Gno." to the decryption computer S in step A32 for the purpose of instructing a personal computer 3, which is identified by the ID information, to present a random number corresponding to the transmitted "polymorphism address".

Next, the decryption computer S judges that the "ID information" and "Gno." received in step A31 coincide with the "ID information" and "Gno." received in step A32, checks the random numbers bound by the "Gno.", reads only the random number corresponding to the "polymorphism address" received in step A32 from the random number database 37, and transmits the "Gno.", "polymorphism address", "random number", and "ID information" to the personal computer 3 via the communication network 1 in step A33. The decryption computer S transmits the "Gno.", "polymorphism address", "random number", and "ID information" to the personal computer 3 in step A33 for the purpose of instructing the shared computer 2 to submit a "polymorphism pattern" corresponding to the transmitted "polymorphism address". In step A33, the decryption computer S also transmits "billing information" to the shared computer 2 via the communication network 1.

Upon receipt of the "Gno.", "polymorphism address", and "random number", which were transmitted from the decryption computer S in step A33, the personal computer 3 accesses the genome-related information recording medium 24 and reads an "encrypted polymorphism pattern" corresponding to the received "polymorphism address". Subsequently, the information processing system performs steps A19 through A27 in the same manner as indicated in the flowchart in FIGS. 10 and 11 for the purpose of letting the shared computer 2 supply semantic information and/or the information related to the semantic information to the personal computer 3.

Figure 15:
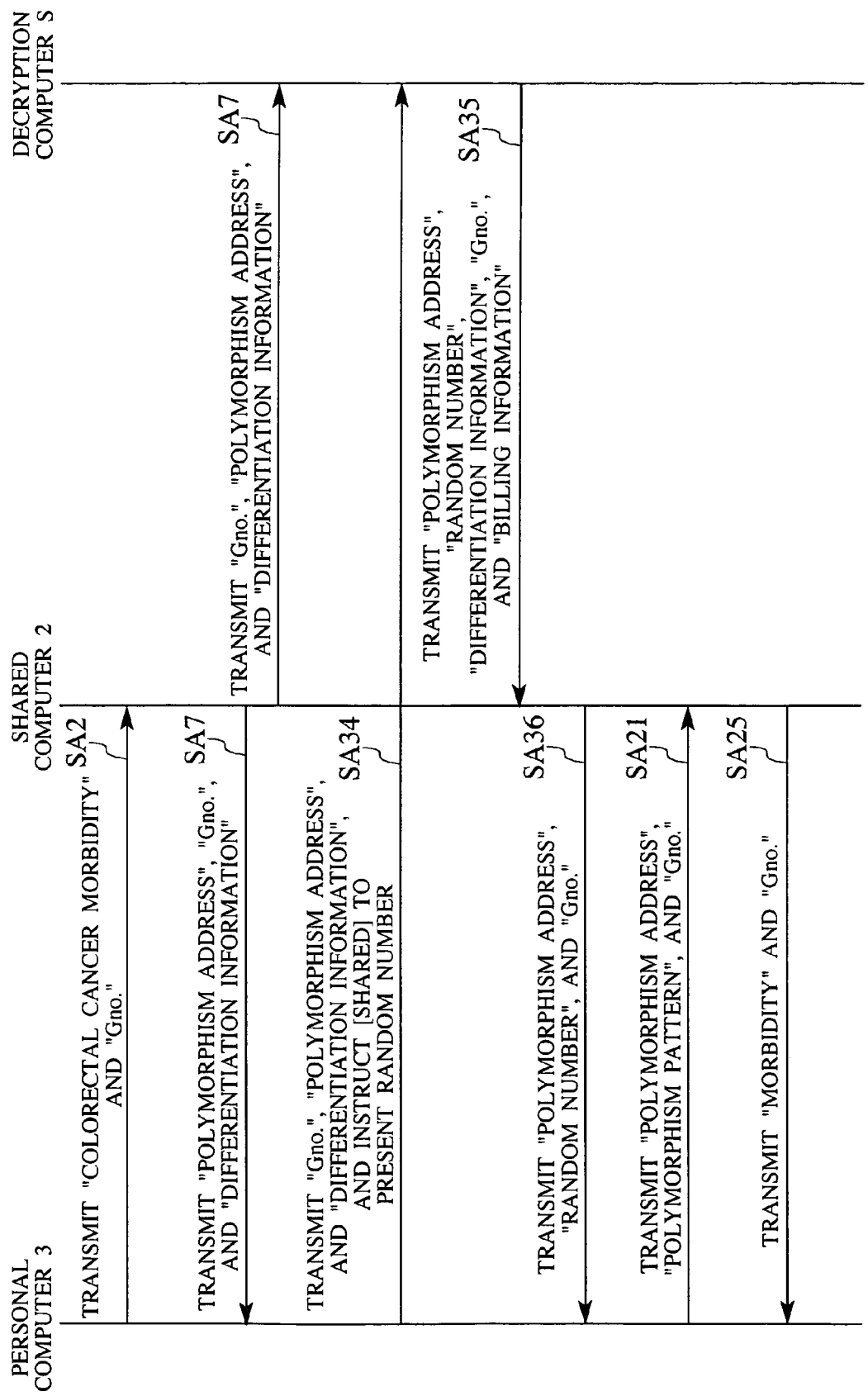
FIG. 15 is a sequence diagram illustrating other processing steps that are performed by a shared computer, personal computer, and decryption computer in a system providing morbidity rates of predefined diseases.

When a method conforming to the sequence diagram shown in FIG. 15 is used, steps A1 through A10 are first performed in the same manner as indicated in the flowchart shown in FIGS. 10 and 11. In step A34, the "polymorphism address", "differentiation information", and "Gno." received in step A8 are then transmitted to the decryption computer S via the communication network 1. More specifically, step A34 is performed so that the personal computer 3 instructs the decryption computer S to present a random number corresponding to the "polymorphism address" received in step A8 to the shared computer 2.

Next, steps A12 through A14 are first performed in the same manner as indicated in the flowchart in FIG. 10. In step A35, the decryption computer S then transmits the "Gno.", "polymorphism address", "random number", and "billing information" to the shared computer 2 via the communication network 1. After receipt of the "Gno.", "polymorphism address", "random number", and "billing information", the shared computer 2 transmits the "Gno.", "polymorphism address", and "random number" to the personal computer 3 in step A36.

Subsequently, the information processing system performs steps A17 through A27 in the same manner as indicated in the flowchart shown in FIGS. 10 and 11 so that the shared computer 2 can supply semantic information and/or the information related to the semantic information to the personal computer 3.

In the above example, the personal computer 3 possesses the decryption table 29, accesses the decryption table 29 in step A19, decrypts an encrypted polymorphism pattern in step A20 to obtain the original polymorphism pattern. However, the present invention is not limited to the above example. For example, the present invention can also be applied to a system in which the decryption computer S possesses the decryption table. Such a system can perform an information process in accordance with a sequence diagram shown in FIG. 16, 17, 18, or 19.

Figure 16:
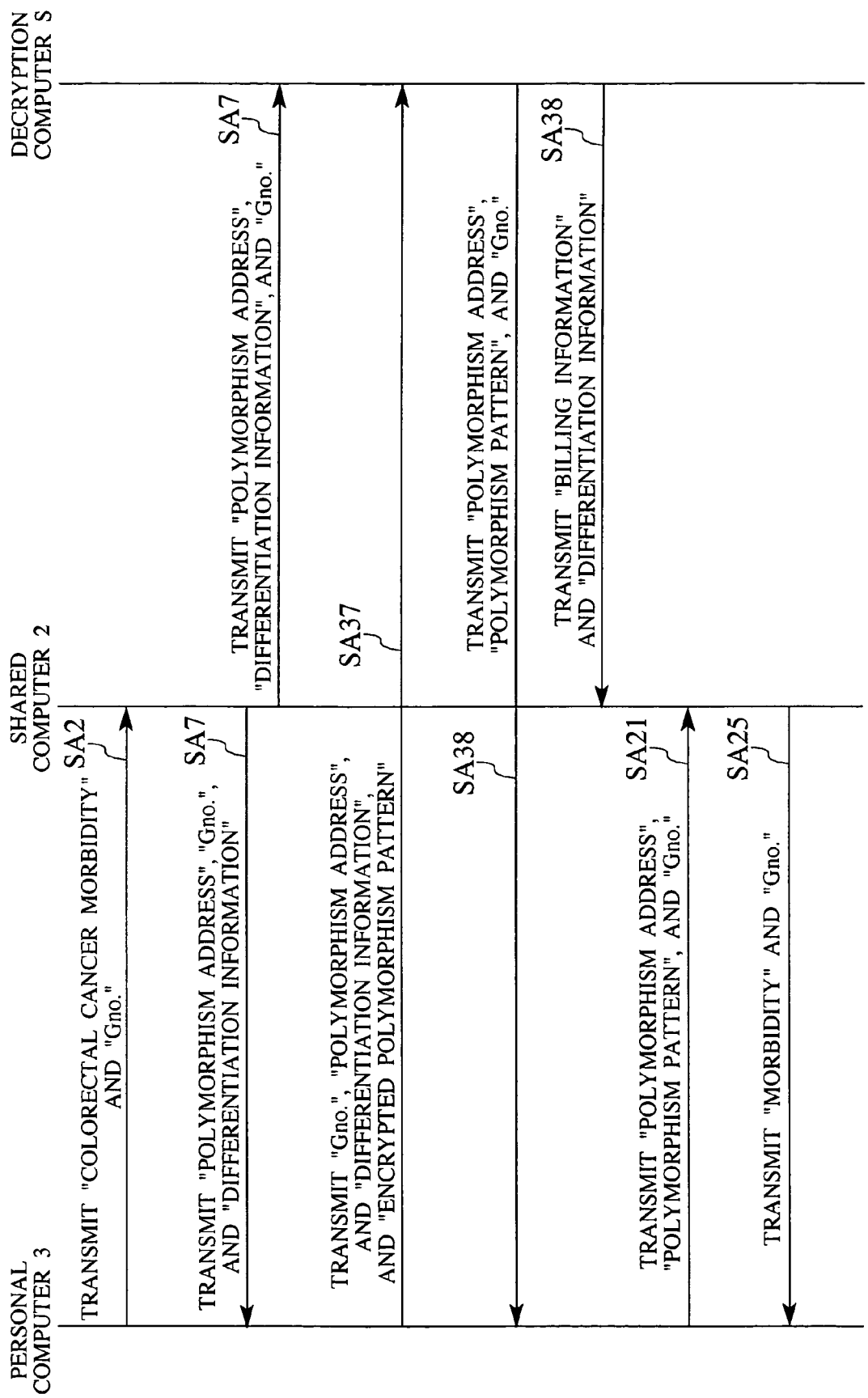
FIG. 16 is a sequence diagram illustrating other processing steps that are performed by a shared computer, personal computer, and decryption computer in a system providing morbidity rates of predefined diseases.

When a method conforming to the sequence diagram shown in FIG. 16 is used, steps A1 through A10 are performed in the same manner as indicated in the flowchart shown in FIGS. 10 and 11.

In step A37, the personal computer 3 transmits the "Gno.", "polymorphism address", "encrypted polymorphism pattern" associated with the polymorphism address, and "differentiation information", which are recorded in memory section 26, to the decryption computer S via the communication network 1. The decryption computer S checks the random numbers bound by the received "Gno.", reads only the random number corresponding to the received "polymorphism address" from the random number database 37, and collates a combination of the read random number and received "encrypted polymorphism pattern" with the decryption table for the purpose of decrypting the "encrypted polymorphism pattern" to obtain the "polymorphism pattern". In other words, the "encrypted polymorphism pattern" is decrypted in the decryption computer S to obtain the "polymorphism pattern". In step A38, the decryption computer S then transmits the "Gno.", "polymorphism address", and "polymorphism pattern" to the personal computer 3 via the communication network 1. In step A38, the decryption computer S also transmits "billing information" to the shared computer 2.

Subsequently, the personal computer 3 operates in the same manner as indicated in step A21 of the flowchart shown in FIGS. 10 and 11 to transmit the polymorphism pattern associated with a polymorphism address, supplementary information recorded as needed, and "Gno." to the shared computer 2 via the communication network 1. In this case, steps A17 through A20 of the flowchart shown in FIGS. 10 and 11 are not performed. Instead, steps A21 and beyond are performed in the same manner as indicated in the foregoing example so that the shared computer 2 can supply semantic information and/or the information related to the semantic information to the personal computer 3.

Figure 17:
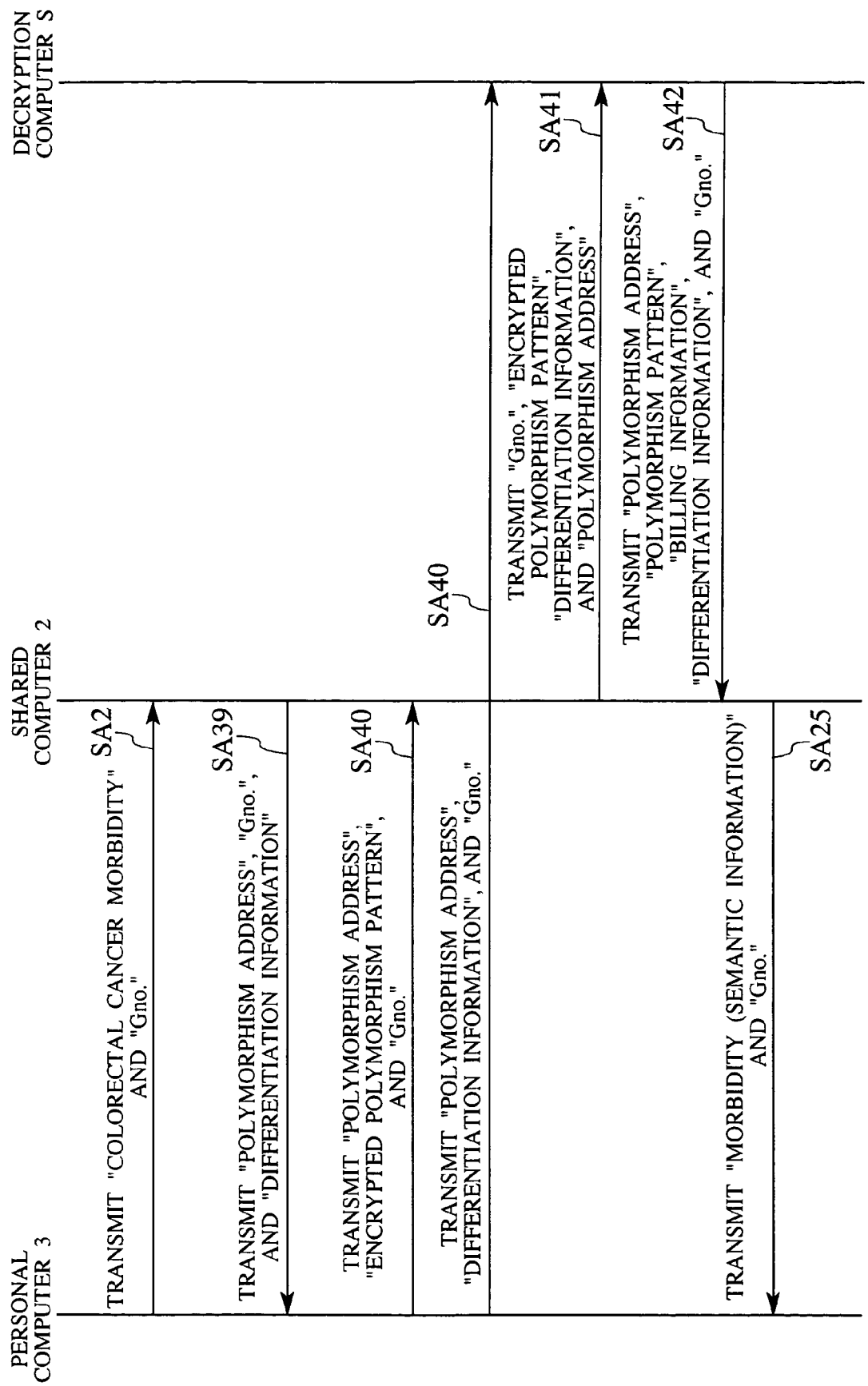
FIG. 17 is a sequence diagram illustrating other processing steps that are performed by a shared computer, personal computer, and decryption computer in a system providing morbidity rates of predefined diseases.

When a method conforming to the sequence diagram shown in FIG. 17 is used, steps A1 through A6 are first performed in the same manner as indicated in the flowchart shown in FIGS. 10 and 11. In step A39, the shared computer 2 then transmits the "Gno.", "polymorphism address", and "differentiation information" to the personal computer 3. In addition, the shared computer 2 also transmits command information to the personal computer 3 in order to dictate the submission of a "polymorphism pattern" corresponding to the "polymorphism address" to be transmitted. Upon receipt of the "Gno.", "polymorphism address", "differentiation information", and command information, the personal computer 3 reads an "encrypted polymorphism pattern" corresponding to the received polymorphism address from the data II recording and records the acquired information in memory section 26. In step A40, the personal computer 3 then transmits the "Gno.", "polymorphism address", and "encrypted polymorphism pattern" to the shared computer 2 and transmits the "Gno.", "polymorphism address", and "differentiation information" to the decryption computer S.

After receipt of the "Gno.", "polymorphism address", and "encrypted polymorphism pattern", the shared computer 2 performs step A41 to transmit the "Gno.", "polymorphism address", "encrypted polymorphism pattern", and "differentiation information" to the decryption computer S. The decryption computer S verifies that the "Gno.", "polymorphism address", and "differentiation information" transmitted in step A40 coincide with the "Gno.", "polymorphism address", and "differentiation information" transmitted in step A41. After verifying such a coincidence, the decryption computer S checks the random numbers bound by the received "Gno.", reads only the random number corresponding to the received "polymorphism address" from the random number database 37, and collates a combination of the read random number and received "encrypted polymorphism pattern" with the decryption table for the purpose of decrypting the "encrypted polymorphism pattern" to obtain the "polymorphism pattern". It means that the "encrypted polymorphism pattern" is decrypted in the decryption computer S to acquire the "polymorphism pattern".

In step A42, the decryption computer S transmits the "polymorphism address", "polymorphism pattern" associated with the polymorphism address, "Gno.", "differentiation information", and "billing information" to the shared computer 2. Subsequently, the information processing system performs steps A23 through A27 in the same manner as indicated in the flowchart shown in FIG. 10 so that the shared computer 2 can supply semantic information and/or the information related to the semantic information to the personal computer 3. Within the information process conforming to the sequence diagram shown in FIG. 17, the personal computer 3 may issue a command in step A40 to instruct the decryption computer S to submit a polymorphism pattern, or the shared computer 2 may issue a command in step A41 to instruct the decryption computer S to submit a polymorphism pattern.

Figure 18:
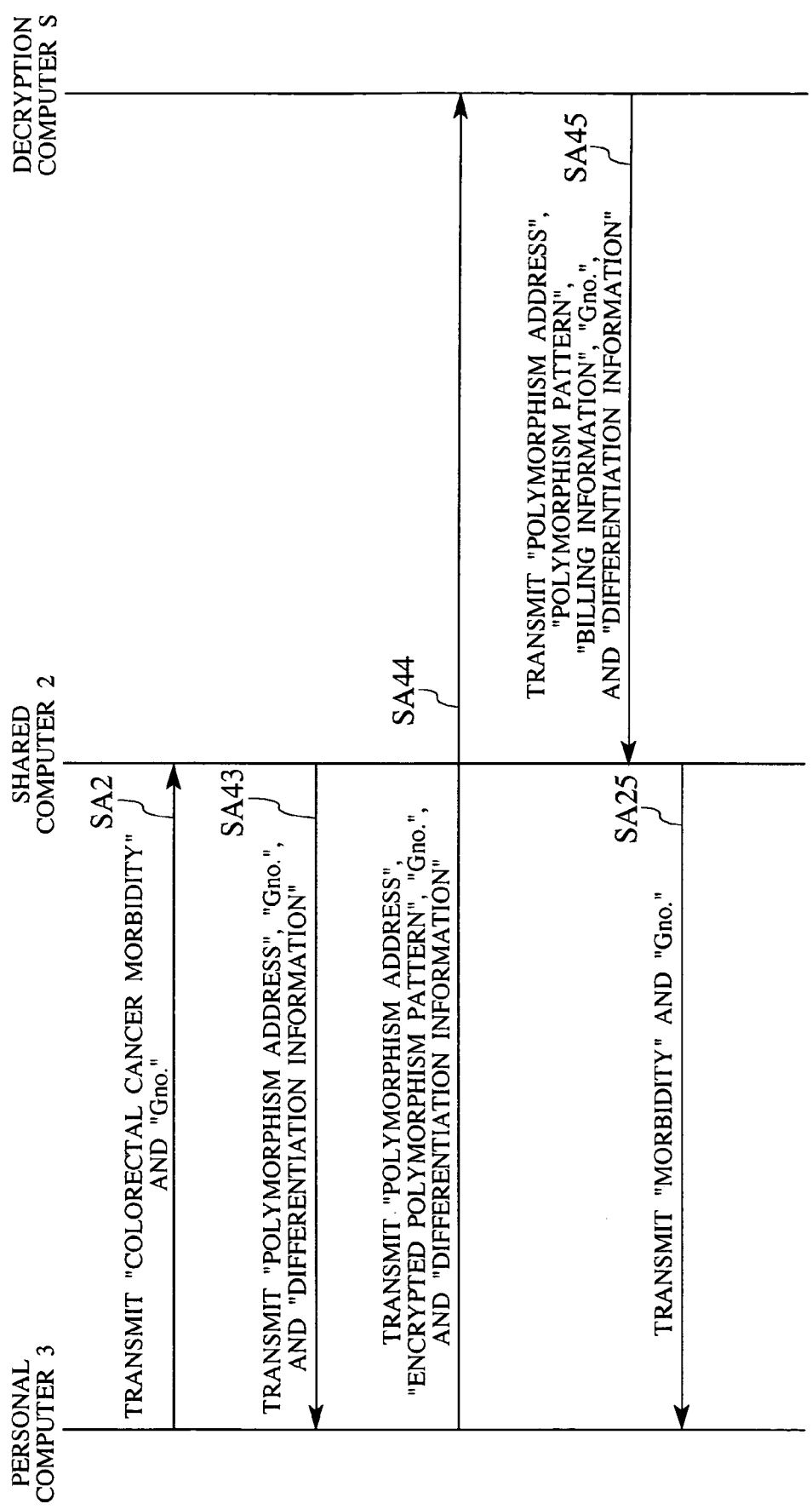
FIG. 18 is a sequence diagram illustrating other processing steps that are performed by a shared computer, personal computer, and decryption computer in a system providing morbidity rates of predefined diseases.

When a method conforming to the sequence diagram shown in FIG. 18 is used, steps A1 through A6 are first performed in the same manner as indicated in the flowchart shown in FIGS. 10 and 11. In step A43, the shared computer 2 then transmits the "Gno.", "polymorphism address", and "differentiation information" to the personal computer 3.

In addition, the shared computer 2 also transmits command information to the personal computer 3 in order to dictate the submission of an "encrypted polymorphism pattern" corresponding to the "polymorphism address" to be transmitted. Upon receipt of the "Gno.", "polymorphism address", "differentiation information", and command information, the personal computer 3 reads an "encrypted polymorphism pattern" corresponding to the received polymorphism address from the data II recording and records the acquired information in memory section 26. In step A44, the personal computer 3 then transmits the "Gno.", "polymorphism address", "encrypted polymorphism pattern", and "differentiation information" to the decryption computer S. In this instance, the personal computer 3 transmits command information to the decryption computer S in order to instruct the decryption computer S to decrypt the "encrypted polymorphism pattern" and present the decrypted polymorphism pattern to the shared computer 2.

The decryption computer S checks the random numbers bound by the received "Gno.", reads only the random number corresponding to the received "polymorphism address" from the random number database 37, and collates a combination of the read random number and received "encrypted polymorphism pattern" with the decryption table for the purpose of decrypting the "encrypted polymorphism pattern" to obtain the "polymorphism pattern". It means that the "encrypted polymorphism pattern" is decrypted in the decryption computer S to acquire the "polymorphism pattern".

In step A45, the decryption computer S transmits the "polymorphism address", "polymorphism pattern" associated with the polymorphism address, "Gno.", "differentiation information", and "billing information" to the shared computer 2. Subsequently, the information processing system performs steps A23 through A27 in the same manner as indicated in the flowchart shown in FIG. 10 so that the shared computer 2 can supply semantic information and/or the information related to the semantic information to the personal computer 3.

Figure 19:
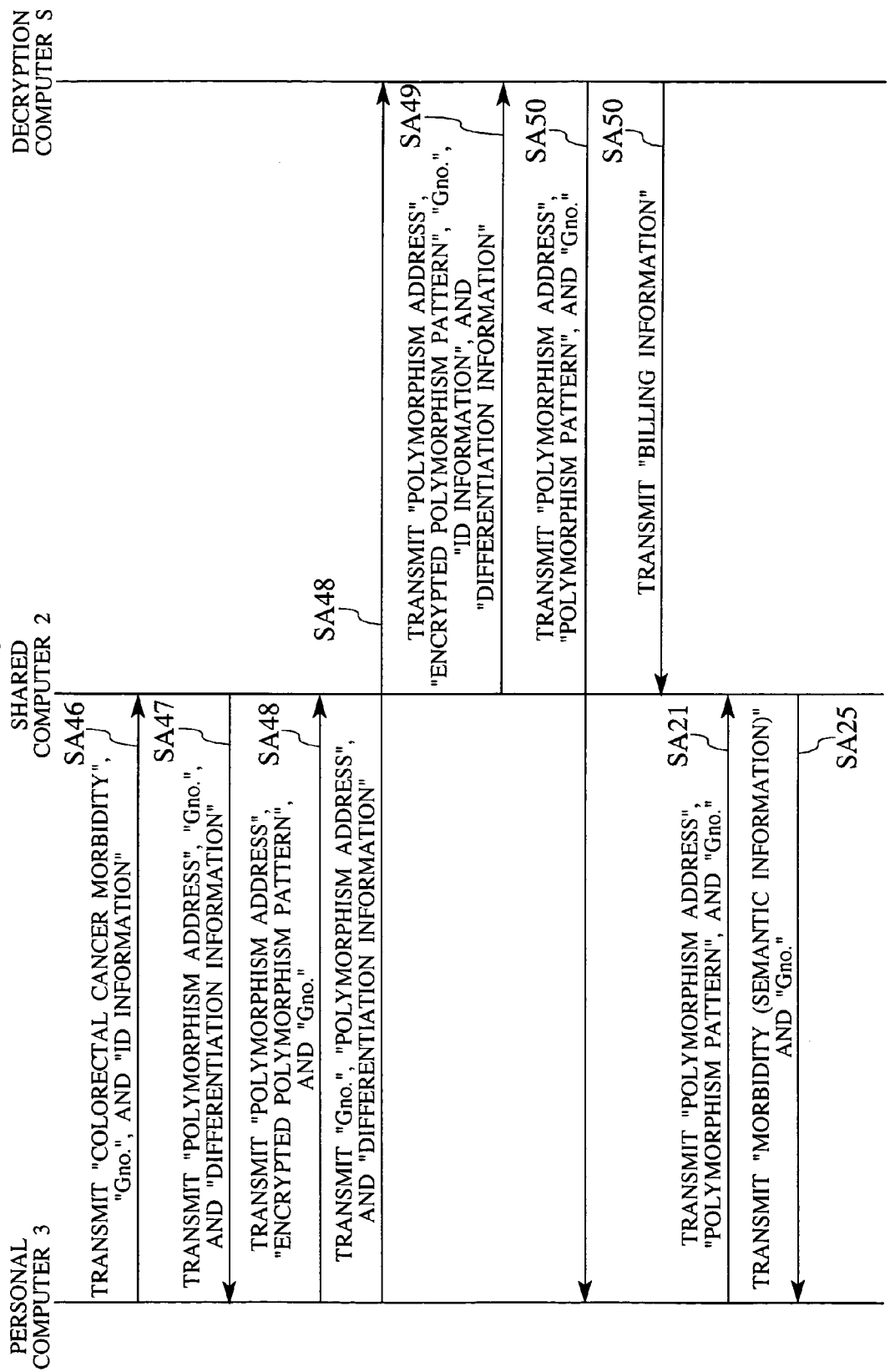
FIG. 19 is a sequence diagram illustrating other processing steps that are performed by a shared computer, personal computer, and decryption computer in a system providing morbidity rates of predefined diseases.

When a method conforming to the sequence diagram shown in FIG. 19 is used, step A1 is first performed in the same manner as indicated in the flowchart shown in FIGS. 10 and 11. Step A46 is then performed so that the personal computer 3 transmits "colorectal cancer morbidity" (request information), "Gno.", and "ID information" to the shared computer 2 via the communication network 1. Next, steps A3 through A6 are performed in the same manner as indicated in the flowchart shown in FIGS. 10 and 11. Step A47 is then performed so that the shared computer 2 transmits a "polymorphism address", "differentiation information", and "Gno." to the personal computer 3 via the communication network 1, and also transmits command information to the personal computer 3 in order to dictate the submission of an "encrypted polymorphism pattern" corresponding to the "polymorphism address" to be transmitted. In other words, step A47 is performed so that the shared computer 2 transmits the "Gno." "polymorphism address", "differentiation information", and command information to the personal computer 3 for the purpose of instructing the personal computer 3 to present an encrypted polymorphism pattern corresponding to the transmitted "polymorphism address".

Upon receipt of the "Gno.", "polymorphism address", "differentiation information", and command information, the personal computer 3 reads an "encrypted polymorphism pattern" corresponding to the received polymorphism address from the data II recording and records the acquired information in memory section 26. Next, in step A48, the personal computer 3 transmits the "Gno.", "polymorphism address", and "encrypted polymorphism pattern" to the shared computer 2. In step A48, the personal computer 3 also transmits the "Gno.", "polymorphism address", and "differentiation information" to the decryption computer S for the purpose of transmitting command information to the decryption computer S to instruct the decryption computer S to decrypt and present the encrypted polymorphism pattern.

After receipt of the "Gno.", "polymorphism address", and "encrypted polymorphism pattern", the shared computer 2 performs step A49 to transmit the "Gno.", "polymorphism address", "encrypted polymorphism pattern", "differentiation information", and "ID information" to the decryption computer S. The decryption computer S verifies that the "Gno.", "polymorphism address", and "differentiation information" transmitted in step A48 coincide with the "Gno.", "polymorphism address", and "differentiation information" transmitted in step A49. After verifying such a coincidence, the decryption computer S checks the random numbers bound by the received "Gno.", reads only the random number corresponding to the received "polymorphism address" from the random number database 37, and collates a combination of the read random number and received "encrypted polymorphism pattern" with the decryption table for the purpose of decrypting the "encrypted polymorphism pattern" to obtain the "polymorphism pattern". It means that the "encrypted polymorphism pattern" is decrypted in the decryption computer S to acquire the "polymorphism pattern".

In step A50, the decryption computer S then identifies the personal computer 3 in accordance with the "ID information" transmitted in step A49, and transmits the "Gno.", "polymorphism address", and "polymorphism pattern" associated with the polymorphism address to the personal computer 3. In step A50, the decryption computer S also transmits "billing information" and "differentiation information" to the shared computer 2. Subsequently, the information processing system performs steps A21 through A27 in the same manner as indicated in the flowchart shown in FIGS. 10 and 11 to let the shared computer 2 supply semantic information and/or the information related to the semantic information to the personal computer 3.

Figure 20:
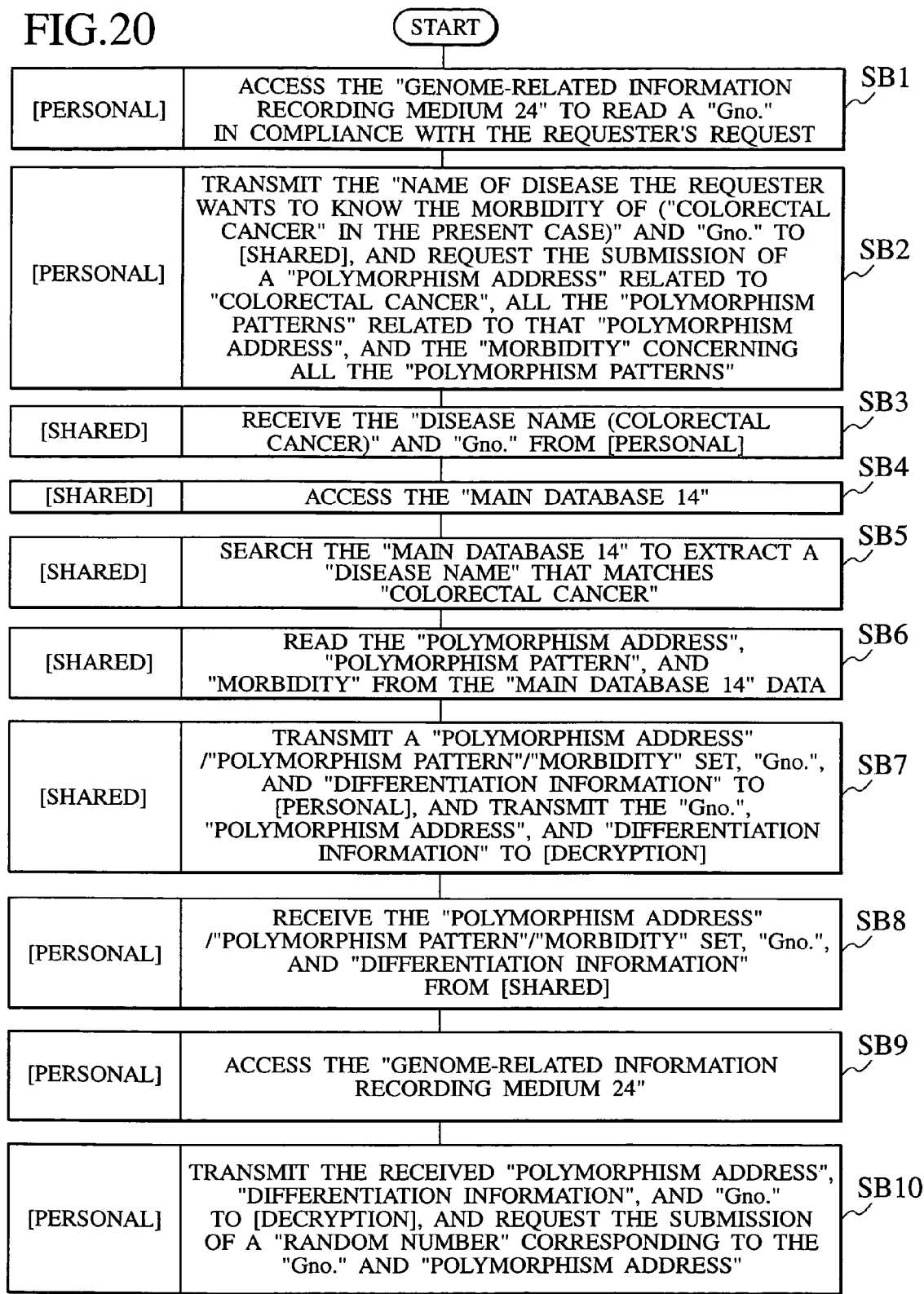
FIG. 20 is a flowchart illustrating other processing steps that are performed by a shared computer, personal computer, and decryption computer in a system providing morbidity rates of predefined diseases.
Figure 21:
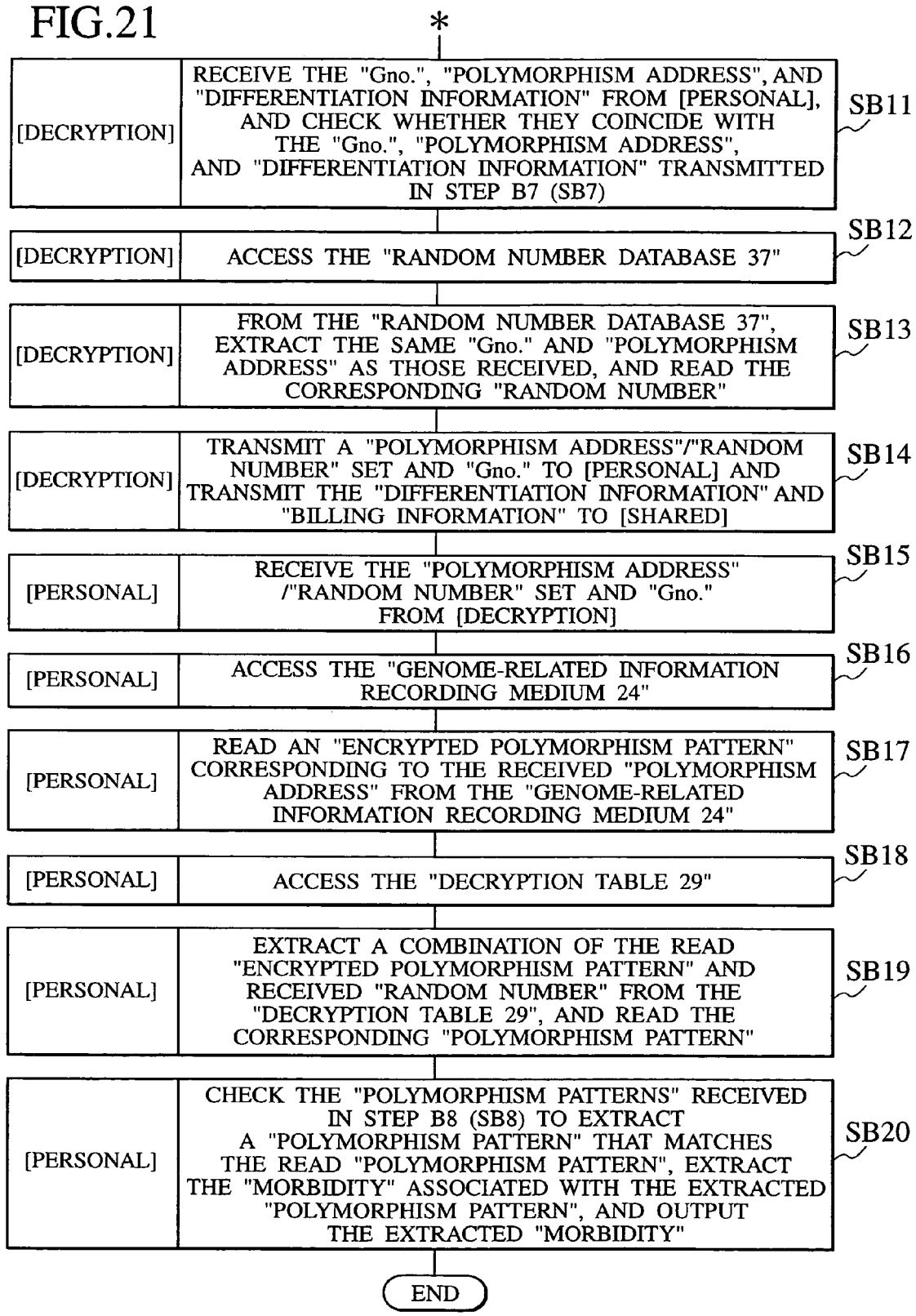
FIG. 21 is a flowchart that is a continuation of FIG. 20, which illustrates other processing steps that are performed by a shared computer, personal computer, and decryption computer in a system providing morbidity rates of predefined diseases.
Figure 22:
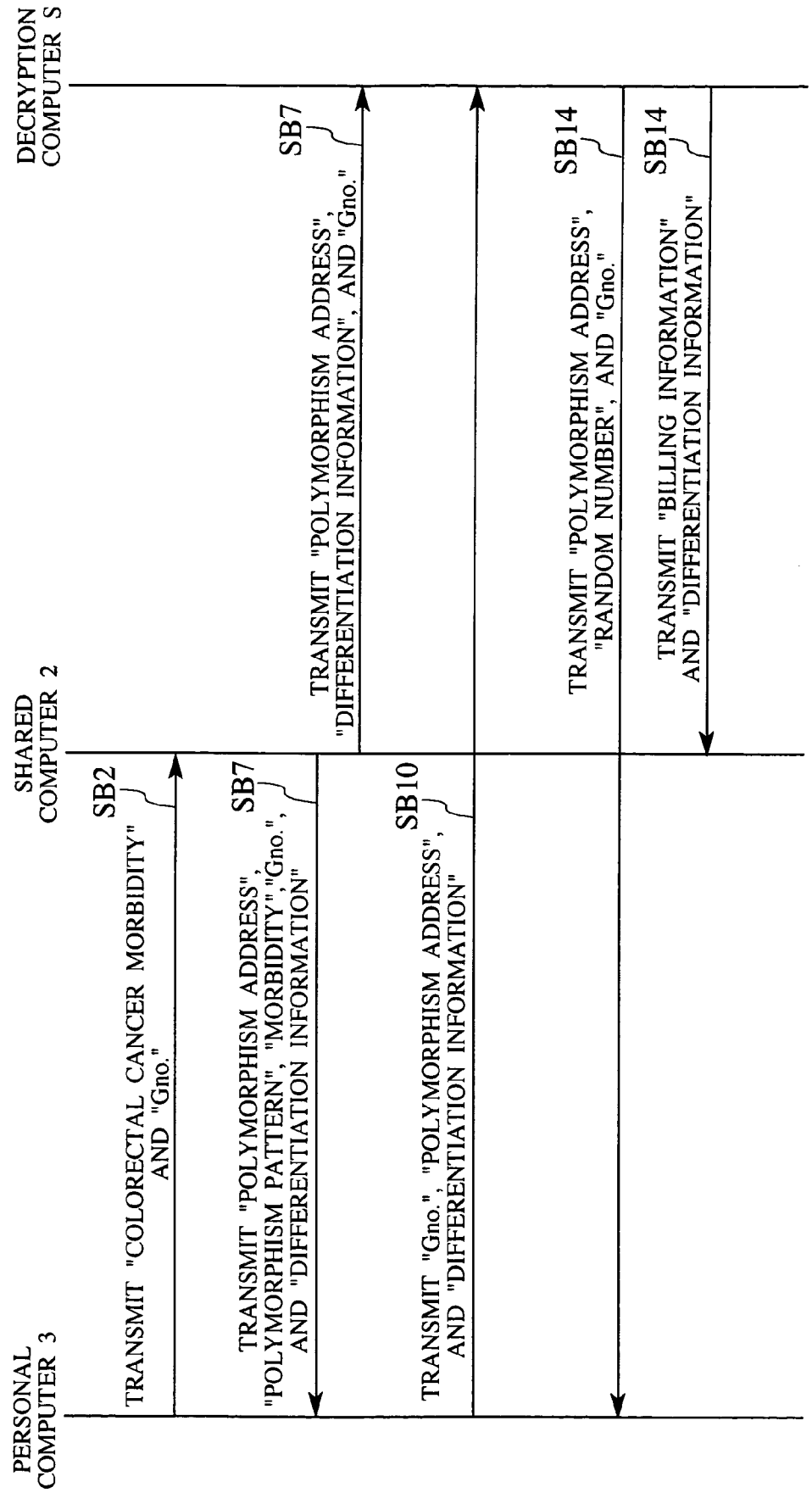
FIG. 22 is a sequence diagram illustrating other processing steps (shown in FIGS. 20 and 21) that are performed by a shared computer, personal computer, and decryption computer in a system providing morbidity rates of predefined diseases.

In the information processing system, the processing program 13 recorded in the memory 7 of the shared computer 2, the processing program 27 recorded in the memory 23 of a personal computer 3, and the processing program 33 recorded in the memory 34 of the decryption computer S may perform information processing operations in accordance with the flowchart shown in FIGS. 20 and 21. In the flowchart shown in FIGS. 20 and 21, the processing steps marked "[Shared]" are performed by the shared computer 2; the processing steps marked "[Personal]" are performed by the personal computer 3; and the processing steps marked "[Decryption]" are performed by the decryption computer S. The sequence diagram shown in FIG. 22 illustrates an information process that is performed in accordance with the flowchart in FIGS. 20 and 21.

Step B1 (SB1) is first performed to start processing program 27, which is recorded in memory 23, so that the requester can use the information processing system. Processing program 27 drives the reading device 25 of the personal computer 3 to access the genome-related information recording medium 24 and read the "Gno.", which is recorded as data II on the genome-related information recording medium 24. The read "Gno." is then stored in memory section 26.

It is preferred that a password or biological information such as a fingerprint, for example, be used prior to step B1 for authentication in order to check whether or not the genome-related information recording medium 24 belongs to the requester.

In step B2 (SB2), the information that the requester wishes to receive, for example, the "colorectal cancer morbidity" (request information), is entered into the personal computer 3 in accordance with an on-screen image that is displayed on the display device 22 by processing program 27, and the personal computer 3 transmits the "colorectal cancer morbidity" and "Gno." to the shared computer 2 via the communication network 1 and requests the submission of a "polymorphism address" whose category (disease name) recording in the main database 14 is a colorectal cancer, all the "polymorphism patterns" associated with the "polymorphism address", and the "morbidities" implied by all the "polymorphism patterns". In other words, the requester requests, in step B2, information that comprises a "polymorphism address" whose category (disease name) recording in the main database 14 is a colorectal cancer, all the "polymorphism patterns" associated with the "polymorphism address", and the "morbidities" implied by all the "polymorphism patterns".

In step B3 (SB3), the shared computer 2 receives the above request information. Upon receipt of the request information, the shared computer 2 starts processing program 13. In step B4 (SB4), the main database 14 is accessed in accordance with processing program 13.

In step B5 (SB5), the category (disease name) recordings in the main database 14 are searched in accordance with processing program 13 to extract a category (disease name) that matches the requested "colorectal cancer morbidity" (colorectal cancer). In step B6 (SB6), the main database 14 is accessed in accordance with processing program 13 to read a "polymorphism address" associated with a "category (disease name)" (colorectal cancer) that matches the "colorectal cancer morbidity", all the "polymorphism patterns" associated with the polymorphism address, and the "morbidity" implied by all the polymorphism patterns. The read "polymorphism address", "polymorphism patterns", and "morbidity" are then associated with the request information and stored in memory section A 10. It means that memory section A 10 records a "polymorphism address", "polymorphism patterns", and "morbidity" for a predetermined "Gno.".

In step B7 (SB7), the "Gno.", "polymorphism address", "polymorphism patterns", and "morbidity", which are recorded in memory section A 10, are transmitted together with the "differentiation information" to the personal computer 3 via the communication network 1. In addition, the "Gno.", "polymorphism address", and "differentiation information" are transmitted to the decryption computer S. Further, the information about the address of the decryption computer S may be transmitted to the personal computer 3 in step B7.

In step B8 (SB8), the "Gno.", "polymorphism address", "polymorphism patterns", "morbidity", and "differentiation information", which have been transmitted from the shared computer 2, are received. The received "Gno.", "polymorphism address", "polymorphism patterns", "morbidity", and "differentiation information" are then recorded in memory section 26.

In step B9 (SB9), the data II recording on the genome-related information recording medium 24 is accessed in accordance with processing program 27. It is preferred that the data I recording on the genome-related information recording medium 24 be also accessed in this instance to check whether or not the received "Gno." is correct.

In step B10 (SB10), the "polymorphism address", "differentiation information", and "Gno." recorded in memory section 26 are transmitted to the decryption computer S in accordance with processing program 27. In other words, step B10 is performed so that the personal computer 3 requests the decryption computer S to present the random number corresponding to the "polymorphism address" that was received in step B8. The personal computer 3 may access the decryption computer S in accordance with the information about the address of the decryption computer S, which was received in step B8.

In step B11 (SB11), the decryption computer S receives the "Gno.", "polymorphism address", and "differentiation information" from the personal computer 3. In step B11, the decryption computer S judges whether or not the received "Gno.", "polymorphism address", and "differentiation information" coincide with the "Gno.", "polymorphism address", and "differentiation information" that were transmitted from the shared computer 2 in step B7.

If it is judged that the "Gno.", "polymorphism address", and "differentiation information" received in step B11 coincide with the "Gno.", "polymorphism address", and "differentiation information" transmitted from the shared computer 2 in step B7, step B12 (SB12) is performed so that the processing program 33 of the decryption computer S operates to access the random number database 37. If, on the other hand, it is judged that the "Gno.", "polymorphism address", and "differentiation information" received in step B11 do not coincide with the "Gno.", "polymorphism address", and "differentiation information" transmitted from the shared computer 2 in step B7, the process for step B12 is not performed.

In step B13 (SB13), the random numbers bound by the "Gno." received in step B11 are checked so as to read only the random number corresponding to the "polymorphism address" received in step B11 from the random number database 37. The read random number is then associated with the "Gno.", "polymorphism address", and "differentiation information" received in step B11 and recorded in memory section 39.

In step B14 (SB14), the decryption computer S transmits the "Gno.", "polymorphism address", and "random number" recorded in memory section 39 to the personal computer 3 via the communication network 1. In step B14, the decryption computer S also transmits the "differentiation information" and "billing information" to the shared computer 2 via the communication network 1. According to step B14, the shared computer 2 is billed, instead of the personal computer 3, for random number supply from the decryption computer S to the personal computer 3. The "differentiation information" and "billing information" may be transmitted to, for instance, a credit company instead of being directly transmitted to the shared computer 2 for the purpose of indirectly billing the shared computer 2 for random number supply. When the "differentiation information" and "billing information" are directly transmitted to the shared computer 2, the differentiation information is the "information about a direct billing destination". When, for instance, the differentiation information is transmitted to a credit company, it is the "information about an indirect billing destination".

In step B15 (SB15), the "Gno.", "polymorphism address", and "random number" transmitted from the decryption computer S are received by the personal computer 3. The received "Gno.", "polymorphism address", and "random number" are stored in memory section 26.

In step B16 (SB16), the processing program 27 for the personal computer 3 operates to access the genome-related information recording medium 24. In step B17 (SB17), the "encrypted polymorphism pattern" corresponding to the "polymorphism address" received in step B15 is read from the data II recording on the genome-related information recording medium 24. The read "encrypted polymorphism pattern" is then associated with the corresponding "polymorphism address" and recorded in memory section 26.

In step B18 (SB18), the processing program 27 for the personal computer 3 operates to access the decryption table 29. In step B19 (SB19), the random number received in step B15 is combined with the read "encrypted polymorphism pattern", and the decryption table 29 is used to decrypt the "encrypted polymorphism pattern" to obtain the original "polymorphism pattern". In other words, step B19 is performed so as to obtain the "polymorphism pattern" that corresponds to the "polymorphism address" received in step B8. The obtained polymorphism pattern is associated with the corresponding "polymorphism address" and recorded in memory section 26.

In step B20 (SB20), all the "polymorphism patterns" associated with the polymorphism address received in step B8 are checked to extract the polymorphism pattern that matches the polymorphism pattern obtained in step B19, and then the "morbidity" associated with the extracted polymorphism pattern is extracted and output. The requester can then obtain the colorectal cancer morbidity (semantic information). In step B20, the supplementary information recorded as data III, data IV, and data V may be simultaneously read to correct the colorectal cancer morbidity with the supplementary information and output the corrected colorectal cancer morbidity.

In the information processing system in which a polymorphism pattern recorded on the genome-related information recording medium 24 is encrypted, the polymorphism pattern cannot possibly be deciphered even when the genome-related information recording medium 24 is stolen or otherwise lost. The polymorphism pattern is, by nature, specific to an individual, is highly confidential, and needs to be handled with great care. The information processing system can properly protect the information about a highly confidential polymorphism pattern and successfully prevent it from being illegally used by a third party. Spoofing and other similar deception can be avoided particularly if authentication is performed prior to step B1. As a result, illegal use can be prevented with increased certainty.

In the above instance, it should particularly be noted that the genome-related information 28, which is recorded on the genome-related information recording medium 24, is not output to the outside of the personal computer 3 at all. In other words, the genome-related information 28 is merely exchanged between the genome-related information recording medium 24 and personal computer 3. Therefore, the information processing system can prevent the genome-related information 28, which is highly confidential and specific to an individual, from leaking out with increased certainty.

In the information processing system, it is requested in step B10 that the decryption computer S present the "random number" associated with the polymorphism address received in step B8 for the purpose of decrypting the "encrypted polymorphism pattern" corresponding to the polymorphism address received in step B8. However, the present invention is not limited to such an information processing system. The present invention can also be applied to an information processing system in which the requester requests the decryption computer S to present all the "random numbers" associated with the polymorphism address without regard to the polymorphism address received in step B8.

In the above case, the requester does not need to transmit the "polymorphism address" received in step B8 to the decryption computer S. If the "polymorphism address" received in step B8 is transmitted to the decryption computer S via the communication network 1, the type of information requested by the requestor might be identified in the event of illegal access or other contingency. In the above case, however, all the "random numbers" associated with the polymorphism address are requested. Therefore, the type of information requested by the requestor cannot possibly be identified in the event of illegal access or other contingency when the decryption computer S and personal computer 3 exchange information.

It is preferred in the above case that the personal computer 3 use only the "random number" concerning the "polymorphism address" received in step B8 to achieve decryption although there are various other "random numbers" that are associated with the polymorphism address derived from the decryption computer S.

Figure 23:
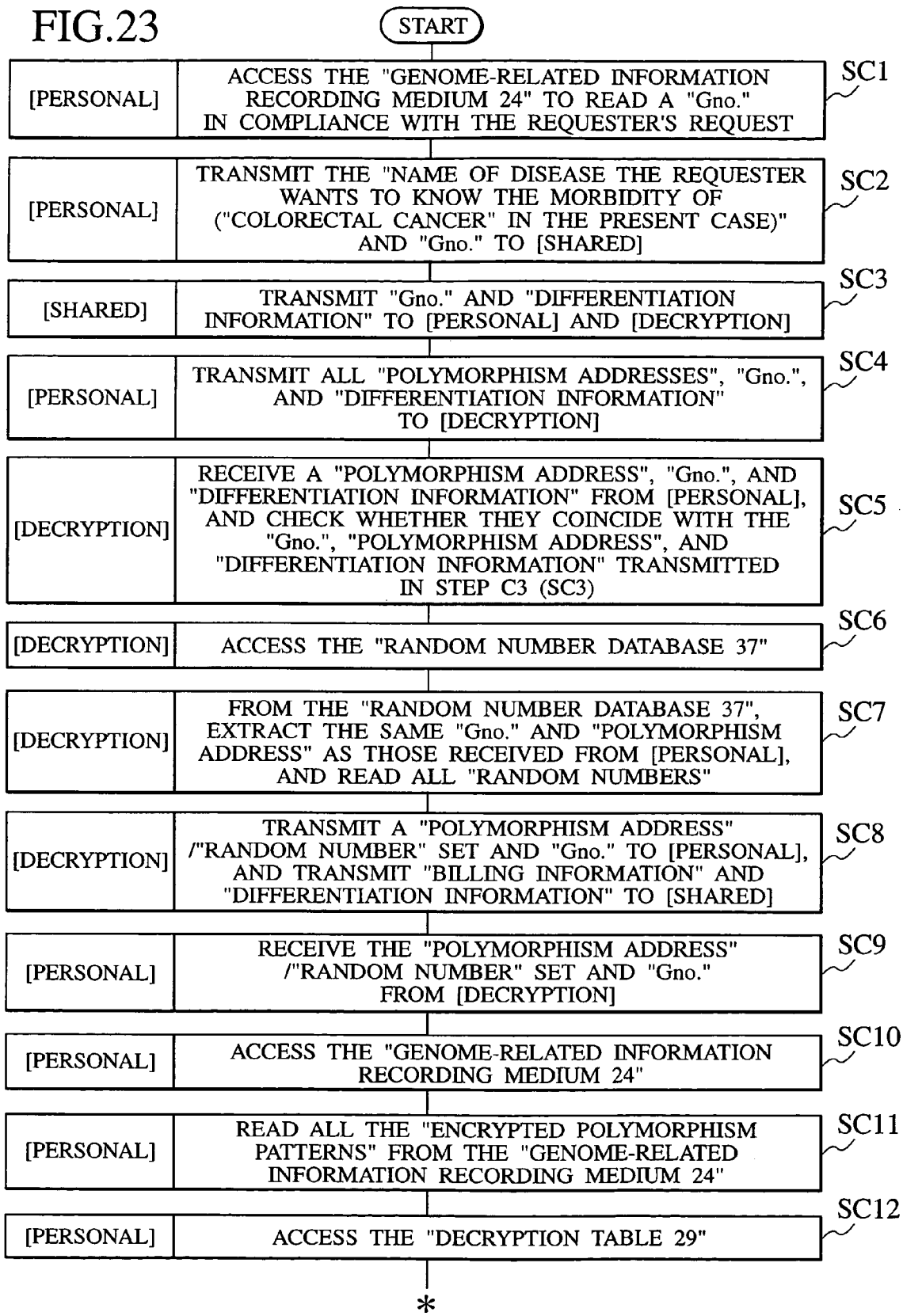
FIG. 23 is a flowchart further illustrating other processing steps that are performed by a shared computer, personal computer, and decryption computer in a system providing morbidity rates of predefined diseases.
Figure 24:
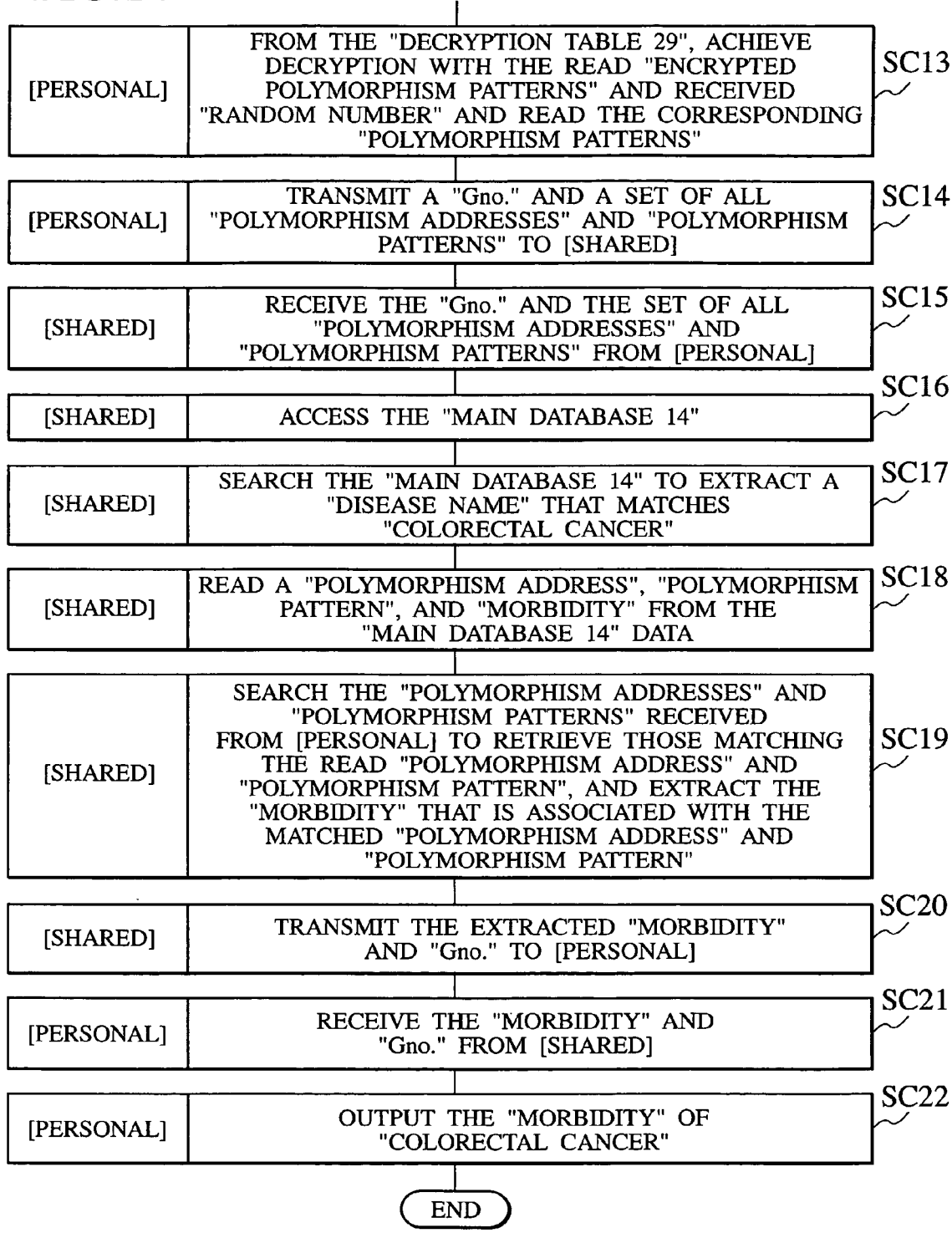
FIG. 24 is a flowchart that is a continuation of FIG. 23, which further illustrates other processing steps that are performed by a shared computer, personal computer, and decryption computer in a system providing morbidity rates of predefined diseases.
Figure 25:
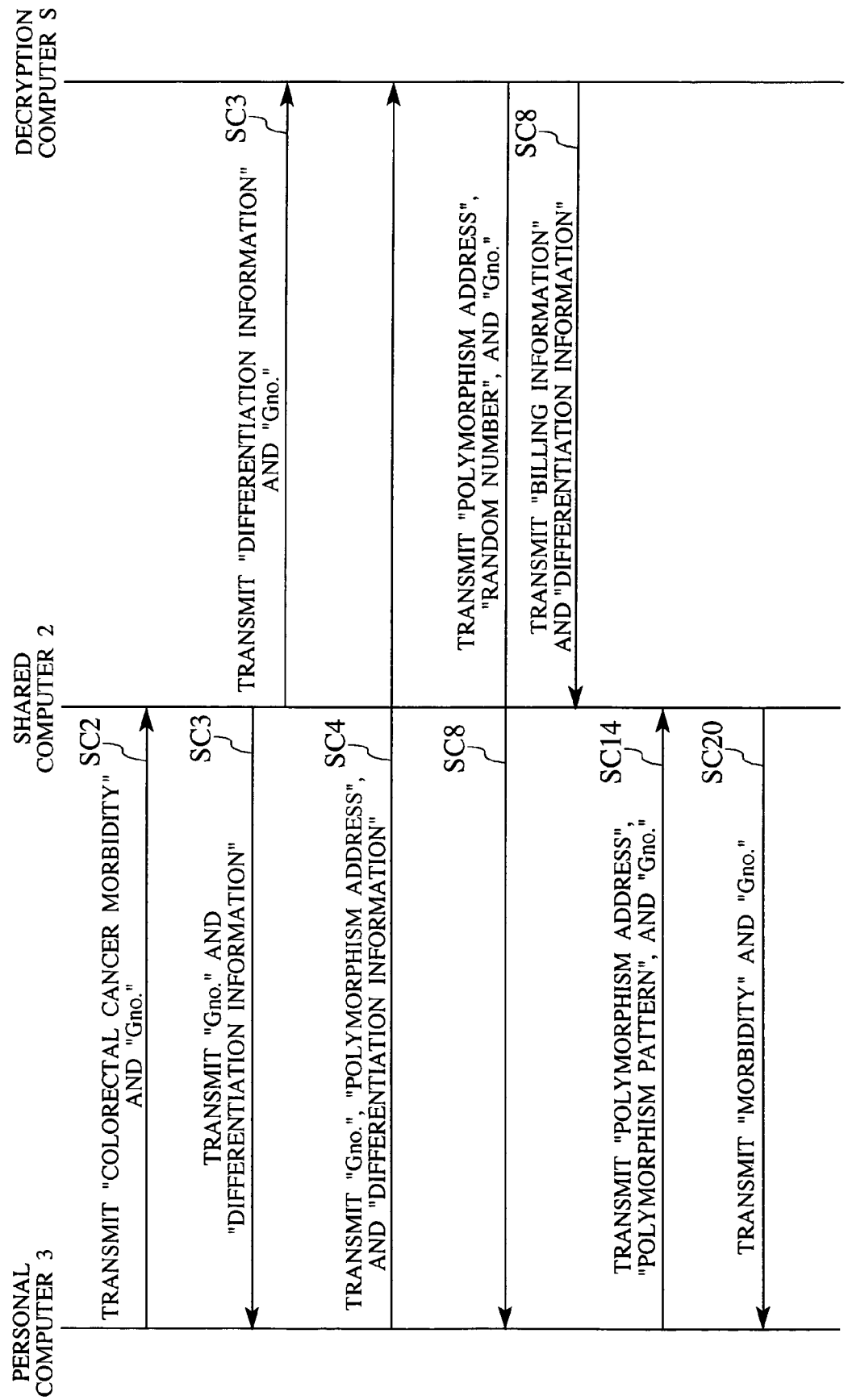
FIG. 25 is a sequence diagram further illustrating other processing steps (shown in FIGS. 23 and 24) that are performed by a shared computer, personal computer, and decryption computer in a system providing morbidity rates of predefined diseases.

In the information processing system, the processing program 13 recorded in the memory 7 of the shared computer 2, the processing program 27 recorded in the memory 23 of a personal computer 3, and the processing program 33 recorded in the memory 34 of the decryption computer S may perform information processing operations in accordance with the flowchart shown in FIGS. 23 and 24. In the flowchart shown in FIGS. 23 and 24, the processing steps marked "[Shared]" are performed by the shared computer 2; the processing steps marked "[Personal]" are performed by the personal computer 3; and the processing steps marked "[Decryption]" are performed by the decryption computer S. The sequence diagram shown in FIG. 25 illustrates an information process that is performed in accordance with the flowchart in FIGS. 23 and 24.

Step C1 (SC1) is first performed to start processing program 27, which is recorded in memory 23, so that the requester can use the information processing system. Processing program 27 drives the reading device 25 of the personal computer 3 to access the genome-related information recording medium 24 and read the "Gno.", which is recorded as data I on the genome-related information recording medium 24. The read "Gno." is then stored in memory section 26.

It is preferred that a password or biological information such as a fingerprint, for example, be used prior to step C1 for authentication in order to check whether or not the genome-related information recording medium 24 belongs to the requester.

In step C2 (SC2), the information that the requester wishes to receive, for example, the "colorectal cancer morbidity" (request information), is entered into the personal computer 3 in accordance with an on-screen image that is displayed on the display device 22 by processing program 27, and the personal computer 3 transmits the "colorectal cancer morbidity" and "Gno." to the shared computer 2 via the communication network 1.

In step C3 (SC3), the shared computer 2 receives the "colorectal cancer morbidity" and "Gno.", and then transmits the "Gno." and "differentiation information" to the personal computer 3 and decryption computer S. The shared computer 2 may transmit command information to the personal computer 3 in order to dictate the submission of "polymorphism patterns" corresponding to all the polymorphism addresses. In step C3, the information about the address of the decryption computer S may also be transmitted to the personal computer 3. Further, the personal computer may be instructed as needed, depending on the type of request information, to submit supplementary information such as an anamnesis and personal characteristics. The shared computer 2 stores the received "colorectal cancer morbidity" and "Gno." in memory section A 10 as request information.

In step C4 (SC4), the personal computer 3 receives the "Gno." and "differentiation information", and then transmits all the "polymorphism addresses", "Gno.", and "differentiation information" to the decryption computer S via the communication network 1. In other words, step C4 is performed so that the requester requests the decryption computer S to present the random numbers corresponding to all the "polymorphism addresses". Since the presentation of the random numbers corresponding to all the "polymorphism addresses" is requested in step C4, the transmission of "Gno." only to the decryption computer S is acceptable.

In step C5 (SC5), the decryption computer S receives the "Gno.", "polymorphism address", and "differentiation information" from the personal computer 3. Step C5 is performed so that the decryption computer S judges whether or not the received "Gno.", "polymorphism address", and "differentiation information" coincide with the "Gno.", "polymorphism address", and "differentiation information" that were transmitted from the shared computer 2 in step C3.

If it is judged that the "Gno.", "polymorphism address", and "differentiation information" received in step C5 coincide with the "Gno.", "polymorphism address", and "differentiation information" transmitted from the shared computer 2 in step C3, step C6 (SC6) is performed so that the processing program 33 for the decryption computer S operates to access the random number database 37. If, on the other hand, it is judged that the "Gno.", "polymorphism address", and "differentiation information" received in step C5 do not coincide with the "Gno.", "polymorphism address", and "differentiation information" transmitted from the shared computer 2 in step C3, the process for step C6 is not performed.

In step C7 (SC7), all the random numbers corresponding to the "polymorphism addresses" bound by the "Gno." received in step C5 are read from the random number database 37. The read random numbers are then associated with the "polymorphism addresses" and recorded in memory section 39. As a result, memory section 39 records the "Gno." of the requester as well as all the "polymorphism addresses" and "random numbers" for that "Gno.", which are associated with each other.

In step C8 (SC8), the decryption computer S transmits the "Gno.", "polymorphism address", and "random number" associated with the polymorphism address, which are recorded in memory section 39, to the personal computer 3 via the communication network 1. In step C8, the decryption computer S also transmits "billing information" and "identification number" to the shared computer 2. According to step C8, the shared computer 2 is billed, instead of the personal computer 3, for random number supply from the decryption computer S to the personal computer 3. The "differentiation information" and "billing information" may be transmitted to, for instance, a credit company instead of being directly transmitted to the shared computer 2 for the purpose of indirectly billing the shared computer 2 for random number supply. When the "differentiation information" and "billing information" are directly transmitted to the shared computer 2, the differentiation information is the "information about a direct billing destination". When, for instance, the differentiation information is transmitted to a credit company, it is the "information about an indirect billing destination".

In step C9 (SC9), the personal computer 3 receives the "Gno.", "polymorphism address", and "random number" that transmitted from the decryption computer S. The received "Gno.", "polymorphism address", and "random number" are then stored in memory section 26.

In step C10 (SC10), the processing program 27 for the personal computer 3 operates to access the genome-related information recording medium 24. In step C11 (SC11), all the "encrypted polymorphism patterns" are read from the data II recording on the genome-related information recording medium 24. The read "encrypted polymorphism patterns" are then associated with corresponding "polymorphism addresses" and recorded in memory section 26.

In step C12 (SC12), the processing program 27 for the personal computer 3 operates to access the decryption table 29. In step C13 (SC13), the random number received in step C9 is combined with the "encrypted polymorphism patterns" read in step C11, and the decryption table 29 is used to decrypt the "encrypted polymorphism patterns" to obtain the "polymorphism patterns". In other words, step C13 is performed so as to obtain the "polymorphism patterns" that correspond to all "polymorphism addresses". The obtained polymorphism patterns are associated with corresponding "polymorphism addresses" and recorded in memory section 26.

In step C14 (SC14), the personal computer 3 transmits the "Gno." recorded in memory section 26, all "polymorphism addresses", and "polymorphism patterns" associated with all polymorphism addresses to the shared computer 2 via the communication network 1.

In step C15 (SC15), the shared computer 2 receives the "Gno.", all the "polymorphism addresses", and "polymorphism patterns". The received "Gno.", "polymorphism addresses", and "polymorphism patterns" are then stored in memory section A 10 together with the request information that was recorded in memory section A 10 in step C3. In step C16 (SC16), the main database 14 is accessed in accordance with processing program 13.

In step C17 (SC17), the "category (disease name)" recordings in the main database 14 are searched in accordance with processing program 13 to extract a category (disease name) that matches the requested "colorectal cancer morbidity" (colorectal cancer).

In step C18 (SC18), the main database 14 is accessed in accordance with processing program 13 to read a "polymorphism address" classified as the "colorectal cancer" category, all the "polymorphism patterns" for the polymorphism address, and the "morbidity" of the polymorphism patterns. The read "polymorphism address", "polymorphism patterns", and "morbidity" are then stored in memory section A 10.

In step C19 (SC19), the data stored in memory section A 10 in step C18 is searched in accordance with the "polymorphism addresses" and "polymorphism patterns" received in step C15 in order to extract from memory section A 10 the morbidity associated with a polymorphism pattern that coincides with a received polymorphism pattern.

Next, step C20 (SC20) is performed so as to transmit the result of step C19, that is, the morbidity extracted depending on which polymorphism pattern in the main database 14 coincides with a polymorphism pattern contained in the information received in step C15, to the personal computer 3 via the communication network 1. In this instance, the shared computer 2 transmits the extracted morbidity together with the "Gno." of the requester.

In step C21 (SC21), the "Gno." and "morbidity" (semantic information) transmitted from the shared computer 2 are received. The received "Gno." and "morbidity" are then recorded in memory section 26. In this instance, the data I recording on the genome-related information recording medium 24 can be accessed to check whether or not the received "Gno." is correct.

In step C22 (SC22), the semantic information recorded in memory section 26 is used to display the colorectal cancer morbidity on the display device 22 in accordance with processing program 27. Instead of steps C20 through C22, which have been described above, the shared computer 2 may read (produce) a screen displaying semantic information in accordance with processing program 13 and cause the display device 22 of the personal computer 3 to display the read (produced) screen via the communication network 1. In this instance, too, it is assumed that the shared computer 2 transmits semantic information to the personal computer 3. This enables the requester to acquire the colorectal cancer morbidity by using the genome-related information 28 recorded on the genome-related information recording medium 24.

In the information processing system, too, the polymorphism pattern recordings on the genome-related information recording medium 24 are encrypted. Therefore, the polymorphism pattern could not possibly be deciphered even when the genome-related information recording medium 24 is stolen or otherwise lost. The polymorphism pattern is, by nature, specific to an individual, is highly confidential, and needs to be handled with great care. The information processing system can properly protect the information about a highly confidential polymorphism pattern and successfully prevent it from being illegally used by a third party. Spoofing and other similar deception can be avoided particularly if authentication is performed prior to step C1. As a result, illegal use can be prevented with increased certainty.

The information processing system, the requester does not need to transmit a "polymorphism address" related to request information to the decryption computer S. If a "polymorphism address" related to request information is transmitted to the decryption computer S via the communication network 1, the details of the request information might be identified in the event of illegal access or other contingency. In this instance, however, all the "random numbers" associated with the polymorphism address are requested. Therefore, the details of the request information will not possibly be identified even if illegal access or other contingency occurs in an information exchange between the decryption computer S and personal computer 3.

In the above case, the genome-related information 28 recorded on the genome-related information recording medium 24 is decrypted and then entirely output to the shared computer 2 so that the semantic information to be supplied to the requester is acquired in the shared computer 2. Therefore, if the flowchart shown in FIGS. 23 and 24 is followed, the requester can acquire the semantic information when a relatively small number of information exchange operations are performed between the personal computer 3 and shared computer 2. Consequently, when the flowchart is complied with, desired semantic information can be adequately obtained no matter whether the information processing capacity of the personal computer 3 is relatively small, and the requester can acquire the semantic information with extreme ease.

2. Second Embodiment

A second embodiment of the present invention will now be described. For the same configurations, operations, and terms as for the information processing system according to the first embodiment, like names, reference numerals, and definitions are used so that the configurations, operations, and terms will not repeatedly be explained. In the second embodiment, the shared computer 2 has the decryption table 29, which uses random numbers to decrypt encrypted polymorphism patterns. The decryption table 29 is recorded, for instance, in the database 8 or memory 7. The use of the decryption table 29 makes it possible to obtain "polymorphism patterns" by decrypting encrypted polymorphism patterns with corresponding random numbers.

Figure 26:
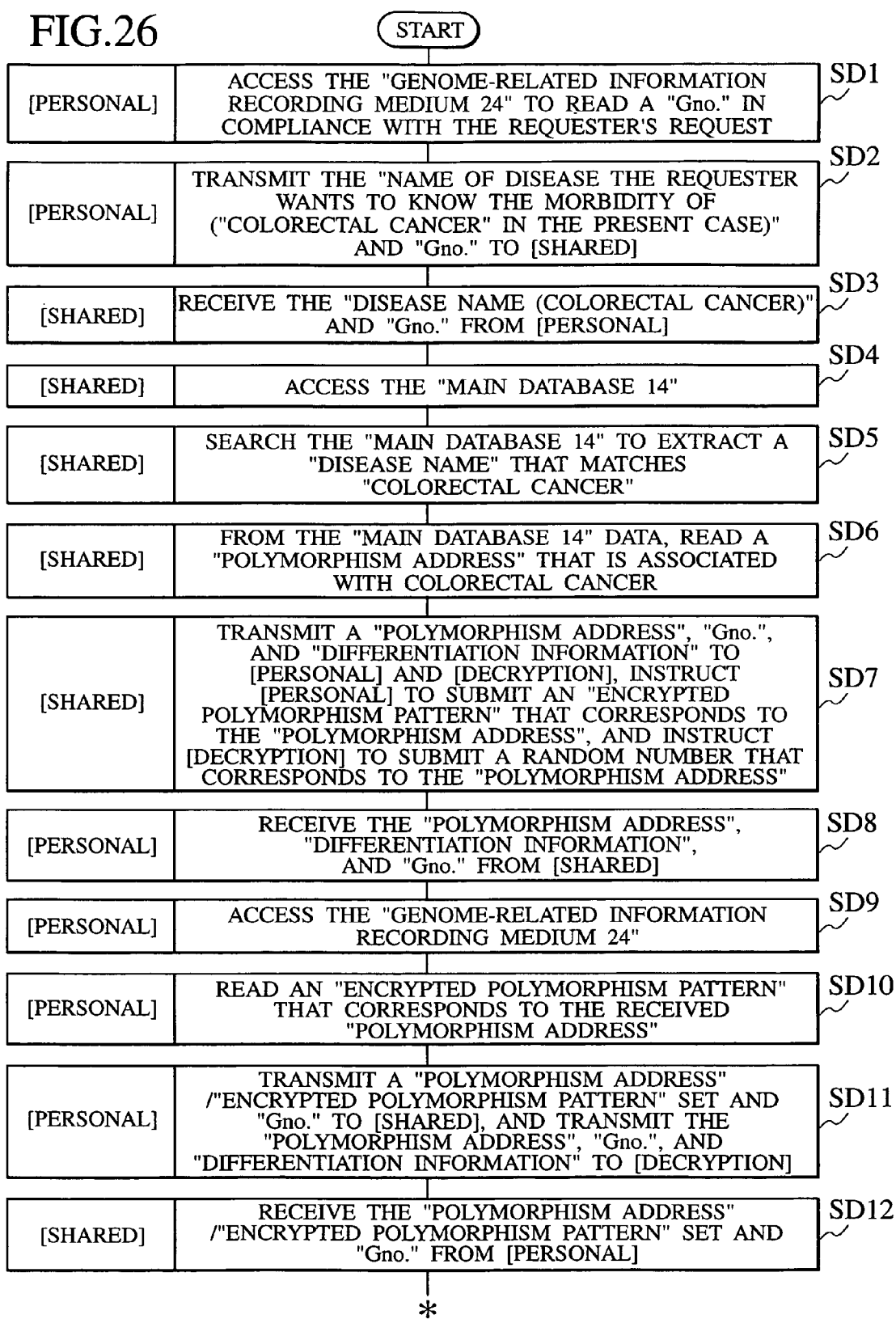
FIG. 26 is a flowchart further illustrating other processing steps that are performed by a shared computer, personal computer, and decryption computer in a system providing morbidity rates of predefined diseases.
Figure 27:
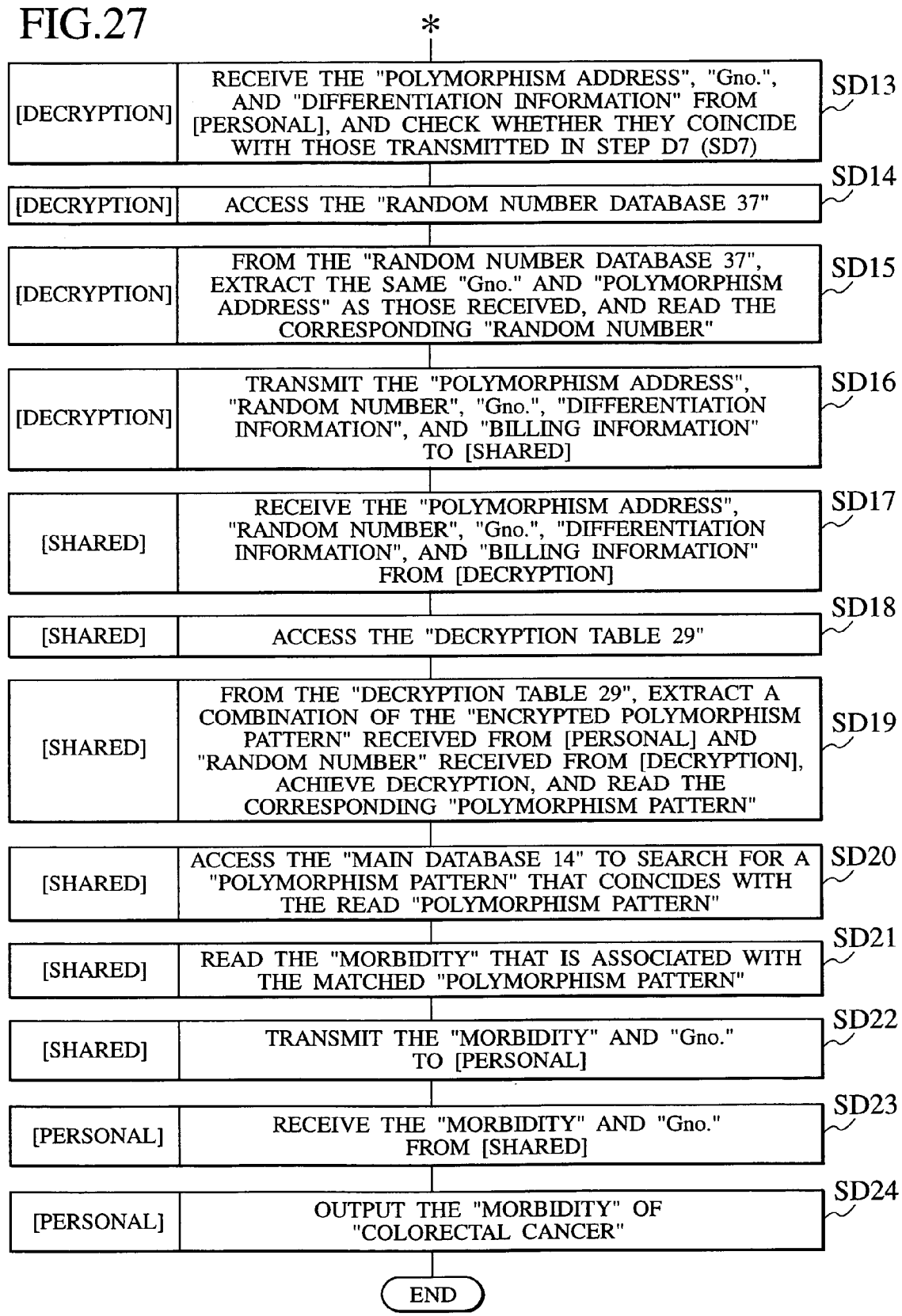
FIG. 27 is a flowchart that is a continuation of FIG. 26, which further illustrates other processing steps that are performed by a shared computer, personal computer, and decryption computer in a system providing morbidity rates of predefined diseases.
Figure 28:
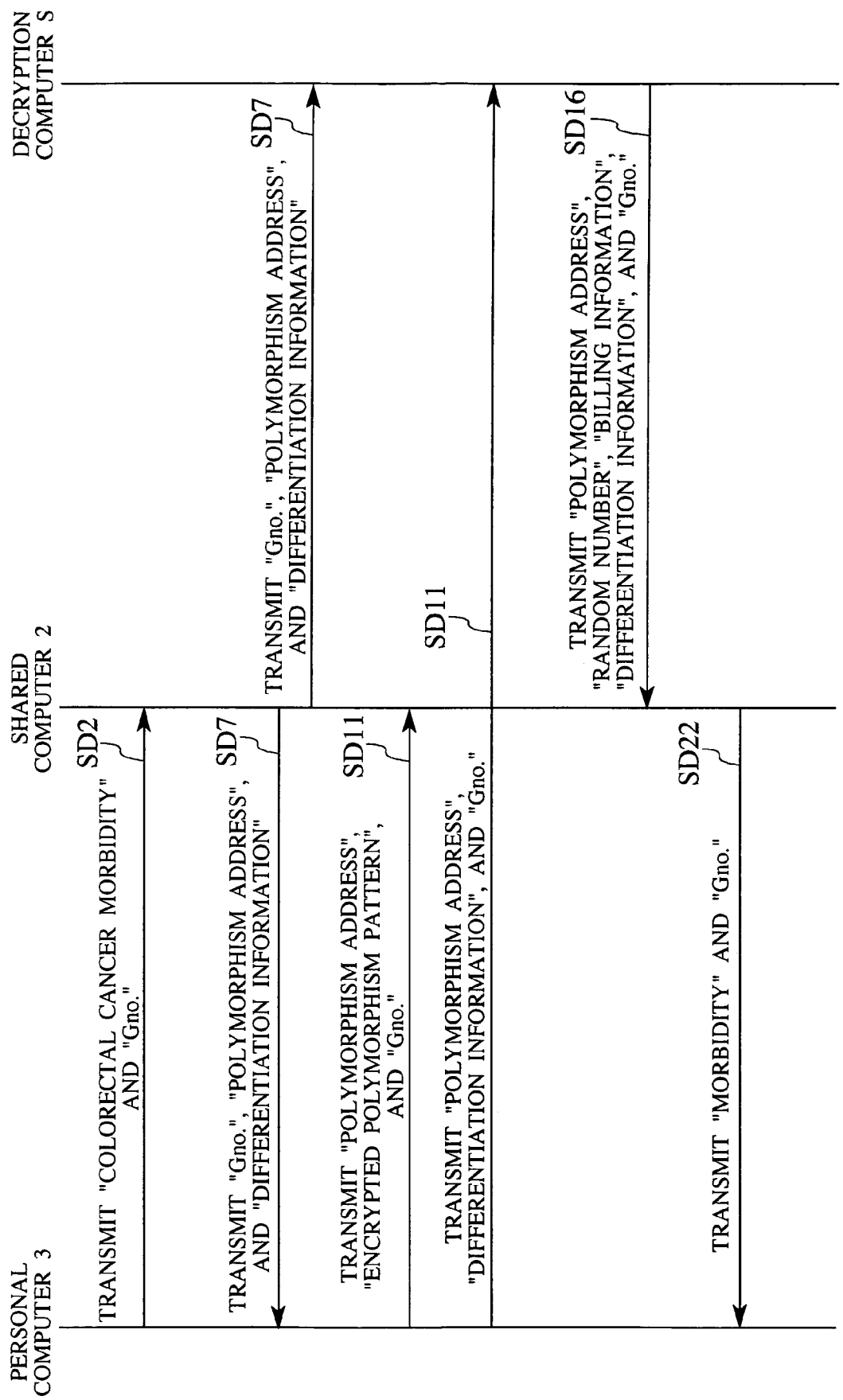
FIG. 28 is a sequence diagram further illustrating other processing steps (shown in FIGS. 26 and 27) that are performed by a shared computer, personal computer, and decryption computer in a system providing morbidity rates of predefined diseases.

In the information processing system, the processing program 13 recorded in the memory 7 of the shared computer 2, the processing program 27 recorded in the memory 23 of a personal computer 3, and the processing program 33 recorded in the memory 34 of the decryption computer S perform information processing operations in accordance, for instance, with the flowchart shown in FIGS. 26 and 27. In the flowchart shown in FIGS. 26 and 27, the processing steps marked "[Shared]" are performed by the shared computer 2; the processing steps marked "[Personal]" are performed by the personal computer 3; and the processing steps marked "[Decryption]" are performed by the decryption computer S. The sequence diagram shown in FIG. 28 illustrates an information process that is performed in accordance with the flowchart in FIGS. 26 and 27.

The information processing system is a system in which an individual who possesses the genome-related information recording medium 24 accesses the shared computer 2 via the communication network 1 by using the personal computer 3 and utilizes semantic information recorded in the main database 14 in the shared computer 2.

The genome-related information recording medium 24 may be produced in the same manner as described in conjunction with the first embodiment. In the second embodiment, too, a random number selected for encryption is associated with a polymorphism address for each "Gno.", which is specific to the genome-related information recording medium 24, and recorded in the random number database 37 of the decryption computer S for storage purposes.

The individual who uses the information processing system is a person who possesses the genome-related information recording medium 24 that contains an encrypted polymorphism pattern and is produced in the same manner as described in conjunction with the first embodiment. The individual who uses the information processing system (hereinafter referred to as the requester) first performs step D1 (SD1) to start processing program 27, which is recorded in the memory 23. Processing program 27 drives the reading device 25 for the personal computer 3, accesses the genome-related information recording medium 24, and reads a "Gno." that is recorded on the genome-related information recording medium 24 as data I. The read "Gno." is then stored in memory section 26.

It is preferred that a password or biological information such as a fingerprint, for example, be used prior to step D1 for authentication in order to check whether or not the genome-related information recording medium 24 belongs to the requester.

In step D2 (SD2), the information that the requester wishes to receive, for example, the "colorectal cancer morbidity" (request information), is entered into the personal computer 3 in accordance with an on-screen image that is displayed on the display device 22 by processing program 27, and the personal computer 3 transmits the "colorectal cancer morbidity" and "Gno." to the shared computer 2 via the communication network 1, or the personal computer 3 writes the "colorectal cancer morbidity" and "Gno." into the shared computer 2 via the communication network 1.

In step D3 (SD3), the shared computer 2 receives the "colorectal cancer morbidity" and "Gno.". The received "colorectal cancer morbidity" and "Gno." are then stored in memory section A 10 as request information. Next, step D4 (SD4) is performed to receive the request information and start processing program 13, which is stored in memory 7, to access the main database 14.

In step D5 (SD5), the "category (disease name)" recordings in the main database 14 are searched in accordance with processing program 13 to extract a category (disease name) that matches the requested "colorectal cancer morbidity" (colorectal cancer).

In step D6 (SD6), the "polymorphism address" associated with a "category (disease name)" (colorectal cancer) that matches the "colorectal cancer morbidity" is read from the data recorded in the main database 14. The read "polymorphism address" is stored in memory section A 10 as positional information associated with the request information. It means that memory section A 10 records the "colorectal cancer morbidity" and "polymorphism address" for a predetermined "Gno.".

In step D7 (SD7), the "Gno." "polymorphism address", and "differentiation information" recorded in memory section A 10 are transmitted to the personal computer 3 and decryption computer S. Step D7 is also performed to transmit command information to the personal computer 3 in order to dictate the submission of an "encrypted polymorphism pattern" corresponding to the transmitted "polymorphism address", and transmit command information to the decryption computer S in order to dictate the submission of a "random number" corresponding to the transmitted "polymorphism address".

In step D7, the information about the address of the decryption computer S may also be transmitted to the personal computer 3. In this instance, the personal computer 3 may be further instructed as needed, depending on the type of request information, to submit supplementary information such as an anamnesis and personal characteristics.

Next, step D8 (SD8) is performed to receive the "Gno.", "polymorphism address", and "differentiation information" that are transmitted from the shared computer 2. The received "Gno.", "polymorphism address", and "differentiation information" are then recorded in memory section 26. If the information about the address of the decryption computer S is received, the information is also recorded in memory section 26.

Next, step D9 (SD9) is performed in compliance with command information received in step D8 to access data II that is recorded on the genome-related information recording medium 24. In step D10 (SD10), the data II recordings on the genome-related information recording medium 24 are searched in accordance with processing program 27 to read an "encrypted polymorphism pattern" that corresponds to the "polymorphism address" received in step D8. The read "encrypted polymorphism pattern" is then associated with the corresponding "polymorphism address" and recorded in memory section 26. In this instance, it is preferred that data I be accessed to check whether or not the "Gno." received in step D8 is correct. Alternatively, step D10 may be performed to read both the polymorphism pattern and supplementary information recorded as data III, data IV, and data V and record them as needed in memory section 26.

In step D11 (SD11), the polymorphism address and encrypted polymorphism pattern temporarily recorded in memory section 26 and the supplementary information recorded as needed in memory section 26 are transmitted together with the "Gno." to the shared computer 2 via the communication network 1. Further, the "polymorphism address", "Gno.", and "differentiation information" temporarily recorded in memory section 26 are transmitted in step D11 to the decryption computer S via the communication network 1.

In step D12 (SD12), the shared computer 2 receives the polymorphism addresses, encrypted polymorphism patterns, "Gno.", and supplementary information that is recorded as needed. The requested polymorphism addresses and the encrypted polymorphism patterns at the respective polymorphism addresses are then recorded in memory section A 10.

Meanwhile, the decryption computer S receives the "polymorphism address", "Gno.", and "differentiation information" that were transmitted from the personal computer 3 in step D11, and then records them in memory section 39. Step D13 (SD13) is then performed to judge whether or not the received "Gno.", "polymorphism address", and "differentiation information" coincide with the "Gno.", "polymorphism address", and "differentiation information" that were transmitted from the shared computer 2 in step D7.

If it is judged that the "Gno.", "polymorphism address", and "differentiation information" transmitted from the personal computer 3 in step D11 coincide with the "Gno.", "polymorphism address", and "differentiation information" that were transmitted from the shared computer 2 in step D7, the processing program 33 for the decryption computer S operates in step D14 (SD14) to access the random number database 37. If, on the other hand, it is judged that the "Gno.", "polymorphism address", and "differentiation information" transmitted from the personal computer 3 in step D11 do not coincide with the "Gno.", "polymorphism address", and "differentiation information" that were transmitted from the shared computer 2 in step D7, the process for step D14 is not performed.

In step D15 (SD15), the "Gno."-bound random numbers received from the shared computer 2 and personal computer 3 are checked so as to read from the random number database 37 only the random numbers that correspond to the "polymorphism addresses" received from the shared computer 2 and personal computer 3. The read random numbers are then associated with the "polymorphism addresses" and recorded in memory section 39. As a result, memory section 39 records not only the "differentiation information" but also the "Gno." of the requester and the "polymorphism addresses" and "random numbers" for that "Gno.", which are associated with each other.

In step D16 (SD16), the decryption computer S transmits the "Gno.", "polymorphism address", "random number", "differentiation information", and "billing information", which are recorded in memory section 39, to the shared computer 2 via the communication network 1. Step D16 is performed so that the shared computer 2 is billed for the information supply fee relating to random numbers that are supplied from the decryption computer S to the shared computer 2 for the purpose of decrypting the encrypted polymorphism pattern transmitted from the personal computer 3 to the shared computer 2. The "differentiation information" and "billing information" may be transmitted to, for instance, a credit company instead of being directly transmitted to the shared computer 2 for the purpose of indirectly billing the shared computer 2 for the information supply fee relating to random number supply via the credit company. When the "differentiation information" and "billing information" are directly transmitted to the shared computer 2, the differentiation information is the "information about a direct billing destination". When, for instance, the differentiation information is transmitted to a credit company, it is the "information about an indirect billing destination".

In step D17 (SD17), the shared computer 2 receives the "Gno.", "polymorphism address", "random number", "differentiation information", and "billing information" that are transmitted from the decryption computer S. The received "Gno.", "polymorphism address", "random number", "differentiation information", and "billing information" are then stored in memory section A 10.

In step D18 (SD18), the processing program 13 for the shared computer 2 operates to access the decryption table 29. In step D19 (SD19), the "random number" received in step D17 is combined with the "encrypted polymorphism pattern" received in step D12, and the decryption table 29 is used to decrypt the "encrypted polymorphism pattern" to obtain the original "polymorphism pattern". It means that the "polymorphism pattern" corresponding to the "polymorphism address" read in step D6 can be obtained. The obtained polymorphism pattern is then associated with the corresponding "polymorphism address" and recorded in memory section A 10.

In step D20 (SD20), the main database 14 is accessed to search for a polymorphism address and polymorphism pattern that match the polymorphism address and polymorphism pattern obtained in step D19. More specifically, the main database 14, in which a plurality of polymorphism patterns are recorded for one polymorphism address, is searched to determine which polymorphism pattern in the main database 14 matches the received polymorphism address and its polymorphism pattern.

In step D21 (SD21), the morbidity of a colorectal cancer associated with the polymorphism pattern that matches the received polymorphism pattern is read in accordance with processing program 13. In other words, step D21 is performed so as to read the colorectal cancer morbidity of the requester in accordance with the polymorphism address and polymorphism pattern submitted by the requester. The read morbidity is then associated with the "Gno." of the requester and stored in memory section A 10. In this instance, the colorectal cancer morbidity may be stored after being corrected with supplementary information or after other information derived from the supplementary information is associated with the "Gno." of the requester.

In step D22 (SD22), the "Gno." and morbidity of the requester, which are stored in memory section A 10, are transmitted as semantic information to the personal computer 3 via the communication network 1. In step D23 (SD23), the personal computer 3 receives the "Gno." and morbidity (semantic information) of the requester. The received semantic information is then recorded in memory section 26.

Next, step D24 (SD24) is performed in compliance with processing program 27 so that the display device 22 displays the colorectal cancer morbidity according to the semantic information recorded in memory section 26. Instead of steps D22 through D24, the shared computer 2 may read (produce) a screen displaying semantic information in accordance with processing program 13 and cause the display device 22 of the personal computer 3 to display the read (produced) screen via the communication network 1. In this instance, too, it is assumed that the shared computer 2 transmits semantic information to the personal computer 3. This enables the requester to acquire the colorectal cancer morbidity by using the genome-related information 28 recorded on the genome-related information recording medium 24.

Particularly, in the information processing system according to the present embodiment, step D11 (SD11) is performed so that the polymorphism address the submission of which is dictated by the shared computer 2, its encrypted polymorphism pattern, and other relevant information are output together with the "Gno." to the shared computer 2 via the communication network 1 to obtain the information about colorectal cancer morbidity in step D23. In the information processing system, the encrypted polymorphism pattern is decrypted by the shared computer 2. Therefore, the information processing system does not need to perform a step for decrypting an encrypted polymorphism pattern in the personal computer 3. As a result, the information process to be performed by the personal computer 3 is simplified.

As is the case with the first embodiment described earlier, the present embodiment of the information processing system encrypts a polymorphism pattern recorded on the genome-related information recording medium 24. Therefore, the polymorphism pattern cannot be deciphered even when the genome-related information recording medium 24 is stolen or otherwise lost. Accordingly, the information processing system of the present embodiment can properly protect the information about a highly confidential polymorphism pattern and successfully prevent it from being illegally used by a third party. Spoofing and other similar deception can be avoided particularly if authentication is performed prior to step D1. As a result, illegal use can be prevented with increased certainty.

Further, the information processing system according to the present embodiment decrypts only the "encrypted polymorphism pattern" corresponding to the "polymorphism address" that is contained in the command information fed from the shared computer 2. Therefore, even if the shared computer 2 is illegally accessed or otherwise jeopardized, the possibility of polymorphism pattern leakage can be minimized.

Meanwhile, the information processing system according to the present embodiment requests, in step D7, the decryption computer S to present a "random number" that is associated with a polymorphism address contained in the command information for the purpose of decrypting an "encrypted polymorphism pattern" corresponding to the polymorphism address contained in the command information. However, the present invention is not limited to such a system and may alternatively be a system in which the shared computer 2 makes a request to the decryption computer S for all the "random numbers" associated with polymorphism addresses without regard to the polymorphism address contained in the command information.

In the above alternative system, the shared computer 2 does not need to transmit the "polymorphism address" contained in the command information to the decryption computer S in step D7. In this instance, all the "random numbers" associated with polymorphism addresses are requested. Therefore, when the decryption computer S and shared computer 2 exchange information, the type of information requested by the requester cannot possibly be identified even in the event of illegal access or other similar contingency.

In the above instance, it is preferred that the shared computer 2 achieve decryption by using only the "random number" related to the "polymorphism address" contained in the command information although there are various other "random numbers" associated with the polymorphism addresses that are obtained from the decryption computer S. In other words, it is preferred that only the "encrypted polymorphism pattern" received by the shared computer 2 in step D12 be decrypted.

In the above information processing system, command information is transmitted in step D7 to the decryption computer S to dictate the submission of a specified "random number" to the shared computer 2. However, the information processing system is not limited to a system in which the command information for the decryption computer S is transmitted in step D7. Alternatively, the personal computer 3 may transmit the command information to the decryption computer S, for instance, in step D11.

In the information processing system according to the present embodiment, the decryption computer S causes the shared computer 2 to pay the information supply fee for random number supply concerning a predetermined polymorphism address. In other words, when the decryption computer S supplies a predetermined random number to the shared computer 2, the information processing system assumes that a contract can be concluded between the decryption computer S and shared computer 2. When the contract is concluded, the shared computer 2 is obliged to pay for random number supply.

As indicated in the above-mentioned flowchart, the decryption computer S transmits "billing information" to the shared computer 2 in step D16. Alternatively, however, the decryption computer S may transmit the "billing information" to the shared computer 2 at any time after random number supply from the decryption computer S to the shared computer 2. Further, the "billing information" may be transmitted upon each transaction (random number supply). Another alternative is to record in a memory or the like the "billing information" about a plurality of transactions for a predetermined period of time, conduct a batch scan, statistically process the resulting information, and periodically transmit the processed information. The billed amount may also be varied in accordance with predefined rules (e.g., by reducing the amount by a predetermined percentage if a predetermined random number supply count is exceeded) and the statistically processed information (e.g., the cumulative number of random number supplies during a predetermined period of time). Further, the billed amount may be varied (e.g., by reducing the amount billed for random number supply for polymorphism addresses for which a predetermined count is exceeded) for each polymorphism address in accordance with predefined rules and the statistically processed information (e.g., the cumulative number of random number supplies for each polymorphism address during a predetermined period of time).

When the billed amount is varied for each polymorphism address in accordance with predefined rules, the "billing information" to be transmitted in step A15 may be the sum of billed amounts for each polymorphism address or may be not the sum but a list of billed amounts for each polymorphism address.

In the information processing system, the decryption computer S can properly bill the shared computer 2 because the information S verifies the reception of the "differentiation information" in step D12 and then transmits a random number in step D16.

As is the case with the first embodiment, the information processing of the present embodiment may perform step D7 so as to set, in accordance with predefined rules, an "anonymous polymorphism address" corresponding to a "polymorphism address" that is contained in the command information, and transmit to the personal computer 3 and/or decryption computer S the command information containing the "anonymous polymorphism address" that is associated with the "polymorphism address. In this case, the requester transmits, in step D11, the "Gno." and the association between the "anonymous polymorphism address" and "encrypted polymorphism pattern" to the shared computer 2 via the communication network 1. Further, the decryption computer S transmits, in step D16, the "anonymous polymorphism address" instead of a polymorphism address to the shared computer 2 via the communication network 1.

In the above instance, the personal computer 3 transmits neither a polymorphism address that directly represents the polymorphism pattern position within a genomic DNA nor an encrypted polymorphism pattern at such a polymorphism address. Further, the decryption computer S transmits neither a polymorphism address that directly represents the polymorphism pattern position within a genomic DNA nor a random number at such a polymorphism address. Since the anonymous polymorphism address does not directly represent the polymorphism pattern position within a genomic DNA, the positions of the encrypted polymorphism pattern and random number within a genomic DNA cannot be determined even when the information transmitted in steps D11 and D16 leaks outside in the event of a contingency. In other words, when an anonymous polymorphism address is used, the information processing system can prevent personal information leakage without using an advanced encryption technology. Consequently, the information transmitted by the information processing system in steps D11 and D16 cannot be used by anyone else. Thus, increased secrecy of personal information results.

The information processing system is not limited to an information process in which the shared computer 2 supplies semantic information and/or the information related to the semantic information to the personal computer 3 in accordance with the flowchart shown in FIGS. 26 and 27 and the sequence diagram shown in FIG. 28. Alternatively, the information processing system may perform an information process in accordance with a sequence diagram shown in FIG. 29 or 30.

Figure 29:
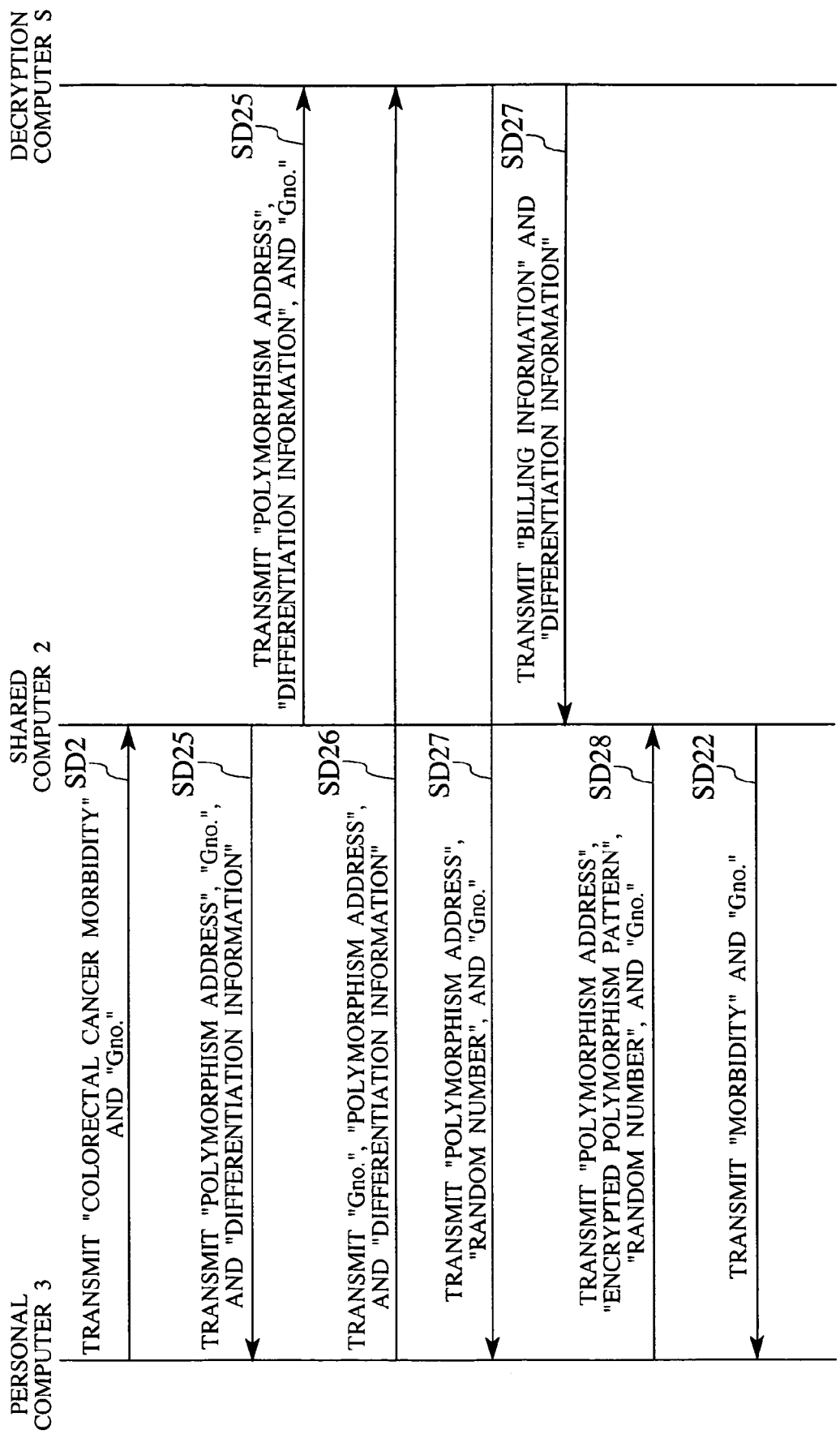
FIG. 29 is a sequence diagram further illustrating other processing steps that are performed by a shared computer, personal computer, and decryption computer in a system providing morbidity rates of predefined diseases.

When a method conforming to the sequence diagram shown in FIG. 29 is used, steps D1 through D6 are performed in the same manner as indicated in the flowchart shown in FIGS. 26 and 27, the "polymorphism address" associated with a "category (disease name)" (colorectal cancer) that matches the "colorectal cancer morbidity" is then read from the data that was recorded in the main database 14 in step D6, and, in step D25, the shared computer 2 transmits the requester's "Gno.", "differentiation number", and read "polymorphism address" to the decryption computer S, and transmits the "Gno.", "differentiation number", and read "polymorphism address" to the personal computer 3. In other words, step D25 is performed so that the shared computer 2 transmits the requester's "Gno." and read "polymorphism address" to the personal computer 3 for the purpose of requesting the presentation of an "encrypted polymorphism pattern" and "random number" corresponding to the transmitted "polymorphism address".

In step D26, the personal computer 3 receives the "Gno.", "differentiation number", and "polymorphism address" from the shared computer 2, and then transmits the received "Gno.", "differentiation number", and "polymorphism address" to the decryption computer S. In other words, step D26 is performed so that the personal computer 3 transmits the "Gno.", "differentiation number", and "polymorphism address" to the decryption computer S for the purpose of requesting the decryption computer S to present a "random number" corresponding to the "polymorphism address".

Next, the decryption computer S verifies that the "Gno.", "differentiation number", and "polymorphism address" transmitted from the personal computer 3 in step D26 coincide with the "Gno.", "differentiation number", and "polymorphism address" transmitted from the shared computer 2 in step D25. After verifying such a coincidence, the decryption computer S checks, in step D27, the random numbers bound by the "Gno." that was transmitted from the personal computer 3 in step D26, reads only the random number corresponding to the "polymorphism address" transmitted from the personal computer 3 in step D26, transmits the "Gno.", "polymorphism address", and read "random number" to the personal computer 3, and transmits "billing information" and "differentiation information" to the shared computer 2.

The personal computer 3 receives the "Gno.", "polymorphism address", and "random number" from the decryption computer S, and then accesses the genome-related information recording medium 24 under control of processing program 27 to read an "encrypted polymorphism pattern" corresponding to the "polymorphism address" received in step D26 from data II on the genome-related information recording medium 24. In step D28, the personal computer 3 transmits the "Gno.", "polymorphism address", "encrypted polymorphism pattern", and "random number" to the shared computer 2 via the communication network 1.

Subsequently, when steps D19 through D24 shown in the flowchart in FIGS. 26 and 27 are performed, the shared computer 2 supplies semantic information and/or the information related to the semantic information to the personal computer 3.

Figure 30:
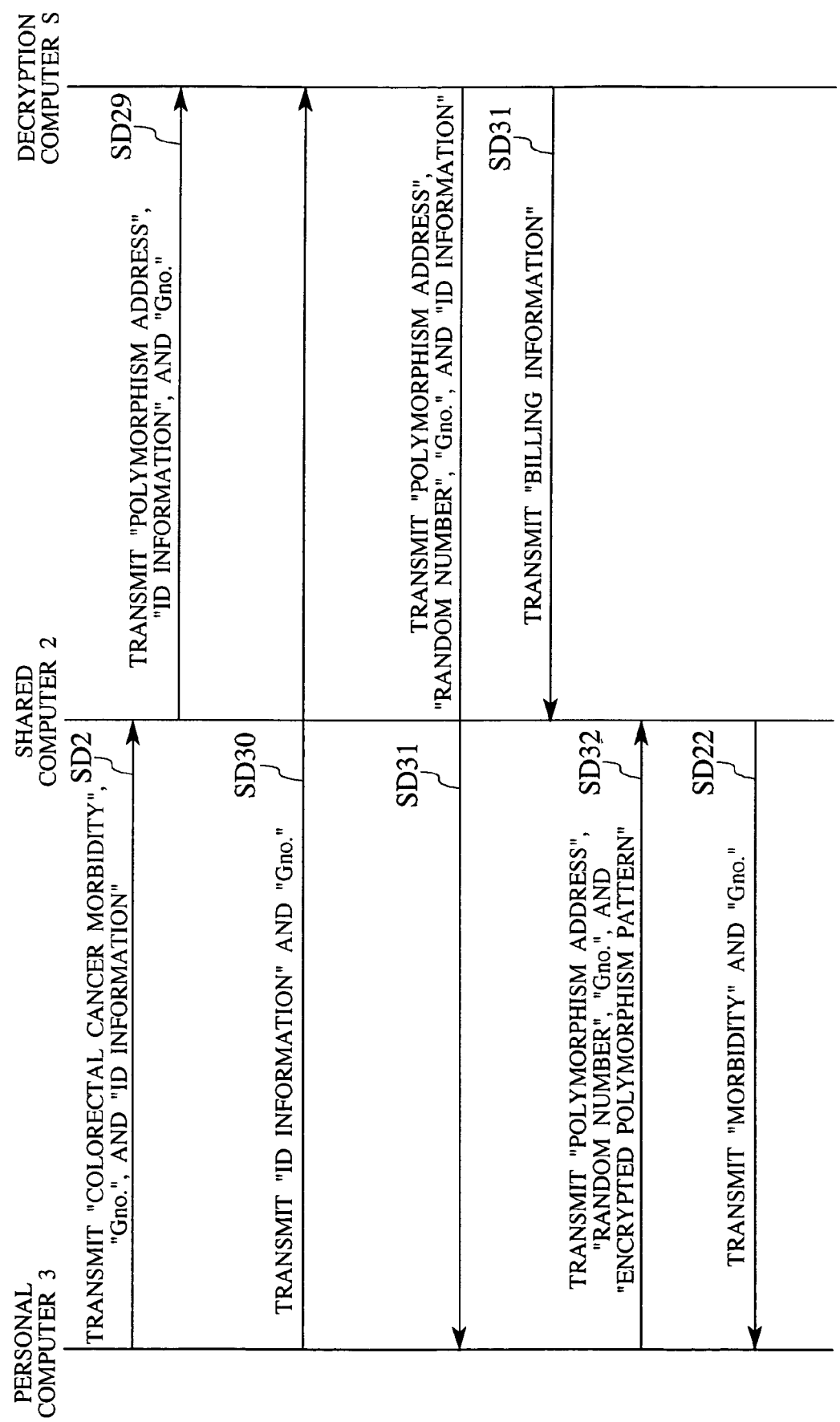
FIG. 30 is a sequence diagram further illustrating still other processing steps that are performed by a shared computer, personal computer, and decryption computer in a system providing morbidity rates of predefined diseases.

When a method conforming to the sequence diagram shown in FIG. 30 is used, step D2 shown in the flowchart in FIGS. 26 and 27 is first performed so that the personal computer 3 transmits "colorectal cancer morbidity", "Gno.", and "ID information" to the shared computer 2. Steps D3 through D6 are then performed in the same manner as indicated in the flowchart in FIGS. 26 and 27. After the "polymorphism address" associated with a "category (disease name)" (colorectal cancer) that matches the "colorectal cancer morbidity" is read from the data recordings in the main database 14 in step D6, step D29 is performed so that the shared computer 2 transmits the requester's "Gno.", "ID information", and read "polymorphism address" to the decryption computer S.

In step D30, the personal computer 3 transmits the "Gno." and "ID information" to the decryption computer S via the communication network 1. The decryption computer S then verifies that the "Gno." and "ID information" transmitted from the shared computer 2 in step D29 coincide with those transmitted from the personal computer 3 in step D30. Step D31 is then performed so that the decryption computer S checks the random numbers bound by the "Gno." that was transmitted from the shared computer 2 in step D29, reads only the random number corresponding to the "polymorphism address" transmitted from the shared computer 2 in step D29 from the random number database 37, transmits the "Gno.", "polymorphism address", read "random number", and "ID information" to the personal computer 3, and transmits "billing information" to the shared computer 2.

In other words, step D31 is performed so that the decryption computer S instructs the personal computer 3 to present to the shared computer 2 an "encrypted polymorphism pattern" and "random number" corresponding to the "polymorphism address" that was read by the shared computer 2 in step D6.

Next, the personal computer 3 receives the "Gno.", "polymorphism address", "random number", and "ID information" from the decryption computer S, and then accesses data II on the genome-related information recording medium 24 in accordance with the operation of processing program 27 to read an "encrypted polymorphism pattern" corresponding to the "polymorphism address" that was transmitted from the decryption computer S in step D31. In step D32, the personal computer 3 transmits the "Gno.", "polymorphism address", "encrypted polymorphism pattern" associated with the polymorphism address, and random number to the shared computer 2 via the communication network 1.

Subsequently, when steps D19 through D24 shown in the flowchart in FIGS. 26 and 27 are performed, the shared computer 2 supplies semantic information and/or the information related to the semantic information to the personal computer 3.

Figure 31:
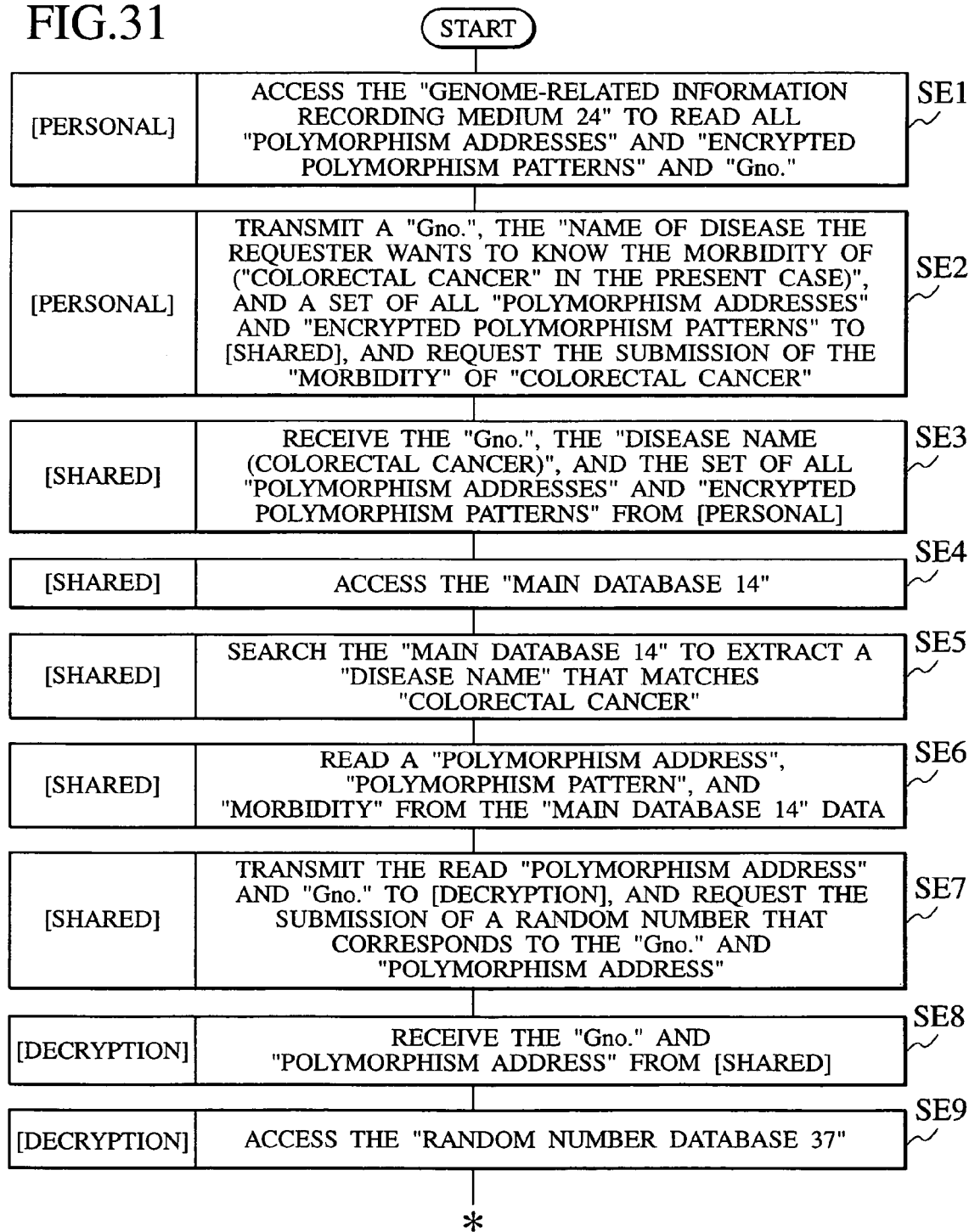
FIG. 31 is a flowchart illustrating still other processing steps that are performed by a shared computer, personal computer, and decryption computer in a system providing morbidity rates of predefined diseases.
Figure 32:
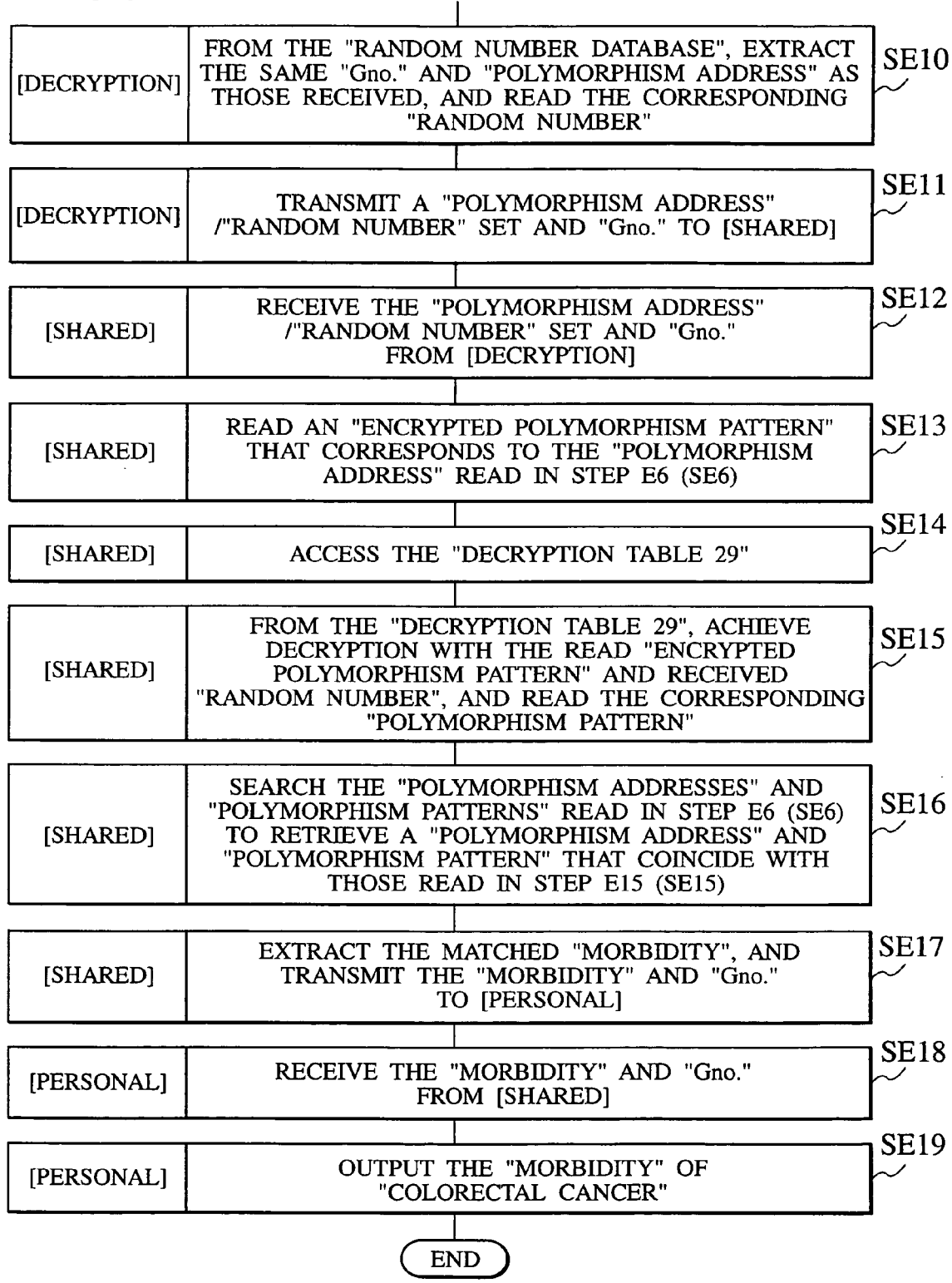
FIG. 32 is a flowchart that is a continuation of FIG. 31, which illustrates still other processing steps that are performed by a shared computer, personal computer, and decryption computer in a system providing morbidity rates of predefined diseases.

In the information processing system described above, the processing program 13 recorded in the memory 7 of the shared computer 2, the processing program 27 recorded in the memory 23 of the personal computer 3, and the processing program 33 recorded in the memory 34 of the decryption computer S may perform information processing operations in accordance, for instance, with the flowchart in FIGS. 31 and 32. In the flowchart shown in FIGS. 31 and 32, the processing steps marked "[Shared]" are performed by the shared computer 2; the processing steps marked "[Personal]" are performed by the personal computer 3; and the processing steps marked "[Decryption]" are performed by the decryption computer S.

Step E1 (SE1) is first performed to start processing program 27, which is recorded in memory 23, so that the requester can use the information processing system. Processing program 27 drives the reading device 25 of the personal computer 3 to access the genome-related information recording medium 24 and read the "Gno.", which is recorded as data I on the genome-related information recording medium 24, and all "polymorphism addresses" and "encrypted polymorphism patterns", which are recorded as data II on the same medium. The read "Gno.", "polymorphism addresses", and "encrypted polymorphism patterns" are then stored in memory section 26.

It is preferred that a password or biological information such as a fingerprint, for example, be used prior to step E1 for authentication in order to check whether or not the genome-related information recording medium 24 belongs to the requester.

In step E2 (SE2), the information that the requester wishes to receive, for example, the "colorectal cancer morbidity" (request information), is entered into the personal computer 3 in accordance with an on-screen image that is displayed on the display device 22 by processing program 27, and the personal computer 3 transmits the "colorectal cancer morbidity" as well as the "Gno.", "polymorphism addresses", and "encrypted polymorphism patterns", which are recorded in memory section 26, to the shared computer 2 via the communication network 1.

In step E3 (SE3), the shared computer 2 receives the "colorectal cancer morbidity", "Gno.", "polymorphism addresses", and "encrypted polymorphism patterns". The received "colorectal cancer morbidity" is then stored in memory section A 10 as the request information. The received "Gno." and all the "polymorphism addresses" and "encrypted polymorphism patterns" are also stored in memory section A 10. Upon receipt of the request information, the shared computer 2 starts processing program 13. Next, step E4 (SE4) is performed to access the main database 14 in accordance with processing program 13.

In step E5 (SE5), the "category (disease name)" recordings in the main database 14 are searched in accordance with processing program 13 to extract a "category (disease name)" that matches the requested "colorectal cancer morbidity" (colorectal cancer).

In step E6 (SE6), the main database 14 is accessed in accordance with processing program 13 to read a "polymorphism address" classified as the "colorectal cancer" category, all the "polymorphism patterns" for the polymorphism address, and the "morbidity" of the polymorphism patterns. The read "polymorphism address", "polymorphism patterns", and "morbidity" are then stored in memory section A 10.

In step E7 (SE7), the shared computer 2 transmits the "polymorphism address" read in step E6 and the "Gno." stored in memory section A 10 to the decryption computer S via the communication network 1. In other words, step E7 is performed so that the shared computer 2 requests the decryption computer S to present a random number corresponding to the "polymorphism address" that was read in step E6.

In step E8 (SE8), the decryption computer S receives the "Gno." and "polymorphism address" from the shared computer 2. In step E9 (SE9), the processing program 33 for the decryption computer S operates to access the random number database 37.

In step E10 (SE10), the random numbers bound by the "Gno." received in step E8 were checked to access the random number database 37 and read only the random number corresponding to the "polymorphism address" that was received in step E8. The read random number is then associated with the "Gno." and "polymorphism address" received in step E8 and stored in memory section 39. As a result, memory section 39 records the requester's "Gno." and stores the "polymorphism address" and "random number" that are associated with the "Gno.".

In step E11 (SE11), the decryption computer S transmits the "Gno.", "polymorphism address", and "random number" stored in memory section 39 to the shared computer 2 via the communication network 1. In step E12 (SE12), the shared computer 2 receives the "Gno.", "polymorphism address", and "random number" that are transmitted from the decryption computer S. The received "Gno.", "polymorphism address", and "random number" are then stored in memory section A 10.

In step E13 (SE13), all the "polymorphism addresses" and "encrypted polymorphism patterns" stored in step E3 are checked to read an "encrypted polymorphism pattern" that is associated with the "polymorphism address" read in step E6. In step E14 (SE14), the processing program 13 for the shared computer 2 operates to access the decryption table 29. In step E15 (SE15), the "random number" received in step E12 is combined with the "encrypted polymorphism pattern" read in step E13, and the decryption table 29 is used to decrypt the "encrypted polymorphism pattern" to obtain the original "polymorphism pattern". In other words, step E15 is performed so that a "polymorphism pattern" corresponding to the "polymorphism address" read in step E6 can be obtained. The obtained polymorphism pattern is associated with the corresponding "polymorphism address" and stored in memory section A 10.

In step E16 (SE16), the "polymorphism addresses" and "polymorphism patterns" read in step E6 are searched to retrieve the ones that match the "polymorphism address" and "polymorphism pattern" obtained in step E15. Next, step E17 (SE17) is performed to extract a morbidity in accordance with the result of step E16, that is, depending on whether or not the polymorphism pattern recorded in step E15 coincides with a polymorphism pattern read in step E6. More specifically, step E17 is performed to extract a morbidity that is associated with the matched polymorphism pattern. The extracted morbidity is then transmitted to the personal computer 3 via the communication network 1. In this instance, the shared computer 2 transmits the extracted morbidity together with the requester's "Gno.".

In step E18 (SE18), the personal computer 3 receives the "Gno." and semantic information containing "morbidity", which are transmitted from the shared computer 2. The received "Gno." and "morbidity" are then recorded in memory section 26. In this instance, the data I recording on the genome-related information recording medium 24 can be accessed to check whether or not the received "Gno." is correct.

In step E19 (SE19), the semantic information recorded in memory section 26 is used to display the colorectal cancer morbidity on the display device 22 in accordance with processing program 27. This enables the requester to obtain the colorectal cancer morbidity by using the genome-related information 28 recorded on the genome-related information recording medium 24.

Particularly, in the information processing system, step E2 (SE2) is performed so that all the polymorphism addresses, and their encrypted polymorphism patterns, and other relevant information are output together with the "Gno." to the shared computer 2 via the communication network 1, and step E18 is performed to obtain the information about colorectal cancer morbidity. Further, the encrypted polymorphism pattern is decrypted by the shared computer 2. In the information processing system, therefore, the personal computer 3 does not need to perform a step for decrypting an encrypted polymorphism pattern. As a result, the information process to be performed by the personal computer 3 is simplified.

The information processing system encrypts a polymorphism pattern recorded on the genome-related information recording medium 24. Therefore, the polymorphism pattern cannot be deciphered even when the genome-related information recording medium 24 is stolen or otherwise lost. Therefore, the information processing system can properly protect the information about a highly confidential polymorphism pattern and successfully prevent it from being illegally used by a third party. Spoofing and other similar deception can be avoided particularly if authentication is performed prior to step E1. As a result, illegal use can be prevented with increased certainty.

Meanwhile, the information processing system performs step E7 to request the decryption computer S to present a "random number" that is associated with the polymorphism address read in step E6 for the purpose of decrypting the "encrypted polymorphism pattern" that corresponds to the polymorphism address read in step E6. However, the present invention is not limited to such a system. Alternatively, the information processing system may a system in which, without regard to the polymorphism address read in step E6, the shared computer 2 requests the decryption computer S to present all the "random numbers" that are associated with polymorphism addresses.

In the above alternative system, the shared computer 2 does not need to transmit the "polymorphism address" read in step E6 to the decryption computer S. In this instance, all the "random numbers" associated with polymorphism addresses are requested. Therefore, when the decryption computer S and shared computer 2 exchange information, the type of information requested by the requester cannot possibly be identified even in the event of illegal access or other similar contingency.

In the above instance, it is preferred that the shared computer 2 achieve decryption by using only the "random number" related to the "polymorphism address" read in step E6 although there are various other "random numbers" associated with the polymorphism addresses that are obtained from the decryption computer S.

In the above example, the personal computer 3 submits all the "encrypted polymorphism patterns" to the shared computer 2, and the shared computer 2 requests the decryption computer S to submit a "random number". However, the present invention is not limited to such an example. The present invention can also be applied to a system in which the personal computer 3 submits all the "encrypted polymorphism patterns" and "random numbers" to the shared computer 2.

More specifically, in the above case, the requester accesses the decryption computer S prior to execution of step E2 and requests the submission of a "random number" that was used for polymorphism pattern encryption. In this instance, the decryption computer S extracts all the "random numbers" corresponding to the "Gno." that is unique to the requester, and transmits them to the personal computer 3 in the same manner as indicated in steps E8 through E11. Upon random number acquisition from the decryption computer S, the requester transmits, in step E2, the "random numbers" as well as a "polymorphism address", "encrypted polymorphism pattern", and other relevant information to the shared computer 2.

In the above case, the shared computer 2 receives the "polymorphism address", "encrypted polymorphism pattern", "random number", and other relevant information, and then performs steps E14 and beyond. This enables the requester to obtain the colorectal cancer morbidity by using the genome-related information 28 recorded on the genome-related information recording medium 24.

3. Third Embodiment

The third embodiment of the information processing system is the same as the first and second embodiments except that a "random number (cryptographic key)" is recorded on the genome-related information recording medium 24 and that an "encrypted polymorphism pattern" is recorded in the decryption computer S. Since the original "polymorphism pattern" can be obtained by means of decryption when the "random number" and "encrypted polymorphism pattern" can be combined, the "random number" and "encrypted polymorphism pattern" can be regarded as a pair that is required for polymorphism pattern decryption. It means that both the "random number" and "encrypted polymorphism pattern" are required to achieve polymorphism pattern decryption. Therefore, the information processing system remains essentially the same no matter whether the genome-related information recording medium 24 records a "random number" or "encrypted polymorphism pattern". In other words, the third embodiment of the information processing system in which the genome-related information recording medium 24 records a "random number (cryptographic key)" and the decryption computer S records an "encrypted polymorphism pattern" is essentially the same as the first and second embodiments.

In the third embodiment, the genome-related information 28 represents at least a "polymorphism address" and a "random number" at a predetermined polymorphism address, used for encrypting a "polymorphism pattern". The "polymorphism pattern" can be obtained as a result of genomic DNA analysis of an individual. Since the genome-related information 28 contains a "random number", the information derived from the genomic DNA analysis of an individual is not directly recorded. As is the case with the first and second embodiments, the genome-related information 28 may contain various information, including an anamnesis, personal characteristics, and clinical chart recordings.

Various items of genome-related information 28 are recorded on the genome-related information recording medium 24. As shown in FIG. 33, the genome-related information recording medium 24 records the individual's number "Gno.", which is peculiar to the genome-related information 28, as well as the individual's personal information, such as a birth date, as data I; polymorphism addresses and random numbers as data II; an anamnesis as data III; personal characteristics as data IV; and clinical chart recordings as data V. In other words, the genome-related information 28 includes data I, data II, data III, data IV, and data V. Data I and data II contain essential information, whereas data III, data IV, and data V include supplementary information.

The genome-related information 28 is recorded in such a manner that the "polymorphism address" corresponding to a position within a genomic DNA is linked with a "random number" for encrypting a polymorphism pattern at the polymorphism address. For data II, supplementary information about a specified polymorphism address may be recorded as a "comment" and linked with a "polymorphism address".

The random number is randomly selected for a specified polymorphism address and used for encrypting a polymorphism pattern at the specified polymorphism address. When, for instance, a random number is selected for a specified polymorphism address, it can be used to encrypt a polymorphism pattern at the polymorphism address in accordance with the "encryption table 40" shown in FIG. 9. The "encryption table 40" is a table for encrypting a specified "polymorphism pattern" to obtain an "encrypted polymorphism pattern" so that an "encrypted polymorphism pattern" can be derived from a "polymorphism pattern" and "random number".

In the present embodiment, the encrypted polymorphism pattern is recorded in an encrypted polymorphism pattern database 50 in the decryption computer S. As shown in FIG. 34, the encrypted polymorphism pattern database 50 records, for each genome-related information recording medium 24, the association between a "polymorphism address" and an "encrypted polymorphism pattern" that is encrypted with the above random number. In other words, the encrypted polymorphism pattern database records a "Gno.", which is unique to the genome-related information recording medium 24, and "encrypted polymorphism patterns" associated with a plurality of "Gno."-specific "polymorphism addresses".

Figure 9:
FIG. 9 illustrates a typical structure of data recorded in an encryption table.

When the genome-related information recording medium 24 is to be produced in the present embodiment, the genomic DNA of an individual is analyzed as is the case with the first embodiment, and then the resultant polymorphism pattern is encrypted with the "encryption table 40" shown in FIG. 9. Next, the polymorphism address and the random number used for encryption are associated with each other and recorded. Further, the "Gno.", which is unique to an individual, is set. The genome-related information recording medium 24 can then be produced. In this instance, the encrypted polymorphism pattern is associated with the "Gno." and recorded in an organization or the like having the decryption computer S to produce the encrypted polymorphism pattern database 50.

In the information processing system configured as described above, the shared computer 2 can supply semantic information and/or the information related to the semantic information to the personal computer 3 by changing the "encrypted polymorphism pattern" and "random number" shown in the flowcharts or sequence diagrams in FIGS. 10 through 32.

For example, in step A11 of the flowchart shown in FIGS. 10 and 11, the personal computer 3 requests the decryption computer S to submit an "encrypted polymorphism pattern" concerning a "polymorphism address" contained in command information. The decryption computer S then transmits the requested "encrypted polymorphism pattern" to the personal computer 3 from the encrypted polymorphism pattern database 50.

In step A19, the personal computer 3 accesses the decryption table 29 in accordance with the operation of processing program 27. In step A20, the "encrypted polymorphism pattern" received in step A16 is combined with the "random number" read from the genome-related information recording medium 24, and the "encrypted polymorphism pattern" is decrypted with the decryption table 29 to obtain the original "polymorphism pattern". In other words, step A20 is performed so that the "polymorphism pattern" corresponding to a "polymorphism address" contained in the command information can be obtained.

In the information processing system, which uses the genome-related information recording medium 24 on which random numbers and polymorphism addresses are associated with each other and recorded, an individual can use the semantic information recorded in the main database 14 via polymorphism addresses. Since the information processing system particularly records random numbers on the genome-related information recording medium 24, polymorphism patterns cannot possibly be deciphered even when the genome-related information recording medium 24 is stolen or otherwise lost. Therefore, the information processing system can properly protect the information about a highly confidential polymorphism pattern and successfully prevent it from being illegally used by a third party.

Further, when recording a random number on the genome-related information recording medium 24, the information processing system can handle a specified progression as one unit and set a random number by repeating such a unit. In such an instance, it is not necessary to set random numbers the number of which is appropriate for polymorphism addresses. Recording a specified progression, which is handled as a unit, and the repetition count of such a unit will suffice. Therefore, the random number data to be recorded on the genome-related information recording medium 24 can be compressed to a greater degree than encrypted polymorphism pattern recordings. Consequently, the present embodiment reduces the amount of data II on the genome-related information recording medium 24. As a result, the genome-related information recording medium 24 having a relatively small storage capacity can be used.

The information processing system decrypts only the "encrypted polymorphism pattern" corresponding to a "polymorphism address" that is contained in the command information fed from the shared computer 2. In other words, the information processing system does not decrypt all the "encrypted polymorphism patterns" that are contained in the encrypted polymorphism pattern database 50. Consequently, the possibility of polymorphism pattern leakage can be minimized even when the personal computer 3 is illegally accessed or otherwise jeopardized after step A16.

In the information processing system the decryption computer S is requested in step A11 to present an "encrypted polymorphism pattern" that is associated with a polymorphism address contained in command information for the purpose of decrypting an "encrypted polymorphism pattern" corresponding to a polymorphism address contained in the command information. However, the system is not limited to such a system. Alternatively, the information processing system may be a system in which the requester makes a request to the decryption computer S for all the "encrypted polymorphism patterns" associated with polymorphism addresses without regard to the polymorphism address contained in the command information.

The first to third embodiments of the information processing system according to the present invention have been described. However, the scope of the present invention is not limited to the foregoing embodiments.

For example, the foregoing descriptions of the first to third embodiments deal with the information processing system in which the shared computer 2, personal computer 3, and decryption computer S are interconnected so as to establish mutual data communication via the communication network 1, as shown in FIG. 1. However, the present invention can also be applied to an information processing system in which the decryption computer S is integrated with the shared computer 2 or personal computer 3. More specifically, the shared computer 2 or personal computer 3 can double as the decryption computer S when it incorporates a random number database or encrypted polymorphism pattern database. Even when an individual having the genome-related information recording medium 24 receives an object or service based on semantic information that is stored in the main database 14 of the shared computer 2, the information processing system configured as described above can properly protect the information about a highly confidential polymorphism pattern and successfully prevent it from being illegally used by a third party.

In the first to third embodiments, the service for indicating an individual's own morbidity of a specified disease is requested as a "request for an object and/or service". However, the "request for an object and/or service" is not limited to such a request. The present invention can also be applied, for instance, to a request for medicaments, foods, and other objects suitable for an individual's diathesis, a request for services for supplying medical examination items suitable for an individual's diathesis, and a request for foods suitable for an individual's diathesis as well as for services for supplying medical examination items suitable for an individual's diathesis.

In the first to third embodiments, the information processing system also supplies the "morbidity of a specified disease" as "semantic information". However, the present invention is not limited to such semantic information supply. Alternatively, the information processing system may not only supply the information about morbidity but also supply specific medical examination items (information related to semantic information) when the morbidity exceeds a predefined level.

Meanwhile, the information processing system may use a recording medium that has the entire information on the genome-related information recording medium except the information included in data II, that is, a recording medium that has data I in addition to data III and IV, which are added as supplementary information. In this case, the information included in data II is recorded in an external database (genome-related information recording medium) that is connected to the personal computer 3 via the communication network 1. When the information processing system is configured as described above, it is possible to access the external database via the communication network 1, read an "encrypted polymorphism pattern" or "random number" at a command-designated polymorphism address, associate the polymorphism address with the "encrypted polymorphism pattern" or "random number", and record them in memory section 26.

Further, in the information processing system, the requester may be without the genome-related information recording medium 24 or a recording medium having the entire information recording on the genome-related information recording medium except the information included in data II, and the information processing system may be provided with the genome-related information recording medium 24 that is connected to the personal computer 3 via the communication network 1. In this system, the requester can access the genome-related information recording medium 24 via the communication network 1 and download a "polymorphism address" and "encrypted polymorphism pattern", "random number", or other information recorded on the genome-related information recording medium 24 into the personal computer 3. In this case, the genome-related information recording medium 24 may be used to record the genome-related information about each of a plurality of individuals (each "Gno.").

Further, the present invention is not limited to a configuration in which the shared computer 2 includes the main database 14 as described earlier. The prevent invention can also be applied to an information processing system that is provided with the main database 14, which is connected to the shared computer 2 via the communication network 1.

Especially in the above case, the shared computer 2 can access a plurality of main databases 14 that are owned by different organizations or institutions, via the communication network 1, and use semantic information included in the plurality of main databases 14 to supply information to the requester. The information processing system then enables the requester to obtain information about colorectal cancer morbidity from the information included in the various main databases 14.

Further, the information processing system may transmit at least the request information received from the personal computer 3 to a so-called agent, and acquire semantic information ("colorectal cancer morbidity" in the foregoing embodiments) via the agent.

Furthermore, in the information processing system that has been described in conjunction with the foregoing embodiments, the shared computer 2 having the main database 14 supplies semantic information ("colorectal cancer morbidity" in the foregoing embodiments). However, the information processing system is not limited to such a system. Alternatively, the information processing system may include the personal computer 3, a first shared computer having a database in which polymorphism addresses are recorded according to a method that is capable of handling request information, a second shared computer having the main database 14, and the decryption computer.

In the above alternative configuration, the personal computer 3 transmits request information to the first shared computer, and the first shared computer reads a polymorphism address compliant with the request information, and a polymorphism pattern for a polymorphism address compliant with the request information is acquired from the personal computer 3. In the information processing system, the first shared computer accesses the main database 14 in the second shared computer and acquires semantic information and/or the information related to the semantic information in accordance with the polymorphism pattern obtained from the personal computer 3. More specifically, the second shared computer searches the main database 14 in accordance with the polymorphism pattern obtained from the first shared computer to retrieve the semantic information and/or the information related to the semantic information to be supplied to the personal computer 3.

In the above case, the second shared computer having the main database 14 acquires the semantic information and/or the information related to the semantic information without exchanging a polymorphism address and/or polymorphism pattern with the personal computer 3. On the other hand, the first shared computer, which does not have a main database 14, exchanges a polymorphism address and/or polymorphism pattern with the personal computer 3. In this case, therefore, a plurality of first shared computers can use the main database 14 in the second shared computer. Further, the requester can receive an object and/or service via the first shared computer when the second shared computer updates and otherwise manages the main database 14 and the first shared computer handles the requester's polymorphism address and/or polymorphism pattern. The object and/or service for the requester may be directly transmitted from the second shared computer. Further, the object and/or service may be transmitted not only to the requester but also to some other organization.

In the above case, either the first shared computer or second shared computer may incorporate the decryption table 29. If the first shared computer incorporates the decryption table 29, the first shared computer acquires the original polymorphism pattern by achieving decryption with an encrypted polymorphism pattern and cryptographic key. The first shared computer can then acquire semantic information and/or the information related to the semantic information by searching the main database 14 in the second shared computer in accordance with the obtained original polymorphism pattern.

If, on the other hand, the second shared computer incorporates the decryption table 29, the second shared computer acquires the original polymorphism pattern by achieving decryption with an encrypted polymorphism pattern and cryptographic key. The second shared computer can then acquire semantic information and/or the information related to the semantic information with the obtained original polymorphism pattern.

The present invention includes at least the following configurations:

[1] An information processing method concerning a nucleotide sequence, comprising the steps of:

acquiring positional information indicating a position within a nucleotide sequence in compliance with a request for an object or service;

reading encrypted nucleotide sequence-related information that corresponds to the acquired positional information;

acquiring a cryptographic key for decrypting the encrypted corresponding nucleotide sequence-related information and then decrypting the encrypted corresponding nucleotide sequence-related information with the acquired cryptographic key; and transmitting the resultant decrypted corresponding nucleotide sequence-related information.

[2] An information processing program concerning a nucleotide sequence for causing a computer to perform the procedures for:

acquiring, by transmission/reception means, positional information indicating a position within a nucleotide sequence in compliance with a request for an object or service;

reading, by reading means, encrypted nucleotide sequence-related information that corresponds to the acquired positional information;

acquiring, by reception means, a cryptographic key for decrypting the encrypted corresponding nucleotide sequence-related information and then decrypting, by control means, the encrypted corresponding nucleotide sequence-related information with the acquired cryptographic key; and transmitting, by transmission means, the resultant decrypted corresponding nucleotide sequence-related information.

[3] An information processing device concerning a nucleotide sequence, comprising:

reception means for acquiring positional information indicating a position within a nucleotide sequence in compliance with a request for an object or service;

reading means for reading encrypted nucleotide sequence-related information that corresponds to the acquired positional information;

control means for acquiring, by reception means, a cryptographic key for decrypting the encrypted corresponding nucleotide sequence-related information and decrypting the encrypted corresponding nucleotide sequence-related information with the acquired cryptographic key; and transmission means for transmitting the resultant decrypted corresponding nucleotide sequence-related information.

[4] An information processing method concerning a nucleotide sequence, comprising:

a first step for acquiring positional information indicating a position within a nucleotide sequence in compliance with a request for an object or service, a plurality of sets of nucleotide sequence-related information corresponding to the positional information, and a plurality of sets of semantic information associated respectively with the plurality of sets of the corresponding nucleotide sequence-related information;

a second step for reading encrypted nucleotide sequence-related information that corresponds to the acquired positional information;

a third step for acquiring a cryptographic key for decrypting the encrypted corresponding nucleotide sequence-related information and then decrypting the encrypted corresponding nucleotide sequence-related information with the acquired cryptographic key; and a fourth step for extracting the corresponding nucleotide sequence-related information acquired in the first step, which coincides with the decrypted corresponding nucleotide sequence-related information, and semantic information associated with the corresponding nucleotide sequence-related information.

[5] An information processing program concerning a nucleotide sequence for causing a computer to perform the procedures for:

acquiring, by transmission/reception means, positional information indicating a position within a nucleotide sequence in compliance with a request for an object or service, a plurality of sets of nucleotide sequence-related information corresponding to the positional information, and a plurality of sets of semantic information associated respectively with the plurality of sets of the corresponding nucleotide sequence-related information;

reading, by reading means, encrypted nucleotide sequence-related information that corresponds to the acquired positional information;

acquiring, by reception means, a cryptographic key for decrypting the encrypted corresponding nucleotide sequence-related information and then decrypting, by control means, the encrypted corresponding nucleotide sequence-related information with the acquired cryptographic key; and extracting, by control means, the acquired corresponding nucleotide sequence-related information, which coincides with the decrypted corresponding nucleotide sequence-related information, and semantic information associated with the corresponding nucleotide sequence-related information.

[6] An information processing device concerning a nucleotide sequence, comprising:

reception means for acquiring positional information indicating a position within a nucleotide sequence in compliance with a request for an object or service, a plurality of sets of nucleotide sequence-related information corresponding to the positional information, and a plurality of sets of semantic information associated respectively with the plurality of sets of the corresponding nucleotide sequence-related information;

reading means for reading encrypted nucleotide sequence-related information that corresponds to the acquired positional information;

control means for acquiring, by reception means, a cryptographic key for decrypting the encrypted corresponding nucleotide sequence-related information, decrypting the encrypted corresponding nucleotide sequence-related information with the acquired cryptographic key, and extracting the acquired corresponding nucleotide sequence-related information, which coincides with the decrypted corresponding nucleotide sequence-related information, and semantic information associated with the corresponding nucleotide sequence-related information.

[7] An information processing method concerning a nucleotide sequence, comprising the steps of:

reading positional information indicating a position within a nucleotide sequence and encrypted nucleotide sequence-related information corresponding to the positional information;

acquiring a cryptographic key for decrypting the read encrypted nucleotide sequence-related information and then decrypting the encrypted nucleotide sequence-related information with the acquired cryptographic key; and transmitting the decrypted nucleotide sequence-related information in correspondence with the positional information and transmitting a request for an object or service.

[8] An information processing program concerning a nucleotide sequence for causing a computer to perform the procedures for:

reading, by reading means, positional information indicating a position within a nucleotide sequence and encrypted nucleotide sequence-related information corresponding to the positional information;

acquiring, by reception means, a cryptographic key for decrypting the read encrypted nucleotide sequence-related information and then decrypting, by control means, the encrypted nucleotide sequence-related information with the acquired cryptographic key;

transmitting, by transmission means, the decrypted nucleotide sequence-related information in correspondence with the positional information; and transmitting, by transmission means, a request for an object or service.

[9] An information processing device concerning a nucleotide sequence, comprising:

reception means for reading positional information indicating a position within a nucleotide sequence and encrypted nucleotide sequence-related information corresponding to the positional information;

control means for acquiring, by reception means, a cryptographic key for decrypting the read encrypted nucleotide sequence-related information and then decrypting the encrypted nucleotide sequence-related information with the acquired cryptographic key; and transmission means for transmitting the decrypted nucleotide sequence-related information in correspondence with the positional information and transmitting a request for an object or service.

[10] An information processing method concerning a nucleotide sequence, comprising the steps of:

acquiring positional information indicating a position within a nucleotide sequence in compliance with a request for an object or service;

reading encrypted nucleotide sequence-related information that corresponds to the acquired positional information; and transmitting the read encrypted corresponding nucleotide sequence-related information in correspondence with the positional information or transmitting the read encrypted corresponding nucleotide sequence-related information and a cryptographic key used for nucleotide sequence-related information encryption in correspondence with the positional information.

[11] An information processing program concerning a nucleotide sequence for causing a computer to perform the procedures for:

acquiring, by transmission means, positional information indicating a position within a nucleotide sequence in compliance with a request for an object or service;

reading, by reading means, encrypted nucleotide sequence-related information that corresponds to the acquired positional information; and transmitting, by transmission means, the read encrypted corresponding nucleotide sequence-related information in correspondence with the positional information or transmitting the read encrypted corresponding nucleotide sequence-related information and a cryptographic key used for nucleotide sequence-related information encryption in correspondence with the positional information.

[12] An information processing device concerning a nucleotide sequence, comprising:

reception means for acquiring positional information indicating a position within a nucleotide sequence in compliance with a request for an object or service;

reading means for reading encrypted nucleotide sequence-related information that corresponds to the acquired positional information; and transmission means for transmitting the read encrypted corresponding nucleotide sequence-related information in correspondence with the positional information or transmitting the read encrypted corresponding nucleotide sequence-related information and a cryptographic key used for nucleotide sequence-related information encryption in correspondence with the positional information.

[13] An information processing method concerning a nucleotide sequence, comprising the steps of:

reading positional information indicating a position within a nucleotide sequence and encrypted nucleotide sequence-related information corresponding to the positional information; and transmitting the encrypted nucleotide sequence-related information in correspondence with the positional information or transmitting the read encrypted nucleotide sequence-related information and a cryptographic key used for nucleotide sequence-related information encryption in correspondence with the positional information, and transmitting a request for an object or service.

[14] An information processing program concerning a nucleotide sequence for causing a computer to perform the procedures for:

reading, by reading means, positional information indicating a position within a nucleotide sequence and encrypted nucleotide sequence-related information corresponding to the positional information;

transmitting, by transmission means, the encrypted nucleotide sequence-related information in correspondence with the positional information or transmitting the read encrypted nucleotide sequence-related information and a cryptographic key used for nucleotide sequence-related information encryption in correspondence with the positional information; and transmitting, by transmission means, a request for an object or service.

[15] An information processing device concerning a nucleotide sequence, comprising:

reading means for reading positional information indicating a position within a nucleotide sequence and encrypted nucleotide sequence-related information corresponding to the positional information; and transmission means for transmitting the encrypted nucleotide sequence-related information in correspondence with the positional information or transmitting the read encrypted nucleotide sequence-related information and a cryptographic key used for nucleotide sequence-related information encryption in correspondence with the positional information, and transmitting a request for an object or service.

[16] An information processing method concerning a nucleotide sequence, comprising the steps of:

receiving request information about a request for an object or service;

acquiring positional information compliant with the request information from storage means, which stores positional information indicating a position within a nucleotide sequence;

acquiring encrypted nucleotide sequence-related information that corresponds to the positional information acquired in compliance with the request information or acquiring the encrypted corresponding nucleotide sequence-related information and a cryptographic key for decrypting the encrypted corresponding nucleotide sequence-related information; and acquiring the cryptographic key if not acquired in the above step, and decrypting the encrypted corresponding nucleotide sequence-related information with the acquired cryptographic key or the cryptographic key acquired in the above step.

[17] An information processing program concerning a nucleotide sequence for causing a computer to perform the procedures for:

receiving, by reception means, request information about a request for an object or service;

acquiring, by reading means, positional information compliant with the request information from storage means, which stores positional information indicating a position within a nucleotide sequence;

acquiring, by reception means, encrypted nucleotide sequence-related information that corresponds to the positional information acquired in compliance with the request information or acquiring, by reception means, the encrypted corresponding nucleotide sequence-related information and a cryptographic key for decrypting the encrypted corresponding nucleotide sequence-related information; and acquiring, by reception means, the cryptographic key if not acquired in the above step, and decrypting, by control means, the encrypted corresponding nucleotide sequence-related information with the acquired cryptographic key or the cryptographic key acquired in the above step.

[18] An information processing device concerning a nucleotide sequence, comprising:

reception means for receiving request information about a request for an object or service;

storage means for storing positional information indicating a position within a nucleotide sequence;

reading means for acquiring positional information from the storage means in compliance with the request information;

transmission means for transmitting a submission command for dictating the submission of encrypted nucleotide sequence-related information corresponding the positional information acquired by the reading means and a submission command for dictating the submission of a cryptographic key for decrypting the encrypted corresponding nucleotide sequence-related information; and control means for acquiring, by the reception means, the encrypted corresponding nucleotide sequence-related information and the cryptographic key, and then decrypting the encrypted corresponding nucleotide sequence-related information with the cryptographic key.

[19] An information processing method concerning a nucleotide sequence, comprising the steps of:

receiving request information about a request for an object or service, positional information indicating a position within a nucleotide sequence, and encrypted nucleotide sequence-related information corresponding to the positional information or the encrypted nucleotide sequence-related information and a cryptographic key for decrypting the encrypted nucleotide sequence-related information; and acquiring the cryptographic key if not acquired in the above step, and decrypting at least part of the encrypted nucleotide sequence-related information with the acquired cryptographic key or the cryptographic key acquired in the above step.

[20] An information processing program concerning a nucleotide sequence for causing a computer to perform the procedures for:

receiving, by reception means, request information about a request for an object or service, positional information indicating a position within a nucleotide sequence, and encrypted nucleotide sequence-related information corresponding to the positional information or the encrypted nucleotide sequence-related information and a cryptographic key for decrypting the encrypted nucleotide sequence-related information; and acquiring the cryptographic key if not acquired in the above step, and decrypting, by control means, at least part of the encrypted nucleotide sequence-related information with the acquired cryptographic key or the cryptographic key acquired in the above procedure.

[21] An information processing device concerning a nucleotide sequence, comprising:

reception means for receiving request information about a request for an object or service, positional information indicating a position within a nucleotide sequence, encrypted nucleotide sequence-related information corresponding to the positional information, and a cryptographic key for decrypting the encrypted nucleotide sequence-related information; and control means for decrypting at least part of the encrypted nucleotide sequence-related information with the cryptographic key.

[22] An information processing method concerning a nucleotide sequence, comprising the steps of:

acquiring positional information indicating a position within a nucleotide sequence in compliance with a request for an object or service;

reading a cryptographic key used for encrypting nucleotide sequence-related information corresponding to the acquired positional information;

acquiring encrypted nucleotide sequence-related information corresponding to the acquired positional information and decrypting the encrypted corresponding nucleotide sequence-related information with the read cryptographic key; and transmitting the resultant decrypted corresponding nucleotide sequence-related information.

[23] An information processing program concerning a nucleotide sequence for causing a computer to perform the procedures for:

acquiring, by transmission means, positional information indicating a position within a nucleotide sequence in compliance with a request for an object or service;

reading, by reading means, a cryptographic key that was used to encrypt nucleotide sequence-related information corresponding to the acquired positional information;

acquiring, by reception means, encrypted nucleotide sequence-related information corresponding to the acquired positional information and decrypting, by control means, the encrypted corresponding nucleotide sequence-related information with the read cryptographic key; and transmitting, by transmission means, the resultant decrypted corresponding nucleotide sequence-related information.

[24] An information processing device concerning a nucleotide sequence, comprising:

reception means for acquiring positional information indicating a position within a nucleotide sequence in compliance with a request for an object or service;

reading means for reading a cryptographic key that was used to encrypt nucleotide sequence-related information corresponding to the acquired positional information;

control means for acquiring, by the reception means, encrypted nucleotide sequence-related information corresponding to the acquired positional information and decrypting the encrypted corresponding nucleotide sequence-related information with the read cryptographic key; and transmission means for transmitting the resultant decrypted corresponding nucleotide sequence-related information.

[25] An information processing method concerning a nucleotide sequence, comprising:

a first step for acquiring positional information indicating a position within a nucleotide sequence in compliance with a request for an object or service, a plurality of sets of nucleotide sequence-related information corresponding to the positional information, and a plurality of sets of semantic information associated respectively with the plurality of sets of the corresponding nucleotide sequence-related information;

a second step for reading a cryptographic key that was used to encrypt nucleotide sequence-related information corresponding to the acquired positional information;

a third step for acquiring encrypted nucleotide sequence-related information corresponding to the acquired positional information and decrypting the encrypted corresponding nucleotide sequence-related information with the read cryptographic key; and a fourth step for extracting the corresponding nucleotide sequence-related information acquired in the first step, which coincides with the decrypted corresponding nucleotide sequence-related information, and semantic information associated with the corresponding nucleotide sequence-related information.

[26] An information processing program concerning a nucleotide sequence for causing a computer to perform the procedures for:

acquiring, by reception means, positional information indicating a position within a nucleotide sequence in compliance with a request for an object or service, a plurality of sets of nucleotide sequence-related information corresponding to the positional information, and a plurality of sets of semantic information associated respectively with the plurality of sets of the corresponding nucleotide sequence-related information;

reading, by reading means, a cryptographic key that was used to encrypt nucleotide sequence-related information corresponding to the acquired positional information;

acquiring, by reception means, encrypted nucleotide sequence-related information corresponding to the acquired positional information and decrypting, by control means, the encrypted corresponding nucleotide sequence-related information with the read cryptographic key; and extracting, by control means, the acquired corresponding nucleotide sequence-related information, which coincides with the decrypted corresponding nucleotide sequence-related information, and semantic information associated with the corresponding nucleotide sequence-related information.

[27] An information processing device concerning a nucleotide sequence, comprising:

reception means for acquiring positional information indicating a position within a nucleotide sequence in compliance with a request for an object or service, a plurality of sets of nucleotide sequence-related information corresponding to the positional information, and a plurality of sets of semantic information associated respectively with the plurality of sets of the corresponding nucleotide sequence-related information;

reading means for reading a cryptographic key that was used to encrypt nucleotide sequence-related information corresponding to the acquired positional information; and control means for acquiring, by the reception means, encrypted nucleotide sequence-related information corresponding to the acquired positional information, decrypting the encrypted corresponding nucleotide sequence-related information with the read cryptographic key, and extracting the corresponding nucleotide sequence-related information acquired by the reception means, which coincides with the decrypted corresponding nucleotide sequence-related information, and semantic information associated with the corresponding nucleotide sequence-related information.

[28] An information processing method concerning a nucleotide sequence, comprising the steps of:

reading a cryptographic key that was used to encrypt nucleotide sequence-related information in correspondence with positional information indicating a position within a nucleotide sequence;

acquiring nucleotide sequence-related information that is encrypted with the cryptographic key, and decrypting the encrypted nucleotide sequence-related information with the read cryptographic key; and transmitting the resultant decrypted nucleotide sequence-related information in correspondence with the positional information and transmitting a request for an object or service.

[29] An information processing program concerning a nucleotide sequence for causing a computer to perform the procedures for:

reading, by reading means, a cryptographic key that was used to encrypt nucleotide sequence-related information in correspondence with positional information indicating a position within a nucleotide sequence;

acquiring, by reception means, nucleotide sequence-related information that is encrypted with the cryptographic key, and decrypting, by control means, the nucleotide sequence-related information that is encrypted with the read cryptographic key;

transmitting, by transmission means, the decrypted nucleotide sequence-related information in correspondence with the positional information; and transmitting, by transmission means, a request for an object or service.

[30] An information processing device concerning a nucleotide sequence, comprising:

reading means for reading a cryptographic key that was used to encrypt nucleotide sequence-related information in correspondence with positional information indicating a position within a nucleotide sequence;

reception means for acquiring nucleotide sequence-related information that is encrypted with the cryptographic key;

control means for decrypting the encrypted nucleotide sequence-related information with the read cryptographic key; and transmission means for transmitting the resultant decrypted nucleotide sequence-related information in correspondence with the positional information and transmitting a request for an object or service.

[31] An information processing method concerning a nucleotide sequence, comprising the steps of:

acquiring positional information indicating a position within a nucleotide sequence in compliance with a request for an object or service;

reading a cryptographic key that was used to encrypt nucleotide sequence-related information corresponding to the acquired positional information; and transmitting the read cryptographic key in correspondence with the positional information or transmitting the read cryptographic key and encrypted corresponding nucleotide sequence-related information in correspondence with the positional information.

[32] An information processing program concerning a nucleotide sequence for causing a computer to perform the procedures for:

acquiring, by reception means, positional information indicating a position within a nucleotide sequence in compliance with a request for an object or service;

reading, by reading means, a cryptographic key that was used to encrypt nucleotide sequence-related information corresponding to the acquired positional information; and transmitting, by transmission means, the read cryptographic key in correspondence with the positional information or transmitting the read cryptographic key and encrypted corresponding nucleotide sequence-related information in correspondence with the positional information.

[33] An information processing device concerning a nucleotide sequence, comprising:

reception means for acquiring positional information indicating a position within a nucleotide sequence in compliance with a request for an object or service;

reading means for reading a cryptographic key that was used to encrypt nucleotide sequence-related information corresponding to the acquired positional information; and transmission means for transmitting the read cryptographic key in correspondence with the positional information or transmitting the read cryptographic key and encrypted corresponding nucleotide sequence-related information in correspondence with the positional information.

[34] An information processing method concerning a nucleotide sequence, comprising the steps of:

reading positional information indicating a position within a nucleotide sequence and a cryptographic key that was used to encrypt nucleotide sequence-related information in correspondence with the positional information; and transmitting the read cryptographic key in correspondence with the positional information or transmitting encrypted nucleotide sequence-related information and the cryptographic key used to encrypt the read nucleotide sequence-related information in correspondence with the positional information, and transmitting a request for an object or service.

[35] An information processing program concerning a nucleotide sequence for causing a computer to perform the procedures for:

reading, by reading means, positional information indicating a position within a nucleotide sequence and a cryptographic key that was used to encrypt nucleotide sequence-related information in correspondence with the positional information;

transmitting, by transmission means, the read cryptographic key in correspondence with the positional information or transmitting encrypted nucleotide sequence-related information and the cryptographic key used to encrypt the read nucleotide sequence-related information in correspondence with the positional information; and transmitting, by transmission means, a request for an object or service.

[36] An information processing device concerning a nucleotide sequence, comprising:

reading means for reading positional information indicating a position within a nucleotide sequence and a cryptographic key that was used to encrypt nucleotide sequence-related information in correspondence with the positional information; and transmission means for transmitting the read cryptographic key in correspondence with the positional information or transmitting encrypted nucleotide sequence-related information and the cryptographic key used to encrypt the read nucleotide sequence-related information in correspondence with the positional information, and transmitting a request for an object or service.

[37] An information processing method concerning a nucleotide sequence, comprising the steps of:

receiving request information about a request for an object or service;

acquiring positional information compliant with the request information from storage means, which stores positional information indicating a position within a nucleotide sequence;

acquiring a cryptographic key that was used for nucleotide sequence-related information encryption and in correspondence with positional information acquired in compliance with the request information or acquiring the cryptographic key and encrypted nucleotide sequence-related information corresponding to the positional information acquired in compliance with the request information; and acquiring the encrypted corresponding nucleotide sequence-related information if not acquired in the above step, and decrypting the acquired encrypted corresponding nucleotide sequence-related information or the encrypted corresponding nucleotide sequence-related information acquired in the above step with the cryptographic key.

[38] An information processing program concerning a nucleotide sequence for causing a computer to perform the procedures for:

receiving, by reception means, request information about a request for an object or service;

acquiring, by reading means, positional information compliant with the request information from storage means, which stores positional information indicating a position within a nucleotide sequence;

acquiring, by reception means, a cryptographic key that was used for nucleotide sequence-related information encryption and in correspondence with positional information acquired in compliance with the request information or acquiring, by reception means, the cryptographic key and encrypted nucleotide sequence-related information corresponding to the positional information acquired in compliance with the request information; and acquiring, by reception means, the encrypted corresponding nucleotide sequence-related information if not acquired in the above procedure, and decrypting, by control means, the acquired encrypted corresponding nucleotide sequence-related information or the encrypted corresponding nucleotide sequence-related information acquired in the above procedure with the cryptographic key.

[39] An information processing device concerning a nucleotide sequence, comprising:

reception means for receiving request information about a request for an object or service;

storage means for storing positional information indicating a position within a nucleotide sequence;

reading means for acquiring positional information compliant with the request information from the storage means;

transmission means for transmitting a submission command for dictating the submission of a cryptographic key that was used for encrypting nucleotide sequence-related information corresponding the positional information acquired by the reading means, and transmitting a submission command for dictating the submission of corresponding nucleotide sequence-related information encrypted with the cryptographic key; and control means for acquiring, by the reception means, the cryptographic key and the encrypted corresponding nucleotide sequence-related information, and then decrypting the encrypted corresponding nucleotide sequence-related information with the cryptographic key.

[40] An information processing method concerning a nucleotide sequence, comprising the steps of:

receiving request information about a request for an object or service, positional information indicating a position within a nucleotide sequence, and a cryptographic key that was used for encrypting nucleotide sequence-related information corresponding to the positional information or the cryptographic key and nucleotide sequence-related information encrypted with the cryptographic key; and acquiring the encrypted nucleotide sequence-related information if not acquired in the above step, and decrypting the acquired encrypted nucleotide sequence-related information or at least part of the encrypted nucleotide sequence-related information obtained in the above step with the cryptographic key.

[41] An information processing program concerning a nucleotide sequence for causing a computer to perform the procedures for:

receiving, by reception means, request information about a request for an object or service, positional information indicating a position within a nucleotide sequence, and a cryptographic key that was used for encrypting nucleotide sequence-related information corresponding to the positional information or the cryptographic key and nucleotide sequence-related information encrypted with the cryptographic key; and acquiring the encrypted nucleotide sequence-related information if not acquired in the above step, and decrypting, by control means, the acquired encrypted nucleotide sequence-related information or at least part of the encrypted nucleotide sequence-related information obtained in the above procedure with the cryptographic key.

[42] An information processing device concerning a nucleotide sequence, comprising:

reception means for receiving request information about a request for an object or service, positional information indicating a position within a nucleotide sequence, a cryptographic key that was used for encrypting nucleotide sequence-related information corresponding to the positional information, and nucleotide sequence-related information encrypted with the cryptographic key; and control means for decrypting at least part of the encrypted nucleotide sequence-related information with the cryptographic key.

[43] An information processing method concerning a nucleotide sequence, comprising:

a first step for acquiring positional information indicating a position within a nucleotide sequence and a cryptographic key that was used for nucleotide sequence-related information encryption or nucleotide sequence-related information encrypted with the cryptographic key, associating the positional information with the cryptographic key or the encrypted nucleotide sequence-related information, and storing the resulting association in storage means; and a second step for reading specified positional information and a cryptographic key associated with the positional information or the nucleotide sequence-related information encrypted with the cryptographic key from the storage means, and transmitting the read combination.

[44] An information processing program concerning a nucleotide sequence for causing a computer to perform:

a first procedure for acquiring positional information indicating a position within a nucleotide sequence and a cryptographic key that was used for nucleotide sequence-related information encryption or nucleotide sequence-related information encrypted with the cryptographic key, associating the positional information with the cryptographic key or the encrypted nucleotide sequence-related information, and storing the resulting association in storage means; and a second procedure for reading specified positional information and a cryptographic key associated with the positional information or the nucleotide sequence-related information encrypted with the cryptographic key from the storage means, and transmitting the read combination.

[45] An information processing device concerning a nucleotide sequence, comprising:

storage means for storing positional information indicating a position within a nucleotide sequence and a cryptographic key that was used for nucleotide sequence-related information encryption or nucleotide sequence-related information encrypted with the cryptographic key;

reading means for reading specified positional information and a cryptographic key associated with the positional information or nucleotide sequence-related information encrypted with the cryptographic key from the storage means; and transmission means for transmitting the specified positional information read by the reading means and the cryptographic key associated with the positional information or the nucleotide sequence-related information encrypted with the cryptographic key.

[46] An information processing method concerning a nucleotide sequence, comprising:

a first step for acquiring positional information indicating a position within a nucleotide sequence and a cryptographic key that was used for nucleotide sequence-related information encryption or nucleotide sequence-related information encrypted with the cryptographic key, associating the positional information with the cryptographic key or the encrypted nucleotide sequence-related information, and storing the resulting association in storage means;

a second step for extracting specified positional information and a cryptographic key associated with the positional information or encrypted nucleotide sequence-related information from the storage means;

a third step for acquiring encrypted nucleotide sequence-related information associated with specified positional information if the specified positional information and the cryptographic key are extracted in the second step, or acquiring the cryptographic key associated with specified positional information if the specified positional information and encrypted nucleotide sequence-related information are extracted in the second step;

a fourth step for decrypting the encrypted nucleotide sequence-related information with the cryptographic key and encrypted nucleotide sequence-related information; and a fifth step for associating the positional information with the decrypted nucleotide sequence-related information and transmitting the resulting association.

[47] An information processing program concerning a nucleotide sequence for causing a computer to perform:

a first procedure for acquiring positional information indicating a position within a nucleotide sequence and a cryptographic key that was used for nucleotide sequence-related information encryption or nucleotide sequence-related information encrypted with the cryptographic key, associating the positional information with the cryptographic key or the encrypted nucleotide sequence-related information, and storing, by storage means, the resulting association;

a second procedure for extracting, by control means, specified positional information and a cryptographic key associated with the positional information or encrypted nucleotide sequence-related information from the storage means;

a third procedure for acquiring, by reception means, encrypted nucleotide sequence-related information associated with specified positional information if the specified positional information and the cryptographic key are extracted in the second procedure, or acquiring, by reception means, the cryptographic key associated with specified positional information if the specified positional information and encrypted nucleotide sequence-related information are extracted in the second procedure;

a fourth procedure for decrypting, by control means, the encrypted nucleotide sequence-related information with the cryptographic key and encrypted nucleotide sequence-related information; and a fifth procedure for associating the positional information with the decrypted nucleotide sequence-related information and transmitting the resulting association by transmitting means.

[48] An information processing device concerning a nucleotide sequence, comprising:

storage means for associating positional information indicating a position within a nucleotide sequence and a cryptographic key that was used for encrypting nucleotide sequence-related information for a position indicated by the positional information or nucleotide sequence-related information encrypted with the cryptographic key, and storing the resulting association;

reception means for acquiring encrypted nucleotide sequence-related information associated with positional information if the positional information and cryptographic key are stored in the storage means or acquiring a cryptographic key that is associated with positional information if the positional information and encrypted nucleotide sequence-related information are stored in the storage means;

control means for decrypting the encrypted nucleotide sequence-related information with the cryptographic key and the encrypted nucleotide sequence-related information; and transmission means for associating the positional information and the decrypted nucleotide sequence-related information and transmitting the resulting association.

INDUSTRIAL APPLICABILITY

As described in detail above, the present invention applies to an information processing system that effectively uses nucleotide sequence information differences between individual organisms to offer semantic information useful for each individual organism, and provides a highly-safe information processing system that is capable of properly preventing leakage and illegal use of nucleotide sequence information.

The invention claimed is:

1. An information processing method concerning a nucleotide sequence, wherein the method is executed within a system that comprises a first computer, an information provision computer for decryption, and a second computer, which are connected to each other via a communication network, wherein the first computer comprises a transmitter/receiver and a processor, and is permitted to access a first memory area storing positional information indicating a position within a nucleotide sequence and either encrypted nucleotide sequence-related information or a cryptographic key regarding an individual, the encrypted nucleotide sequence-related information or the cryptographic key being set for at least one of a plurality of positions, and is capable of using information for decryption of the encrypted nucleotide sequence-related information based on the cryptographic key; and wherein the information provision computer for decryption is permitted to access a second memory area storing positional information and the encrypted nucleotide sequence-related information or cryptographic key, whichever is not stored in the first memory area; and wherein the second computer is permitted to access a third memory area storing positional information and classification information concerning an object and/or service, and a fourth memory area storing positional information, a plurality of pieces of nucleotide sequence-related information corresponding to the positional information and semantic information associated, respectively, with each of the plurality of pieces of nucleotide sequence-related information, wherein the second computer searches the fourth memory area based on nucleotide sequence-related information received from the first computer to retrieve semantic information associated with the nucleotide sequence-related information received from the first computer and/or information on the semantic information, and wherein the method comprises:

(a) transmitting, via a communication network, a request for an object and/or service to the second computer;

(b) receiving, via a communication network, positional information in compliance with the request transmitted in step (a) from the second computer;

(c) retrieving either encrypted nucleotide sequence-related information or a cryptographic key that corresponds to the positional information received in step (b) from the first memory area;

(d) receiving, via a communication network, encrypted nucleotide sequence-related information or a cryptographic key, whichever is not stored in the first memory area, that corresponds to the positional information received in step (b) from the information provision computer for decryption;

(e) decrypting the encrypted nucleotide sequence-related information retrieved in step (c) or received in step (d) that corresponds to the positional information in compliance with the request using the cryptographic key received in step (d) or retrieved in step (c) and information for decryption to obtain nucleotide sequence-related information that corresponds to the positional information in compliance with the request; and (f) outputting, via a communication network, the nucleotide sequence-related information obtained in step (e) to the second computer; and wherein steps (a) through (f) are each executed by the first computer.

2. An information processing method concerning a nucleotide sequence, wherein the method is executed within a system that comprises a first computer, an information provision computer for decryption, a second computer and a third computer, which are connected to each other via a communication network, wherein the first computer comprises a transmitter/receiver and a processor, is permitted to access a first memory area storing positional information indicating a position within a nucleotide sequence and either encrypted nucleotide sequence-related information or cryptographic key regarding an individual, the encrypted nucleotide sequence-related information or the cryptographic key being set for at least one of a plurality of positions, and is capable of using information for decryption of the encrypted nucleotide sequence-related information based on the cryptographic key; and wherein the information provision computer for decryption is permitted to access a second memory area storing positional information and the encrypted nucleotide sequence-related information or cryptographic key, whichever is not stored in the first memory area; the second computer is permitted to access a third memory area storing positional information and a classification information concerning an object and/or service; and the third computer is permitted to access a fourth memory area storing positional information, a plurality of pieces of nucleotide sequence-related information corresponding to the positional information and semantic information associated, respectively, with each of the plurality of pieces of nucleotide sequence-related information, wherein the third computer searches the fourth memory area based on nucleotide sequence-related information received from the second computer to retrieve semantic information associated with the nucleotide sequence-related information received from the second computer and/or information on the semantic information, and wherein the method comprises:

(a) transmitting, via a communication network, a request for an object and/or service to the second computer;

(b) receiving, via a communication network, positional information in compliance with the request transmitted in step (a) from the second computer;

(c) retrieving either encrypted nucleotide sequence-related information or cryptographic key that corresponds to the positional information received in step (b) from the first memory area;

(d) receiving, via a communication network, encrypted nucleotide sequence-related information or cryptographic key, whichever is not stored in the first memory area, that corresponds to the positional information received in step (b) from the information provision computer for decryption;

(e) decrypting the encrypted nucleotide sequence-related information retrieved in step (c) or received in step (d) that corresponds to the positional information in compliance with the request using the cryptographic key received in step (d) or retrieved in step (c) and information for decryption to obtain nucleotide sequence-related information that corresponds to the positional information in compliance with the request; and (f) outputting, via a communication network, the nucleotide sequence-related information obtained in step (e) to the second computer; and wherein steps (a) through (f) are each executed by the first computer.

3. An information processing method concerning a nucleotide sequence, wherein the method is executed within a system that comprises a first computer, an information provision computer for decryption, a second computer, and a third computer, which are connected to each other via a communication network, wherein the first computer is permitted to access a first memory area storing positional information indicating a position within a nucleotide sequence and either encrypted nucleotide sequence-related information or cryptographic key regarding an individual, the encrypted nucleotide sequence-related information or the cryptographic key being set for at least one of a plurality of positions; and wherein the information provision computer for decryption is permitted to access a second memory area storing positional information and the encrypted nucleotide sequence-related information or cryptographic key, whichever is not stored in the first memory area; the second computer comprises a transmitter/receiver and a processor, is permitted to access a third memory area storing positional information and a classification information on an object and/or service, and is capable of using an information for decryption of the encrypted nucleotide sequence-related information based on the cryptographic key; and the third computer is permitted to access a fourth memory area storing positional information, a plurality of pieces of nucleotide sequence-related information corresponding to the positional information and semantic information associated, respectively, with each of the plurality of pieces of nucleotide sequence-related information, wherein the third computer searches the fourth memory area based on nucleotide sequence-related information received from the second computer to retrieve semantic information associated with the nucleotide sequence-related information received from the second computer and/or information on the semantic information, and wherein the method comprises:

(a) receiving, via a communication network, a request for an object and/or service from the first computer;

(b) searching the third memory area based on the request received in step (a) to retrieve positional information in compliance with the request;

(c) transmitting, via a communication network, positional information retrieved in step (b) to the first computer;

(d) receiving, via a communication network, encrypted nucleotide sequence-related information and cryptographic key corresponding to the positional information transmitted in step (c) from the first computer and the information provision computer for decryption, and decrypting the received encrypted nucleotide sequence-related information using the received cryptographic key and information for decryption to obtain nucleotide sequence-related information that corresponds to the positional information in compliance with the request; and (e) transmitting, via a communication network, the nucleotide sequence-related information obtained in step (d) to the third computer; and wherein steps (a) through (e) are each executed by the second computer.

4. A non-transitory recording medium having a program for processing information concerning a nucleotide sequence recorded thereon which allows a first computer to execute a method, wherein the method is executed within a system that comprises the first computer, an information provision computer for decryption, and a second computer, which are connected to each other via a communication network, wherein the first computer comprises a transmitter/receiver and a processor, and is permitted to access a first memory area storing positional information indicating a position within a nucleotide sequence and either encrypted nucleotide sequence-related information or a cryptographic key regarding an individual, the encrypted nucleotide sequence-related information or the cryptographic key being set for at least one of a plurality of positions, and is capable of using information for decryption of the encrypted nucleotide sequence-related information based on the cryptographic key; and wherein the information provision computer for decryption is permitted to access a second memory area storing positional information and the encrypted nucleotide sequence-related information or cryptographic key, whichever is not stored in the first memory area; and wherein the second computer is permitted to access a third memory area storing positional information and classification information concerning an object and/or service, and a fourth memory area storing positional information, a plurality of pieces of nucleotide sequence-related information corresponding to the positional information and semantic information associated, respectively, with each of the plurality of pieces of nucleotide sequence-related information, wherein the second computer searches the fourth memory area based on nucleotide sequence-related information received from the first computer to retrieve semantic information associated with the nucleotide sequence-related information received from the first computer and/or information on the semantic information, and wherein the method comprises:

(a) transmitting, via a communication network, a request for an object and/or service to the second computer;

(b) receiving, via a communication network, positional information in compliance with the request transmitted in step (a) from the second computer;

(c) retrieving either encrypted nucleotide sequence-related information or a cryptographic key that corresponds to the positional information received in step (b) from the first memory area;

(d) receiving, via a communication network, encrypted nucleotide sequence-related information or a cryptographic key, whichever is not stored in the first memory area, that corresponds to the positional information received in step (b) from the information provision computer for decryption;

(e) decrypting the encrypted nucleotide sequence-related information retrieved in step (c) or received in step (d) that corresponds to the positional information in compliance with the request using the cryptographic key received in step (d) or retrieved in step (c) and information for decryption to obtain nucleotide sequence-related information that corresponds to the positional information in compliance with the request; and (f) outputting, via a communication network, the nucleotide sequence-related information obtained in step (e) to the second computer; and wherein steps (a) through (f) are each executed by the first computer.

5. A non-transitory recording medium having a program for processing information concerning a nucleotide sequence recorded thereon which allows a first computer to execute a method, wherein the method is executed within a system that comprises the first computer, an information provision computer for decryption, a second computer and a third computer, which are connected to each other via a communication network, wherein the first computer comprises a transmitter/receiver and a processor, is permitted to access a first memory area storing positional information indicating a position within a nucleotide sequence and either encrypted nucleotide sequence-related information or cryptographic key regarding an individual, the encrypted nucleotide sequence-related information or the cryptographic key being set for at least one of a plurality of positions, and is capable of using information for decryption of the encrypted nucleotide sequence-related information based on the cryptographic key; and wherein the information provision computer for decryption is permitted to access a second memory area storing positional information and the encrypted nucleotide sequence-related information or cryptographic key, whichever is not stored in the first memory area; the second computer is permitted to access a third memory area storing positional information and a classification information concerning an object and/or service; and the third computer is permitted to access a fourth memory area storing positional information, a plurality of pieces of nucleotide sequence-related information corresponding to the positional information and semantic information associated, respectively, with each of the plurality of pieces of nucleotide sequence-related information, wherein the third computer searches the fourth memory area based on nucleotide sequence-related information received from the second computer to retrieve semantic information associated with the nucleotide sequence-related information received from the second computer and/or information on the semantic information, and wherein the method comprises:

(a) transmitting, via a communication network, a request for an object and/or service to the second computer;

(b) receiving, via a communication network, positional information in compliance with the request transmitted in step (a) from the second computer;

(c) retrieving either encrypted nucleotide sequence-related information or cryptographic key that corresponds to the positional information received in step (b) from the first memory area;

(d) receiving, via a communication network, encrypted nucleotide sequence-related information or cryptographic key, whichever is not stored in the first memory area, that corresponds to the positional information received in step (b) from the information provision computer for decryption;

(e) decrypting the encrypted nucleotide sequence-related information retrieved in step (c) or received in step (d) that corresponds to the positional information in compliance with the request using the cryptographic key received in step (d) or retrieved in step (c) and information for decryption to obtain nucleotide sequence-related information that corresponds to the positional information in compliance with the request; and (f) outputting, via a communication network, the nucleotide sequence-related information obtained in step (e) to the second computer; and wherein steps (a) through (f) are each executed by the first computer.

6. A non-transitory recording medium having a program for processing information concerning a nucleotide sequence recorded thereon which allows a second computer to execute a method, wherein the method is executed within a system that comprises a first computer, an information provision computer for decryption, the second computer, and a third computer, which are connected to each other via a communication network, wherein the first computer is permitted to access a first memory area storing positional information indicating a position within a nucleotide sequence and either encrypted nucleotide sequence-related information or cryptographic key regarding an individual, the encrypted nucleotide sequence-related information or the cryptographic key being set for at least one of a plurality of positions; and wherein the information provision computer for decryption is permitted to access a second memory area storing positional information and the encrypted nucleotide sequence-related information or cryptographic key, whichever is not stored in the first memory area; the second computer comprises a transmitter/receiver and a processor, is permitted to access a third memory area storing positional information and a classification information on an object and/or service, and is capable of using an information for decryption of the encrypted nucleotide sequence-related information based on the cryptographic key; and the third computer is permitted to access a fourth memory area storing positional information, a plurality of pieces of nucleotide sequence-related information corresponding to the positional information and semantic information associated, respectively, with each of the plurality of pieces of nucleotide sequence-related information, wherein the third computer searches the fourth memory area based on nucleotide sequence-related information received from the second computer to retrieve semantic information associated with the nucleotide sequence-related information received from the second computer and/or information on the semantic information, and wherein the method comprises:

(a) receiving, via a communication network, a request for an object and/or service from the first computer;

(b) searching the third memory area based on the request received in step (a) to retrieve positional information in compliance with the request;

(c) transmitting, via a communication network, positional information retrieved in step (b) to the first computer;

(d) receiving, via a communication network, encrypted nucleotide sequence-related information and cryptographic key corresponding to the positional information transmitted in step (c) from the first computer and the information provision computer for decryption, and decrypting the received encrypted nucleotide sequence-related information using the received cryptographic key and information for decryption to obtain nucleotide sequence-related information that corresponds to the positional information in compliance with the request; and (e) transmitting, via a communication network, the nucleotide sequence-related information obtained in step (d) to the third computer; and wherein steps (a) through (e) are each executed by the second computer.

7. An apparatus configured for executing a method of processing information concerning a nucleotide sequence, wherein the apparatus comprises a first computer, wherein the method is executed within a system that comprises the first computer, an information provision computer for decryption, and a second computer, which are connected to each other via a communication network, wherein the first computer comprises a transmitter/receiver and a processor, and is permitted to access a first memory area storing positional information indicating a position within a nucleotide sequence and either encrypted nucleotide sequence-related information or a cryptographic key regarding an individual, the encrypted nucleotide sequence-related information or the cryptographic key being set for at least one of a plurality of positions, and is capable of using information for decryption of the encrypted nucleotide sequence-related information based on the cryptographic key; and wherein the information provision computer for decryption is permitted to access a second memory area storing positional information and the encrypted nucleotide sequence-related information or cryptographic key, whichever is not stored in the first memory area; and wherein the second computer is permitted to access a third memory area storing positional information and classification information concerning an object and/or service, and a fourth memory area storing positional information, a plurality of pieces of nucleotide sequence-related information corresponding to the positional information and semantic information associated, respectively, with each of the plurality of pieces of nucleotide sequence-related information, wherein the second computer searches the fourth memory area based on nucleotide sequence-related information received from the first computer to retrieve semantic information associated with the nucleotide sequence-related information received from the first computer and/or information on the semantic information, and wherein the method comprises:

(a) transmitting, via a communication network, a request for an object and/or service to the second computer;

(b) receiving, via a communication network, positional information in compliance with the request transmitted in step (a) from the second computer;

(c) retrieving either encrypted nucleotide sequence-related information or a cryptographic key that corresponds to the positional information received in step (b) from the first memory area;

(d) receiving, via a communication network, encrypted nucleotide sequence-related information or a cryptographic key, whichever is not stored in the first memory area, that corresponds to the positional information received in step (b) from the information provision computer for decryption;

(e) decrypting the encrypted nucleotide sequence-related information retrieved in step (c) or received in step (d) that corresponds to the positional information in compliance with the request using the cryptographic key received in step (d) or retrieved in step (c) and information for decryption to obtain nucleotide sequence-related information that corresponds to the positional information in compliance with the request; and (f) outputting, via a communication network, the nucleotide sequence-related information obtained in step (e) to the second computer; and wherein steps (a) through (f) are each executed by the first computer.

8. An apparatus configured for executing a method of processing information concerning a nucleotide sequence, wherein the apparatus comprises a first computer, wherein the method is executed within a system that comprises the first computer, an information provision computer for decryption, a second computer and a third computer, which are connected to each other via a communication network, wherein the first computer comprises a transmitter/receiver and a processor, is permitted to access a first memory area storing positional information indicating a position within a nucleotide sequence and either encrypted nucleotide sequence-related information or cryptographic key regarding an individual, the encrypted nucleotide sequence-related information or the cryptographic key being set for at least one of a plurality of positions, and is capable of using information for decryption of the encrypted nucleotide sequence-related information based on the cryptographic key; and wherein the information provision computer for decryption is permitted to access a second memory area storing positional information and the encrypted nucleotide sequence-related information or cryptographic key, whichever is not stored in the first memory area; the second computer is permitted to access a third memory area storing positional information and a classification information concerning an object and/or service; and the third computer is permitted to access a fourth memory area storing positional information, a plurality of pieces of nucleotide sequence-related information corresponding to the positional information and semantic information associated, respectively, with each of the plurality of pieces of nucleotide sequence-related information, wherein the third computer searches the fourth memory area based on nucleotide sequence-related information received from the second computer to retrieve semantic information associated with the nucleotide sequence-related information received from the second computer and/or information on the semantic information, and wherein the method comprises:

(a) transmitting, via a communication network, a request for an object and/or service to the second computer;

(b) receiving, via a communication network, positional information in compliance with the request transmitted in step (a) from the second computer;

(c) retrieving either encrypted nucleotide sequence-related information or cryptographic key that corresponds to the positional information received in step (b) from the first memory area;

(d) receiving, via a communication network, encrypted nucleotide sequence-related information or cryptographic key, whichever is not stored in the first memory area, that corresponds to the positional information received in step (b) from the information provision computer for decryption;

(e) decrypting the encrypted nucleotide sequence-related information retrieved in step (c) or received in step (d) that corresponds to the positional information in compliance with the request using the cryptographic key received in step (d) or retrieved in step (c) and information for decryption to obtain nucleotide sequence-related information that corresponds to the positional information in compliance with the request; and (f) outputting, via a communication network, the nucleotide sequence-related information obtained in step (e) to the second computer; and wherein steps (a) through (f) are each executed by the first computer.

9. An apparatus configured for executing a method of processing information concerning a nucleotide sequence, wherein the apparatus comprises a second computer, wherein the method is executed within a system that comprises a first computer, an information provision computer for decryption, the second computer, and a third computer, which are connected to each other via a communication network, wherein the first computer is permitted to access a first memory area storing positional information indicating a position within a nucleotide sequence and either encrypted nucleotide sequence-related information or cryptographic key regarding an individual, the encrypted nucleotide sequence-related information or the cryptographic key being set for at least one of a plurality of positions; and wherein the information provision computer for decryption is permitted to access a second memory area storing positional information and the encrypted nucleotide sequence-related information or cryptographic key, whichever is not stored in the first memory area; the second computer comprises a transmitter/receiver and a processor, is permitted to access a third memory area storing positional information and a classification information on an object and/or service, and is capable of using an information for decryption of the encrypted nucleotide sequence-related information based on the cryptographic key; and the third computer is permitted to access a fourth memory area storing positional information, a plurality of pieces of nucleotide sequence-related information corresponding to the positional information and semantic information associated, respectively, with each of the plurality of pieces of nucleotide sequence-related information, wherein the third computer searches the fourth memory area based on nucleotide sequence-related information received from the second computer to retrieve semantic information associated with the nucleotide sequence-related information received from the second computer and/or information on the semantic information, and wherein the method comprises:

(a) receiving, via a communication network, a request for an object and/or service from the first computer;

(b) searching the third memory area based on the request received in step (a) to retrieve positional information in compliance with the request;

(c) transmitting, via a communication network, positional information retrieved in step (b) to the first computer;

(d) receiving, via a communication network, encrypted nucleotide sequence-related information and cryptographic key corresponding to the positional information transmitted in step (c) from the first computer and the information provision computer for decryption, and decrypting the received encrypted nucleotide sequence-related information using the received cryptographic key and information for decryption to obtain nucleotide sequence-related information that corresponds to the positional information in compliance with the request; and (e) transmitting, via a communication network, the nucleotide sequence-related information obtained in step (d) to the third computer; and wherein steps (a) through (e) are each executed by the second computer.

* * * * *